US007407790B2

(12) United States Patent
Hone

(10) Patent No.: US 7,407,790 B2
(45) Date of Patent: *Aug. 5, 2008

(54) RECOMBINANT DOUBLE-STRANDED RNA PHAGES AND USES THEREOF

(75) Inventor: David Hone, Rockville, MD (US)

(73) Assignee: University of Maryland Biotechnology Institute, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 10/525,702

(22) PCT Filed: Aug. 20, 2003

(86) PCT No.: PCT/US03/26200

§ 371 (c)(1),
(2), (4) Date: Dec. 20, 2005

(87) PCT Pub. No.: WO2004/018630

PCT Pub. Date: Mar. 4, 2004

(65) Prior Publication Data

US 2006/0147418 A1 Jul. 6, 2006

Related U.S. Application Data

(60) Provisional application No. 60/404,806, filed on Aug. 20, 2002.

(51) Int. Cl.
*C12N 7/00* (2006.01)
*C12N 7/01* (2006.01)
*C12N 7/02* (2006.01)

(52) U.S. Cl. .................................................. 435/235.1

(58) Field of Classification Search ....................... None
See application file for complete search history.

(56) References Cited

U.S. PATENT DOCUMENTS 5,877,159 A 3/1999 Powell et al.

OTHER PUBLICATIONS

Abacioglu, Y.H., Fouts, T.R., Laman, J.D. et al. Epitope mapping and topology of baculovirus-expressed HIV-1 gp160 determined with a panel of murine monoclonal antibodies. *AIDS Res. Hum. Retrovir.* 1994, 10(4), 371-381.

Agwale, S.M., Shata, M.T., Reitz, M.S., Jr. et al. A Tat subunit vaccine confers protective immunity against the immune-modulating activity of the human immunodeficiency virus type-1 Tat protein in mice. *Proc Natl Acad Sci U S A* 2002, 99(15), 10037-10041.

Andre, S., Seed, B., Eberle, J., Schraut, W., Bultmann, A. & Haas, J. Increased immune response elicited by DNA vaccination with a synthetic gp120 sequence with optimized codon usage. *J Virol* 1998, 72(2), 1497-1503.

Baba, T.W., Liska, V., Hofmann-Lehmann, R. et al. Human neutralizing monoclonal antibodies of the IgG1 subtype protect against mucosal simian-human immunodeficiency virus infection. *Nat. Med.* 2000, 6(2), 200-206.

Bagley, K.C., Shata, M.T., Onyabe, D.Y., DeVico, A.L., Fouts, T.R., Lewis, G.K. & Hone, D.M. Immunogenicity of DNA vaccines that direct the coincident expression of the 120 kDa glycoprotein of human immunodeficiency virus and the catalytic domain of cholera toxin. *Vaccine* 2003, 21, 3335-3341.

Balasuriya, U.B., Heidner, H.W., Davis, N.L. et al. Alphavirus replicon particles expressing the two major envelope proteins of equine arteritis virus induce high level protection against challenge with virulent virus in vaccinated horses. *Vaccine* 2002, 20(11-12), 1609-1617.

Bamford, D.H. & Palva, E.T. Structure of the lipid-containing bacteriophage phi 6. Disruption by Triton X-100 treatment. *Biochim Biophys Acta* 1980, 601(2), 245-259.

Berger, H. & Kennedy, K. Physical measurements on the lipid-containing bacteriophage phi 6. *Biochim Biophys Acta* 1980, 633(1), 68-76.

Berglund, P., Fleeton, M.N., Smerdou, C. & Liljestrom, P. Immunization with recombinant Semliki Forest virus induces protection against influenza challenge in mice. *Vaccine* 1999, 17(5), 497-507.

Brinster, C., Chen, M., Boucreux, D. et al. Hepatitis C virus non-structural protein 3-specific cellular immune responses following single or combined immunization with DNA or recombinant Semliki Forest virus particles. *J Gen Virol* 2002, 83(Pt 2), 369-381.

Caley, I.J., Betts, M.R., Irlbeck, D.M. et al. Humoral, mucosal, and cellular immunity in response to a human immunodeficiency virus type 1 immunogen expressed by a Venezuelan equine encephalitis virus vaccine vector. *J Virol* 1997, 71(4), 3031-3038.

Conley, A.J., Kessler, J.A., II, Boots, L.J. et al. The consequence of passive administration of an anti-human immunodeficiency virus type 1 neutralizing monoclonal antibody before challenge of chimpanzees with a primary virus isolate. *J. Virol.* 1996, 70(10), 6751-6758.

Conry, R.M., LoBuglio, A.F., Wright, M. et al. Characterization of a messenger RNA polynucleotide vaccine vector. *Cancer Res* 1995, 55(7), 1397-1400.

Dalemans, W., Delers, A., Delmelle, C. et al. Protection against homologous influenza challenge by genetic immunization with SFV-RNA encoding Flu-HA. *Ann N Y Acad Sci* 1995, 772, 255-256.

Davis, N.L., Brown, K.W. & Johnston, R.E. A viral vaccine vector that expresses foreign genes in lymph nodes and protects against mucosal challenge. *J Virol* 1996, 70(6), 3781-3787.

DeVico, A.L., Rahman, R., Welch, J. et al. Monoclonal antibodies raised against covalently crosslinked complexes of human immunodeficiency virus type 1 gp120 and CD4 receptor identify a novel complex-dependent epitope on gp 120. *Virol.* 1995, 211(2), 583-588.

(Continued)

*Primary Examiner*—Bruce Campell
*Assistant Examiner*—Nicole Kinsey White
(74) *Attorney, Agent, or Firm*—Steven J. Hultquist; Intellectual Property / Technology Law; Kelly K. Reynolds

(57) ABSTRACT

The present invention provides recombinant double stranded RNA phages (rdsRP) that express dsRNA-encoded genes in eukaryote cells. Recombinant dsRNA phages are useful for the expression of dsRNA expression cassettes encoding passenger genes, such as, but not restricted to, vaccine antigens, bioactive proteins, immunoregulatory proteins, antisense RNAs, and catalytic RNAs in eukaryotic cells or tissues. Methods are provided to deliver a recombinant dsRNA phage to eukaryotic cells and tissues, either by direct administration, formulated in lipid or polylactidecoglycolide, or by utilizing a bacterial vaccine vector.

32 Claims, 6 Drawing Sheets

OTHER PUBLICATIONS

Emini, E.A., Schleif, W.A., Nunberg, J.H. et al. Prevention of HIV-1 infection in chimpanzees by gp120 V3 domain-specific monoclonal antibody. *Nature* 1992, 355(6362), 728-730.

Emini, E.A., Nara, P.L., Schleif, W.A. et al. Antibody-mediated in vitro neutralization of human immunodeficiency virus type 1 abolishes infectivity for chimpanzees. *J. Virol*. 1990, 64(8), 3674-3678.

Fleeton, M.N., Sheahan, B.J., Gould, E.A., Atkins, G.J. & Liljestrom, P. Recombinant Semliki Forest virus particles encoding the prME or NS1 proteins of louping ill virus protect mice from lethal challenge. *J Gen Virol* 1999, 80 ( Pt 5), 1189-1198.

Fouts, T.R., Lewis, G.K. & Hone, D.M. Construction and characterization of a *Salmonella typhi*-based human immunodeficiency virus type 1 vector vaccine. *Vaccine* 1995, 13(6), 561-569.

Fouts, T.R., Tuskan, R., Godfrey, K. et al. Expression and characterization of a single-chain polypeptide analogue of the human immunodeficiency virus type 1 gp120-CD4 receptor complex. *J Virol* 2000, 74(24), 11427-11436.

Galan, J.E., Nakayama, K. & Curtiss, R.d. Cloning and characterization of the *asd* gene of *Salmonella typhimurium*: use in stable maintenance of recombinant plasmids in *Salmonella* vaccine strains. *Gene* 1990, 94(1), 29-35.

Gottlieb, P., Strassman, J., Qiao, X., Frilander, M., Frucht, A. & Mindich, L. In vitro packaging and replication of individual genomic segments of bacteriophage phi 6 RNA. *J Virol* 1992, 66(5), 2611-2616.

Gottlieb, P., Strassman, J., Frucht, A., Qiao, X.Y. & Mindich, L. In vitro packaging of the bacteriophage phi 6 ssRNA genomic precursors. *Virology* 1991, 181(2), 589-594.

Gottlieb, P., Strassman, J., Qiao, X.Y., Frucht, A. & Mindich, L. In vitro replication, packaging, and transcription of the segmented double-stranded RNA genome of bacteriophage phi 6: studies with procapsids assembled from plasmid-encoded proteins. *J Bacteriol* 1990, 172(10), 5774-5782.

Gottlieb, P., Metzger, S., Romantschuk, M. et al. Nucleotide sequence of the middle dsRNA segment of bacteriophage phi 6: placement of the genes of membrane-associated proteins. *Virology* 1988, 163(1), 183-190.

Haas, J., Park, E.C. & Seed, B. Codon usage limitation in the expression of HIV-1 envelope glycoprotein. *Curr Biol* 1996, 6(3), 315-324.

Haigwood, N.L., Watson, A., Sutton, W.F. et al. Passive immune globulin therapy in the SIV/macaque model: early intervention can alter disease profile. *Immunol. Lett*. 1996, 51(1-2), 107-114.

Hofmann-Lehmann, R., Vlasak, J., Rasmussen, R.A. et al. Postnatal passive immunization of neonatal macaques with a triple combination of human monoclonal antibodies against oral simian-human immunodeficiency virus challenge. *J. Virol*. 2001, 75(16), 7470-7480.

Hoogstraten, D., Qiao, X., Sun, Y., Hu, A., Onodera, S. & Mindich, L. Characterization of phi8, a bacteriophage containing three double-stranded RNA genomic segments and distantly related to phi6. *Virology* 2000, 272(1), 218-224.

Jang, S.K., Krausslich, H.G., Nicklin, M.J., Duke, G.M., Palmenberg, A.C. & Wimmer, E. A segment of the 5' nontranslated region of encephalomyocarditis virus RNA directs internal entry of ribosomes during in vitro translation. *J Virol* 1988, 62(8), 2636-2643.

Johnson, M.D., 3rd & Mindich, L. Plasmid-directed assembly of the lipid-containing membrane of bacteriophage phi 6. *J Bacteriol* 1994, 176(13), 4124-4132.

Kakitani, H., Iba, H. & Okada, Y. Penetration and partial uncoating of bacteriophage phi 6 particle. *Virol*. 1980, 101(2), 475-483.

Kang, C.Y., Hariharan, K., Nara, P.L., Sodroski, J. & Moore, J.P. Immunization with a soluble CD4-gp120 complex preferentially induces neutralizing anti-human immunodeficiency virus type 1 antibodies directed to conformation-dependent epitopes of gp120. *J. Virol*. 1994, 68(9), 5854-5862.

Kieft, J.S., Zhou, K., Jubin, R., Murray, M.G., Lau, J.Y. & Doudna, J.A. The hepatitis C virus internal ribosome entry site adopts an ion-dependent tertiary fold. *J Mol Biol* 1999, 292(3), 513-529.

Kieft, J.S., Zhou, K., Grech, A., Jubin, R. & Doudna, J.A. Crystal structure of an RNA tertiary domain essential to HCV IRES-mediated translation initiation. *Nat Struct Biol* 2002, 9(5), 370-374.

LaCasse, R.A., Follis, K.E., Trahey, M., Scarborough, J.D., Littman, D.R. & Nunberg, J.H. Fusion-competent vaccines: broad neutralization of primary isolates of HIV. *Science* 1999, 283(5400), 357-362.

Mascola, J.R., Lewis, M.G., Stiegler, G. et al. Protection of Macaques against pathogenic simian/human immunodeficiency virus 89.6PD by passive transfer of neutralizing antibodies. *J. Virol*. 1999, 73(5), 4009-4018.

Mascola, J.R., Stiegler, G., VanCott, T.C. et al. Protection of macaques against vaginal transmission of a pathogenic HIV-1/SIV chimeric virus by passive infusion of neutralizing antibodies. *Nat. Med*. 2000, 6(2), 207-210.

McGraw, T., Mindich, L. & Frangione, B. Nucleotide sequence of the small double-stranded RNA segment of bacteriophage phi 6: novel mechanism of natural translational control. *J Virol* 1986, 58(1), 142-151.

Menard, R., Sansonetti, P.J. & Parsot, C. Nonpolar mutagenesis of the ipa genes defines IpaB, IpaC, and IpaD as effectors of *Shigella flexneri* entry into epithelial cells. *J Bacteriol* 1993, 175(18), 5899-5906.

Mindich, L. Bacteriophage phi 6: a unique virus having a lipid-containing membrane and a genome composed of three dsRNA segments. *Adv Virus Res* 1988, 35, 137-176.

Mindich, L., Nemhauser, I., Gottlieb, P. et al. Nucleotide sequence of the large double-stranded RNA segment of bacteriophage phi 6: genes specifying the viral replicase and transcriptase. *J Virol* 1988, 62(4), 1180-1185.

Mindich, L. Precise packaging of the three genomic segments of the double-stranded-RNA bacteriophage phi6. *Microbiol. Mol. Biol. Rev*. 1999, 63(1), 149-160.

Mindich, L., Qiao, X., Qiao, J., Onodera, S., Romantschuk, M. & Hoogstraten, D. Isolation of additional bacteriophages with genomes of segmented double-stranded RNA. *J Bacteriol* 1999, 181(15), 4505-4508.

Mindich, L., Qiao, X., Onodera, S., Gottlieb, P. & Strassman, J. Heterologous recombination in the double-stranded RNA bacteriophage phi 6. *J Virol* 1992, 66(5), 2605-2610.

Mindich, L., Qiao, X. & Qiao, J. Packaging of multiple copies of reduced-size genomic segments by bacteriophage phi 6. *Virology* 1995, 212(1), 213-217.

Moore, J.P., Willey, R.L., Lewis, G.K., Robinson, J. & Sodroski, J. Immunological evidence for interactions between the first, second, and fifth conserved domains of the gp120 surface glycoprotein of human immunodeficiency virus type 1. *J. Virol*. 1994, 68(11), 6836-6847.

Moore, J.P., Thali, M., Jameson, B.A. et al. Immunochemical analysis of the gp120 surface glycoprotein of human immunodeficiency virus type 1: probing the structure of the C4 and V4 domains and the interaction of the C4 domain with the V3 loop. *J. Virol*. 1993, 67(8), 4785-4796.

Murthy, K.K., Cobb, E.K., Rouse, S.R., Lunceford, S.M., Johnson, D.E. & Galvan, A.R. Correlates of protective immunity against HIV-1 infection in immunized chimpanzees. *Immunol. Lett*. 1996, 51(1-2), 121-124.

Okahashi, N., Yamamoto, M., Vancott, J.L. et al. Oral immunization of interleukin-4 (IL-4) knockout mice with a recombinant *Salmonella* strain or cholera toxin reveals that CD4+ Th2 cells producing IL-6 and IL-10 are associated with mucosal immunoglobulin A responses. *Infect. Immun*. 1996, 64(5), 1516-1525.

Olkkonen, V.M. & Bamford, D.H. The nucleocapsid of the lipid-containing double-stranded RNA bacteriophage phi 6 contains a protein skeleton consisting of a single polypeptide species. *J Virol* 1987, 61(8), 2362-2367.

Olkkonen, V.M., Gottlieb, P., Strassman, J., Qiao, X.Y., Bamford, D.H. & Mindich, L. In vitro assembly of infectious nucleocapsids of bacteriophage phi 6: formation of a recombinant double-stranded RNA virus. *Proc. Natl. Acad. Sci*. 1990, 87(23), 9173-9177.

Onodera, S., Qiao, X., Qiao, J. & Mindich, L. Directed changes in the number of double-stranded RNA genomic segments in bacteriophage phi6. *Proc Natl Acad Sci U S A* 1998, 95(7), 3920-3924.

Onodera, S., Olkkonen, V.M., Gottlieb, P. et al. Construction of a transducing virus from double-stranded RNA bacteriophage phi6: establishment of carrier states in host cells. *J Virol* 1992, 66(1), 190-196.

Pal, R., DeVico, A., Rittenhouse, S. & Sarngadharan, M.G. Conformational perturbation of the envelope glycoprotein gp120 of human immunodeficiency virus type 1 by soluble CD4 and the lectin succinyl Con A. *Virology* 1993, 194(2), 833-837.

Parks, G.D., Duke, G.M. & Palmenberg, A.C. Encephalomyocarditis virus 3C protease: efficient cell-free expression from clones which link viral 5' noncoding sequences to the P3 region. *J. Virol.* 1986, 60(2), 376-384.

Parren, P.W., Ditzel, H.J., Gulizia, R.J. et al. Protection against HIV-1 infection in hu-PBL-SCID mice by passive immunization with a neutralizing human monoclonal antibody against the gp120 CD4-binding site. *Aids* 1995, 9(6), F1-6.

Phenix, K.V., Wark, K., Luke, C.J. et al. Recombinant Semliki Forest virus vector exhibits potential for avian virus vaccine development. *Vaccine* 2001, 19(23-24), 3116-3123.

Pincus, S.H., Wehrly, K., Cole, R. et al. In vitro effects of anti-HIV immunotoxins directed against multiple epitopes on HIV type 1 envelope glycoprotein 160. *AIDS Res. Hum. Retrovir.* 1996, 12(11), 1041-1051.

Price, B.M., Liner, A.L., Park, S., Leppla, S.H., Mateczun, A. & Galloway, D.R. Protection against anthrax lethal toxin challenge by genetic immunization with a plasmid encoding the lethal factor protein. *Infect. Immun.* 2001, 69(7), 4509-4515.

Pushko, P., Parker, M., Ludwig, G.V., Davis, N.L., Johnston, R.E. & Smith, J.F. Replicon-helper systems from attenuated Venezuelan equine encephalitis virus: expression of heterologous genes in vitro and immunization against heterologous pathogens in vivo. *Virology* 1997, 239(2), 389-401.

Putkonen, P., Thorstensson, R., Ghavamzadeh, L. et al. Prevention of HIV-2 and SIVsm infection by passive immunization in cynomolgus monkeys. *Nature* 1991, 352(6334), 436-438.

Qiao, X., Casini, G., Qiao, J. & Mindich, L. In vitro packaging of individual genomic segments of bacteriophage phi 6 RNA: serial dependence relationships. *J Virol* 1995, 69(5), 2926-2931.

Qiao, X., Qiao, J., Onodera, S. & Mindich, L. Characterization of phi 13, a bacteriophage related to phi 6 and containing three dsRNA genomic segments. *Virology* 2000, 275(1), 218-224.

Qiao, X., Qiao, J. & Mindich, L. An in vitro system for the investigation of heterologous RNA recombination. *Virology* 1997, 227(1), 103-110.

Sands, J.A. & Lowlicht, R.A. Temporal origin of viral phospholipids of the enveloped bacteriophage phi 6. *Can J Microbiol* 1976, 22(2), 154-158.

Shata, M.T. & Hone, D.M. Vaccination of a *Shigella* DNA vaccine vector induces antigen-specific $CD8^+$ T-cells and antiviral protective immunity. *J. Virol.* 2001, 75(20), 9665-9670.

Shata, M.T., Reitz, Jr., M.S., DeVico, A.L., Lewis, G.K. & Hone, D.M. Mucosal and systemic HIV-1 Env-specific $CD8^+$ T-cells develop after intragastric vaccination with a *Salmonella* Env DNA vaccine vector, *Vaccine* 2002, 20, 623-629.

Sinclair, J.F., Tzagoloff, A., Levine, D. & Mindich, L. Proteins of bacteriophage phi6. *J Virol* 1975, 16(3), 685-695.

Srinivasan, J., Tinge, S., Wright, R., Herr, J.C. & Curtiss, R., 3rd. Oral immunization with attenuated *Salmonella* expressing human sperm antigen induces antibodies in serum and the reproductive tract. *Biol. Reprod.* 1995, 53(2), 462-471.

Staats, H.F., Nichols, W.G. & Palker, T.J. Mucosal immunity to HIV-1: systemic and vaginal antibody responses after intranasal immunization with the HIV-1 C4/V3 peptide T1SP10 MN(A). *J. Immunol.* 1996, 157(1), 462-472.

Sullivan, N., Sun, Y., Sattentau, Q. et al. CD4-Induced conformational changes in the human immunodeficiency virus type 1 gp120 glycoprotein: consequences for virus entry and neutralization. *J. Virol.* 1998, 72(6), 4694-4703.

Van Etten, J.L., Vidaver, A.K., Koski, R.K. & Semancik, J.S. RNA polymerase activity associated with bacteriophage phi 6. *J Virol* 1973, 12(3), 464-471.

Van Etten, J.L., Vidaver, A.K., Koski, R.K. & Burnett, J.P. Base composition and hybridization studies of the three double-stranded RNA segments of bacteriophage phi 6. *J Virol* 1974, 13(6), 1254-1262.

Withoff, S., Glazenburg, K.L., van Veen, M.L. et al. Replication-defective recombinant Semliki Forest virus encoding GM-CSF as a vector system for rapid and facile generation of autologous human tumor cell vaccines. *Gene Ther* 2001, 8(20), 1515-1523.

Wu, S., Pascual, D.W., Lewis, G.K. & Hone, D.M. Induction of mucosal and systemic responses against human immunodeficiency virus type 1 glycoprotein 120 in mice after oral immunization with a single dose of a *Salmonella*-HIV vector. *AIDS Res. Hum. Retrovir.* 1997, 13(14), 1187-1194.

Wu, S., Pascual, D.W., VanCott, J.L. et al. Immune responses to novel *Escherichia coli* and *Salmonella typhimurium* vectors that express colonization factor antigen I (CFA/I) of enterotoxigenic *E. coli* in the absence of the CFA/I positive regulator *cfaR*. *Infect. Immun.* 1995, 63(12), 4933-4938.

Xu-Amano, J., Kiyono, H., Jackson, R.J. et al. Helper T cell subsets for immunoglobulin A responses: oral immunization with tetanus toxoid and cholera toxin as adjuvant selectively induces Th2 cells in mucosa associated tissues. *J. Exp. Med.* 1993, 178(4), 1309-1320.

Yamamoto, S., Kiyono, H., Yamamoto, M. et al. A nontoxic mutant of cholera toxin elicits Th2-type responses for enhanced mucosal immunity. *Proc. Natl. Acad. Sci.* 1997, 94(10), 5267-5272.

Zhou, X., Berglund, P., Rhodes, G., Parker, S.E., Jondal, M. & Liljestrom, P. Self-replicating Semliki Forest virus RNA as recombinant vaccine. *Vaccine* 1994, 12(16), 1510-1514.

He, Biao, et al., Phage RNA polymerase vectors that allow efficient gene expression in both prokaryotic and eukaryotic cells, Gene, 1995, pp. 75-79, vol. 164, No. 1.

Kassner, Paul D., et al., Genetic selection of phage engineered for receptor-mediated gene transfer to mammalian cells, Biochemical and Biophysical Research Communications, 1999, pp. 921-928, vol. 264.

Larocca, David, et al., Gene transfer to mammalian cells using genetically targeted filamentous bacteriophage, The FASEB Journal , 1999, pp. 727-734, vol. 13.

Odonera, Shiroh, et al., Reverse genetics and recombination in Phi 8, a dsRNA Bacteriophage, Virology, 2001, pp. 113-118, vol. 286.

Poul, Marie-Alix and Marks, James D., Targeted gene delivery to mammalian cells by filamentous bacteriophage, Journal of Molecular Biology, 1999, pp. 203-211, vol. 288.

Tsukiyama-Kohara, Kyoko, et al., Internal ribosome entry site within Hepatitis C virus RNA, Journal of Virology, 1992, pp. 1476-1483, vol. 66, No. 3.

RECOMBINANT DOUBLE-STRANDED RNA PHAGES AND USES THEREOF

CROSS-REFERENCE TO RELATED APPLICATIONS

This application is filed under the provisions of 35 U.S.C. §371 and claims the priority of International Patent Application No. PCT/US03/026200 filed on Aug. 20, 2003, which in turn claims priority of U.S. Provisional Patent Application No. 60/404,806 filed on Aug. 20, 2002.

STATEMENT OF GOVERNMENT RIGHTS

The United States Government has rights in this invention under NIATD Grant Nos, Al 41914, Al 47490 and Al 43756.

BACKGROUND OF THE INVENTION

1. Field of the Invention

The present invention generally relates to double stranded RNA phages, and more particularly, to recombinant double stranded RNA phages (hereinafter rdsRP) that express dsRNA-encoded genes in eukaryotic cells and used for the expression of dsRNA expression cassettes encoding passenger genes.

2. Background of the Related Art

Double stranded RNA phage (herein "dsRP") are atypical compared to other RNA and DNA phage, and more closely resemble members of the reoviridae family [1-5]. The distinguishing attributes of dsRP are a genome comprised of three double-stranded RNA (herein "dsRNA") segments [2-4,6] and a lipid-containing membrane coat [7-12]. The genomic segments are contained within the nucleocapsid core, which is comprised of the proteins P1, P2, P4, and P7, and is produced by genes encoded on the 7051 bp dsRNA segment, designated "segment L" (GeneBank Accession #AF226851). Synthesis of positive-strand RNA (herein "mRNA") occurs within the nucleocapsid, which is carried out by RNA-dependent RNA polymerase that may be encoded by gene 2 on segment L, based on sequence similarity to other bacterial RNA polymerases [4,13]. However, gene 7 on segment L also plays a pivotal role in mRNA synthesis [5].

DsRP phi-6, the archetype of this family of dsRNA phage, normally infects *Pseudomonas syringae [*5], however, more recently isolated dsRP phi-8, phi-11, phi-12 and phi-13 can replicate to some extent in *Escherichia coli* strain JM109 (American type tissue culture collection (herein "ATCC" # 53323) and O-antigen negative mutants of *Salmonella enterica serovar Typhimurium* (herein designated "*S. typhimurium*") [5,14-16].

By inserting a kanamycin-resistance allele into the M-segment of a dsRP, carrier strains were established and maintained [17]. Through this approach, several of the dsRPs were found to be capable of establishing a carrier state in host cells, in which infectious phage are continuously produced by the carrier strain [17]. The plaque-forming capacity of the phage produced by the carrier strains is maintained for three-five plate passages; however, after additional passages the nascent phage no longer formed plaques on the carrier strain, yet low-levels of infectious phage were still produced [17]. In some instances, a significant number of carrier strains lost the ability to produce infectious phage all together, yet phage dsRNA segments were continuously maintained in the cytosol of such carrier bacteria. The dsRNA from such bacterial strains displayed deletions in one of more of the segments. In one instance a mutant phage lacking the segment-S was isolated from one such carrier strain that had lost the capacity to produce phage [17,18].

The life cycle of the dsRP phi-6 in bacteria has been described [5,11]. Archetype dsRP phi-6 infects host cells by binding to the pilus. The phage then uses the pilus to allow contact with the host cell membrane, thereby resulting in fusion and introduction of the nucleocapsid into the periplasm. The nucleocapsid then is transported into the cytoplasm, an event that requires the endopeptidase activity of protein P5 and the transporting property of protein P8. Interestingly, nucleocapsids that bear a complete P8 shell are capable of spontaneous entry into bacterial protoplasts, resulting in auto-transfection of the bacterial strain from which the protoplasts were prepared [19,20].

Upon entering the cytoplasm, P8 is shed and the remaining nucleocapsid, which contains the three dsRNA segments and possesses RNA-dependent RNA polymerase activity, begins to synthesize mRNA copies of the dsRNA segments L, M and S as shown in FIG. 1. The proteins produced by segment L is mainly associated with procapsid production; segment M is mainly dedicated to the synthesis of the attachment proteins and the segment S produces the procapsid shell protein (P8), the lytic endopeptidase (P5), and the proteins (P9 and P12) involved in the generation of the lipid envelope [12] (FIG. 1).

Packaging of the dsRNA segments occurs in sequential manner, whereby segment S is recognized and taken up by empty procapsids; procapsids containing segment S no longer binds this segment but now are capable of binding and taking up segment M; procapsids that contain segments S and M no longer bind these segments but now are capable of binding and taking up segment L, resulting in the generation of the nucleocapsid. Once the nucleocapsid contains all three single-stranded RNA (herein "ssRNA") segments synthesis of the negative RNA strands begins to produce the dsRNA segments. The nucleocapsid then associates with proteins 5 and 8 as illustrated in FIG. 1 and finally is encapsulated in the lipid membrane, resulting the completion of phage assembly. Lysis of the host cell is thought to occur through the accumulation of the membrane disrupter protein P10, a product of segment M and requires the endopeptidase P5 [5].

The assembly of RNA polymerase and its activity in dsRP procapsids does not require host proteins, as procapsids purified from an *E. coli* JM109 derivative that expressed a cDNA copy of segment L are capable of packaging purified ssRNA segments L, M and S [5,19-24]. Following uptake of the ssRNA segments in the above in vitro system, addition of ribonucleotides resulted in negative strand synthesis and the generation of the mature dsRNA segments [5,19-24]. Furthermore, after the completion of dsRNA synthesis P8 associates with nucleocapsids and as indicated above the resultant product is capable of entering bacterial protoplasts and producing a productive infection [19,20].

There are several techniques for introducing nucleic acids into eukaryotic cells cultured in vitro. These include chemical methods (Felgner et al, *Proc. Natl. Acad. Sci., USA,* 84:7413-7417 (1987); Bothwell et al, *Methods for Cloning and Analysis of Eukaryotic Genes*, Eds., Jones and Bartlett Publishers Inc., Boston, Mass. (1990), Ausubel et al, *Short Protocols in Molecular Biology*, John Wiley and Sons, New York, N.Y. (1992); and Farhood, *Annal. N.Y. Acad. Sci.,* 716:23-34 (1994)), use of protoplasts (Bothwell, supra) or electrical pulses (Vatteroni et al, *Mutn. Res.,* 291:163-169 (1993); Sabelnikov, *Prog. Biophys. Mol. Biol.,* 62:119-152 (1994); Brothwell et al, supra; and Ausubel, et al, supra), use of attenuated viruses [25-34](Moss, *Dev. Biol. Stan.,* 82:55-63 (1994); and Brothwell et al, supra), as well as physical methods (Fynan et al, supra; Johnston et al, *Meth. Cell Biol,* 43(Part A):353-365 (1994); Brothwell et al, supra; and Ausubel et al, supra).

Successful delivery of nucleic acids to animal tissue has been achieved by cationic liposomes (Watanabe et al, *Mol. Reprod. Dev.,* 38:268-274 (1994)), direct injection of naked DNA or RNA into animal muscle tissue (Robinson et al, *Vacc.,* 11:957-960 (1993); Hoffman et al, *Vacc.,* 12:1529-1533; (1994); Xiang et al, *Virol.,* 199:132-140 (1994); Webster et al, *Vacc.,* 12:1495-1498 (1994); Davis et al, *Vacc.,* 12:1503-1509 (1994); and Davis et al, *Hum. Molec. Gen.,* 2:1847-1851 (1993); [35,36]), and embryos (Naito et al, *Mol. Reprod. Dev.,* 39:153-161 (1994); and Burdon et al, *Mol Reprod. Dev.,* 33:436-442 (1992)), intramuscular injection of self replicating RNA vaccines [25-28,35,36] or intradermal injection of DNA using "gene gun" technology (Johnston et al, supra).

The ribosomal binding site (RBS) is the site recognized by the ribosome for binding to the 5-prime (herein designated "5'") end of mRNA molecules. This binding is essential for the translation of mRNA into a protein by the ribosome. In prokaryotes, a defined RBS in the 5' end of the mRNA molecule that bears a sequence that is complementary to the 3' end of the small ribosomal RNA molecule (5S rRNA) (Chatteiji et al, *Ind. J. Biochem. Biophys.,* 29:128-134 (1992); and Darnell et al, supra; Lewin, supra; Watson et al, supra; and Watson et al, supra). Thus, in prokaryotes the RBS promotes association of the ribosome with the 5' end of the nascent mRNA molecule, whereupon translation is initiated at the first initiation codon encountered (i.e. normally the methionine codon AUG) by the mRNA-associated ribosome (Darnell et al, supra; Lewin, supra; Watson et al, supra; and Alberts et al, supra).

At present, no such recognition pattern has been observed in the 5' eukaryotic mRNA-ribosome interactions (Eick et al., supra). In addition, prior to initiation of translation of eukaryotic mRNA, the 5' end of the mRNA molecule is "capped" by addition of methylated guanylate to the first mRNA nucleotide residue (Darnell et al, supra; Lewin, supra; Watson et al, supra; and Alberts et al, supra). It has been proposed that recognition of the translational start site in mRNA by the eukaryotic ribosomes involves recognition of the cap, followed by binding to specific sequences surrounding the initiation codon on the mRNA.

It is possible for cap independent translation initiation to occur and/or to place multiple eukaryotic coding sequences within a eukaryotic expression cassette if a internal ribosome entry site (herein "IRES") sequence, such as the cap-independent translation enhancer (herein designated "CITE") derived from encephalomyocarditis virus (Duke et al, *J. Virol.,* 66:1602-1609 (1992)), is included prior to, or between, the coding regions. However, the initiating AUG codon is not necessarily the first AUG codon encountered by the ribosome (Louis et al, *Molec. Biol. Rep.,* 13:103-115 (1988); and Voorma et al, *Molec. Biol. Rep.,* 19:139-145 (1994); Lewin, supra; Watson et al, supra; and Alberts et al, supra). Thus, RBS sequences in eukaryotes are sufficiently divergent from that of prokaryotic RBS such that the two are not interchangeable.

The commercial application of nucleic acid delivery technology to eukaryotic cells is broad and includes delivery of vaccine antigens (Fynan et al, *Proc. Natl. Acad. Sci., USA,* 90:11478-11482 (1993)), immunotherapeutic agents, and bioactive proteins designed to remedy genetic disorders (Darris et al, *Cancer,* 74(3 Suppl.): 1021-1025 (1994); Magrath, *Ann. Oncol.,* 5(Suppl 1):67-70 (1994); Milligan et al, *Ann. NY Acad. Sci.,* 716:228-241 (1994); Schreier, *Pharma. Acta Helv.,* 68:145-159 (1994); Cech, *Biochem. Soc. Trans.,* 21:229-234 (1993); Cech, *Gene,* 135:33-36 (1993); Long et al, *FASEB J.,* 7:25-30 (1993); and Rosi et al, *Pharm. Therap.,* 50:245-254 1991)).

The delivery of nucleic acids to animal tissue for gene therapy has shown significant promise in experimental animals and volunteers, particularly where a transient effect is required (Nabel, *Circulation,* 91:541-548 (1995); Coovert et al, *Curr. Opin. Neuro.,* 7:463-470 (1994); Foa, *Bill. Clin. Haemat.,* 2:421-434 (1994); Bowers et al, *J. Am. Diet. Assoc.,* 95:53-59 (1995); Perales et al, *Eur. J. Biochem.,* 226:255-266 (1994); Danko et al, *Vacc.,* 12:1499-1502 (1994); Conry et al, *Canc. Res.,* 54:1164-1168 (1994); and Smith, *J. Hemat.,* 1:155-166 (1992)). Recently, naked DNA vaccines carrying eukaryotic expression cassettes have been used to successfully immunize against influenza both in chickens (Robinson et al, supra) and ferrets (Webster et al, *Vacc.,* 12:1495-1498 (1994)); against *Plasmodium yoelii* in mice (Hoffman et al, supra); against rabies in mice (Xiang et al, supra); against human carcinoembryonic antigen in mice (Conry et al, supra) and against hepatitis B in mice (Davis et al, supra). These observations open the additional possibility that delivery of nucleic acids to eukaryotic tissue could be used for both prophylactic and therapeutic applications, wherein the prophylactic application has a significant impact in the mortality and/or morbidity of the infectious agent, autoimmune disease or tumor prior to the acquisition of overt clinical disease, and the therapeutic application has a significant impact in the mortality and/or morbidity of the infectious agent, autoimmune disease or tumor following the development of overt clinical disease.

Therefore, there is a need to deliver eukaryotic expression cassettes, encoding endogenous or foreign genes that are vaccines or therapeutic agents to eukaryotic cells or tissue.

SUMMARY OF THE INVENTION

The present invention describes a novel and unexpected finding that double stranded RNA phage dsRP are capable of delivering dsRNA eukaryotic expression cassettes to eukaryotic cells and tissue. Heretofore, there has been no documented demonstration of dsRP invading eukaryotic cells and introducing a eukaryotic expression cassette(s), which then is translated by the infected cells and progeny thereof. That is, the present invention provides the first documentation of functional genetic exchange between dsRP and eukaryotic cells.

In one aspect, the present invention relates to the incorporation of eukaryotic cap-independent translation enhancer, herein referred to as "CITE" (also known as an internal ribosome entry site, herein referred to as "IRES") sequences into dsRP to enable expression in eukaryotic cells or tissues. As will be shown in more detail below the IRES sequence and a passenger gene of interest can be inserted into one or more of the three dsRNA segments in the dsRP. The resultant recombinant dsRP carrying a recombinant segment or segments produces messenger RNA in eukaryotic cells that is recognized by the eukaryotic translation apparatus. The ensuing translation by the eukaryotic cell ribosomes results in the expression of the passenger gene of interest.

Another aspect of the present invention relates to recombinant dsRP that carry alpha virus expression cassettes, including but not limited to the semliki forest virus [29-34] or venezuelan equine encephalitis (herein designated "VEE") virus [25-28], that are capable of self-amplification.

In yet another aspect of the present invention, methods are provided for the administration of recombinant dsRP to eukaryotic cells and tissues, and the use of recombinant dsRP to induce an immune response or to cause a biological affect in a target cell population.

In a still further aspect, the present invention relates to compositions and methods are described for the delivery of dsRP to mammalian cells and tissues using bacterial vectors, and the use of said bacterial vectors carrying recombinant dsRP to induce an immune response or to cause a biological affect in a target cell population.

In another aspect, the present invention relates to live bacteria that carry a recombinant dsRP containing one or more eukaryotic translation expression cassettes encoding dsRNA encoding IRES sequences that are functionally linked to one or more passenger genes.

In yet another aspect of the present invention, recombinant dsRP compositions are provided that incorporate an alphavirus expression cassette into said dsRP, thereby harnessing the mRNA-amplifying properties of said alpha virus, resulting in the generation of dsRP that are capable of substantively amplifying the mRNA of a passenger RNA-encoded gene in eukaryotic cells.

In another aspect, the present invention relates to live bacteria that carry a recombinant dsRP containing one or more eukaryotic translation expression cassettes encoding dsRNA encoding IRES sequences that are functionally linked to one or more passenger genes.

In yet another aspect, recombinant dsRP compositions are provided that incorporate an alpha-virus expression cassette into said dsRP, thereby harnessing the mRNA-amplifying properties of said alpha virus, resulting in the generation of dsRP that are capable of substantively amplifying the mRNA of a passenger RNA-encoded gene in eukaryotic cells.

These and other objects of the present invention, which will be apparent from the detailed description of the invention provided hereinafter, have been met in an embodiment by providing compositions and methods for introducing and expressing a gene into eukaryotic cells, comprising infecting said cells with a recombinant dsRP carrying a eukaryotic translation expression cassette comprised of dsRNA sequences encoding an IRES and the green fluorescent protein (herein designated "GFP"), wherein said dsRP carrying said eukaryotic translation expression cassette is capable of expressing GFP in eukaryotic cells.

DETAILED DESCRIPTION OF PREFERRED EMBODIMENTS

Figure 1:
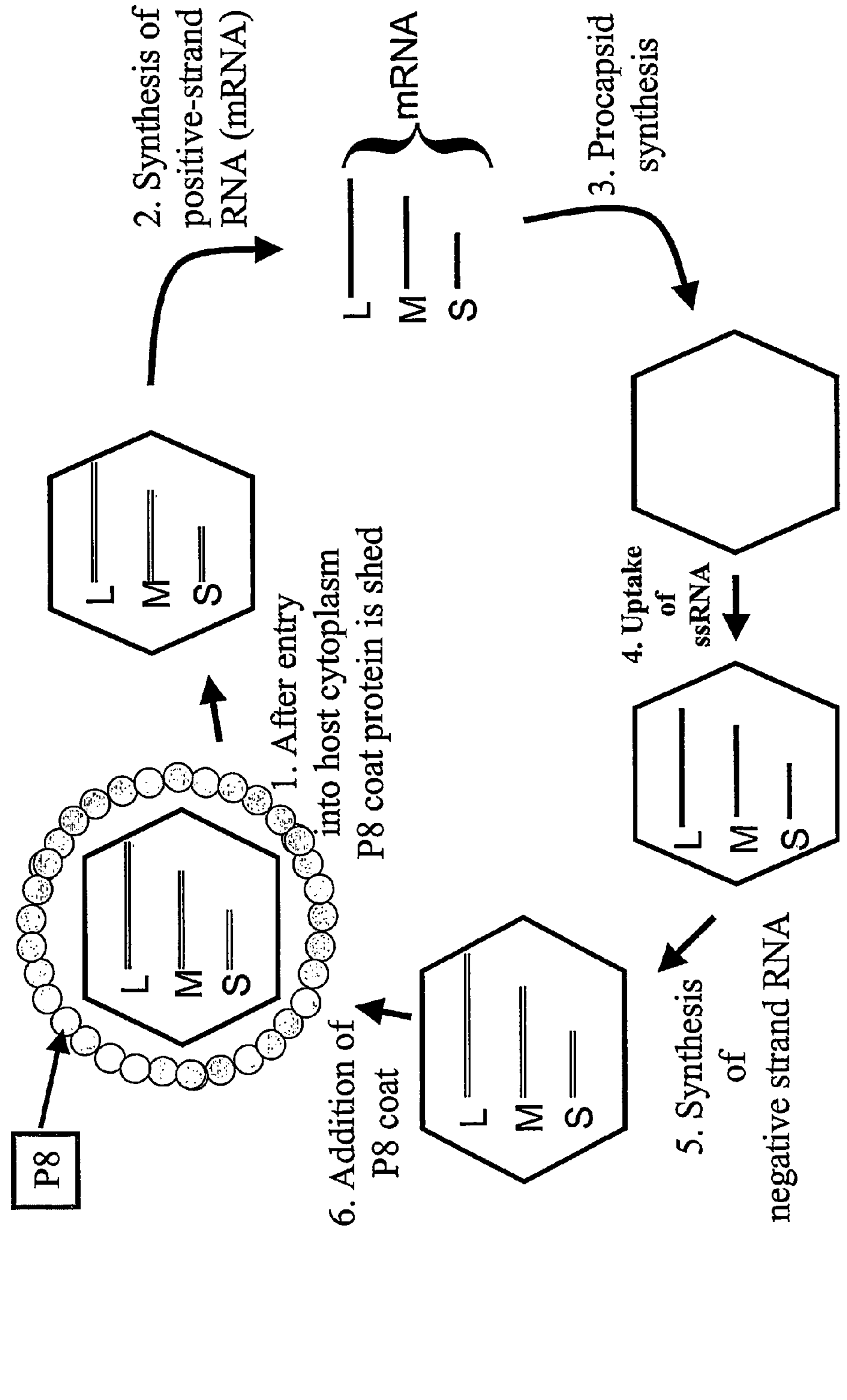
FIG. 1 illustrates the replication of dsRP nucleocapsids in bacterial cytoplasm.

As mentioned above in one embodiment of the present invention recombinant dsRP (herein referred to as "rdsRP") are provided that express dsRNA-encoded genes in eukaryote cells. Normally, dsRP-encoded genes are poorly translated in eukaryotic cells due to the lack of cap-independent eukaryotic translation signaling sequences that are necessary to launch efficient ribosome binding and the translation of mRNA sequences into protein. Below rdsRP are provided that produce mRNA molecules containing the appropriate translation initiation sequences that enable efficient recognition and translation in eukaryotic cells. It is surprising that only a simple modification to a prokaryotic virus (i.e. dsRP) results in efficient expression in a eukaryotic cell.

Recombinant DNA Techniques

The recombinant DNA procedures used in the construction of the following rdsRP, including PCR, restriction endonuclease (herein referred to as "RE") digestions, DNA ligation, agarose gel electrophoresis, DNA purification, and dideoxynucleotide sequencing, are described elsewhere [37-40] Miller, *A Short Course in Bacterial Genetics*, Cold Spring Harbor Laboratory Press, Cold Spring Harbor, N.Y. (1992); Bothwell et al, supra; and Ausubel et al, supra), bacteriophage-mediated transduction (de Boer, supra; Miller, supra; and Ausubel et al, supra), or chemical (Bothwell et al, supra; Ausubel et al, supra; Felgner et al, supra; and Farhood, supra), electroporation (Bothwel et al, supra; Ausubel et al, supra; and Sambrook, *Molecular Cloning: A Laboratory Manual*, Cold Spring Harbor Laboratory Press, Cold Spring Harbor, N.Y.) and physical transformation techniques (Johnston et al, supra; and Bothwell, supra). The genes can be incorporated on phage (de Boer et al, *Cell,* 56:641-649 (1989)), plasmids vectors (Curtiss et al, supra) or spliced into the chromosome (Hone et al, supra) of the target strain.

Gene sequences can be made synthetically using an Applied Biosystems ABI™ 3900 High-Throughput DNA Synthesizer (Foster City, Calif. 94404 U.S.A.) and procedures provided by the manufacturer. To synthesize large sequences i.e., greater than 200 bp, a series of segments of the full-length sequence are generated by PCR and ligated together to form the full-length sequence using procedures well know in the art [41-43]. However, smaller sequences, i.e. those smaller than 200 bp, can be made synthetically in a single round using an Applied Biosystems ABI™ 3900 High-Throughput DNA Synthesizer (Foster City, Calif. 94404 U.S.A.) and procedures provided by the manufacturer.

Recombinant plasmids are introduced into bacterial strains by electroporation using a BioRad Gene-Pulser® set at 200Ω, 25 μF and 2.5 kV (BioRad Laboratories, Hercules, Calif.) [38]. Nucleotide sequencing to verify cDNA sequences is accomplished by standard automated sequencing techniques (Applied Biosystems automated sequencer, model 373A). DNA primers for DNA sequencing and polymerase chain reaction (herein referred to as "PCR") are synthesized using an Applied Biosystems ABI™ 3900 High-Throughput DNA Synthesizer (Foster City, Calif. 94404 U.S.A.).

Source of IRES Sequences mRNA molecules lacking a 5' cap modifier, which is normally added in the nucleus to nuclear mRNA transcripts and enhances ribosome recognition, are poorly translated in eukaryotic cells unless an IRES sequence is present upstream of the gene of interest. The particular IRES employed in the present invention is not critical and can be selected from any of the commercially available vectors that contain IRES sequences. Thus, IRES sequences are widely available and can be obtained commercially from plasmid pIRES2-EGFP (BD Biosciences Clontech Catalog No. 6029-1; [44]SEQ ID NO: 6)) by PCR using primers specific for the 5' and 3' ends of the IRES located at nucleotides 665-1251 in pIRES2-EGFP. The sequences in plasmid pIRES-EGFP can be obtained from the manufacturer (http://www.clontech.com/techinfo/vectors/vectorsF-I/pdf/pIRES2-EGFPseq.pdf). A similar IRES can also be obtained from plasmid pCITE4a (Novagen, Madison Wis.; see also U.S. Pat. No. 4,937,190) by PCR using primers specific for the 5' and 3' ends of the CITE from nucleotides 16 to 518 in plasmid pCITE4a (the complete sequence of pCITE4a is available at http://www.novagen.com/docs/NDIS/69913-000.HTM). on plasmids pCLIE4a-c (Novagen, URL:—http://www.novagen.com; U.S. Pat. No. 4,937,190); pSLIRES11 (Accession: AF171227; pPV (Accession # Y07702); pSVIRES-N (Accession #: AJ000156); Creancier et al., J. Cell Biol., 10: 275-281 (2000); Ramos and Martinez-Sala, RNA, 10: 1374-1383 (1999); Morgan et al. Nucleic Acids Res., 20: 1293-1299 (1992); Tsukiyama-Kohara et al. J. Virol., 66: 1476-1483 (1992); Jang and Wimmer et al. Genes Dev., 4: 1560-1572 (1990)), or on the dicistronic retroviral vector (Accession #: D88622); or found in eukaryotic cells such as the fibroblast growth factor 2 IRES for stringent tissue-specific regulation (Creancier, et al., J. Cell. Biol., 150:275 (2000)) or the Internal-ribosome-entry-site of the 3'-untranslated region of the mRNA for the beta subunit of mitochondrial $H^+$-ATP synthase (Izquierdo and Cuezva, Biochem. J., 346:849 (2000)).

Non-commercial source of IRES's can also be located. Thus, plasmid pIRES-G (Hobbs, S. M. CRC Centre for Cancer Therapeutics, Institute of Cancer Research, Block F, 15, Cotswold Road, Belmont, Sutton, Surrey SM2 5NG, UK) will serve as source of IRES and the sequence of this plasmid is available (Genebank accession no. Y11034). Furthermore, an Internet search using the NCBI nucleotide database (http://www.ncbi.nlm.nih.gov/entrez/query.fcgi?CMD=Display&DB=nucleotide) and the search parameter "IRES not patent" yields 41 Files containing IRES sequences. Finally, IRES cDNA can be made synthetically using an Applied Biosystems ABI™ 3900 High-Throughput DNA Synthesizer (Foster City, Calif. 94404 U.S.A.), using procedures provided by the manufacturer. To synthesize large IRES sequences such as the 502 bp IRES in pCITE4a, a series of segments are generated by PCR and ligated together to form the full-length sequence using procedures well know in the art [41-43]. Smaller IRES sequences such as the 53 bp IRES in hepatitis C virus (Genebank accession no. 1KH6_A; [45,46]) can be made synthetically in a single round using an Applied Biosystems ABI™ 3900 High-Throughput DNA Synthesizer (Foster City, Calif. 94404 U.S.A.) and procedures provided by the manufacturer.

Examples of Genes of Interest that can be Inserted in dsRP

In the present invention, the gene of interest (GOI) introduced on a eukaryotic translation expression cassette into the rdsRP may encode an immunogen, which may be either a foreign immunogen from viral, bacterial and parasitic pathogens, or an endogenous immunogen, such as but not limited to an autoimmune antigen or a tumor antigen. The immunogens may be the full-length native protein, chimeric fusions between the foreign immunogen and an endogenous protein or mimetic, a fragment or fragments thereof of an immunogen that originates from viral, bacterial and parasitic pathogens.

The term "foreign immunogen," as used herein is defined as a protein or fragment thereof, which is not normally expressed in the recipient animal cell or tissue, such as, but not limited to, viral proteins, bacterial proteins, parasite proteins, cytokines, chemokines, immunoregulatory agents, or therapeutic agents.

The term "endogenous immunogen," as used herein is defined as a protein or part thereof that is naturally present in the recipient animal cell or tissue, such as, but not limited to, an endogenous cellular protein, an immunoregulatory agent, or a therapeutic agent.

Alternatively or additionally, the immunogen may be encoded by a synthetic gene and may be constructed using conventional recombinant DNA methods (See above).

The foreign immunogen can be any molecule that is expressed by any viral, bacterial, or parasitic pathogen prior to or during entry into, colonization of, or replication in their animal host; the rdsRP may express immunogens or parts thereof that originate from viral, bacterial and parasitic pathogens. These pathogens can be infectious in humans, domestic animals or wild animal hosts.

The viral pathogens, from which the viral antigens are derived, include, but are not limited to, Orthomyxoviruses, such as influenza virus (Taxonomy ID: 59771; Retroviruses, such as RSV, HTLV-1 (Taxonomy ID: 39015), and HTLV-II (Taxonomy ID: 11909), Herpesviruses such as EBV Taxonomy ID: 10295); CMV (Taxonomy ID: 10358) or herpes simplex virus (ATCC #: VR-1487); Lentiviruses, such as HIV-1 (taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia (Taxonomy ID: 10245); Rotavirus taxonomy ID: 10912); and Parvoviruses, such as adeno-associated virus 1 (Taxonomy ID: 85106).

Examples of viral antigens can be found in the group including but not limited to the human immunodeficiency virus antigens Nef (National Institute of Allergy and Infectious Disease HIV Repository Cat. # 183; Genbank accession # AF238278), Gag, Env (National Institute of Allergy and Infectious Disease HIV Repository Cat. # 2433; Genbank accession # U39362), Tat (National Institute of Allergy and Infectious Disease HIV Repository Cat. # 827; Genbank accession # M13137), mutant derivatives of Tat, such as Tat-Δ31-45 (Agwale et al. *Proc. Natl. Acad. Sci. In press. Jul. 8th* (2002)), Rev (National Institute of Allergy and Infectious Disease HIV Repository Cat. # 2088; Genbank accession # L14572), and Pol (National Institute of Allergy and Infectious Disease HIV Repository Cat. # 238; Genbank accession # AJ237568) and T and B cell epitopes of gp120 (Hanke and McMichael, AIDS Immunol Lett., 66:177 (1999); Hanke, et al., *Vaccine,* 17:589 (1999); Palker et al, *J. Immunol.* 142: 3612-3619 (1989)) chimeric derivatives of HIV-1 Env and gp120, such as but not restricted to fusion between gp120 and CD4 (outs et al., *J. Virol.* 2000, 74:11427-11436 (2000)); truncated or modified derivatives of HIV-1 env, such as but not restricted to gp140 (Stamatos et al. *J. Virol.* 72:9656-9667 (1998)) or derivatives of HIV-1 Env and/or gp140 thereof (Binley, et al. *J Virol,* 76:2606-2616 (2002); Sanders, et al. *J Virol,* 74:5091-5100 (2000); Binley, et al. *J Virol.* 74:627-643 (2000)), the hepatitis B surface antigen (Genbank accession # AF043578; Wu et al, *Proc. Natl. Acad. Sci., USA,* 86:4726-4730 (1989)); rotavirus antigens, such as VP4 (Genbank accession # AJ293721; Mackow et al, *Proc. Natl. Acad. Sci., USA,* 87:518-522 (1990)) and VP7 (GenBank accession # AY003871; Green et al, *J. Virol.,* 62:1819-1823 (1988)), influenza virus antigens such as hemagglutinin or (GenBank accession # AJ404627; Pertmer and Robinson, Virology, 257: 406 (1999)); nucleoprotein (GenBank accession # AJ289872; Lin et al, Proc. Natl. Acad. Sci., 97: 9654-9658 (2000))) herpes simplex virus antigens such as thymidine kinase (Genbank accession # AB047378; Whitley et al, *In: New Generation Vaccines*, pages 825-854).

The bacterial pathogens, from which the bacterial antigens are derived, include but are not limited to, *Mycobacterium* spp., *Helicobacter pylori, Salnionella* spp., *Shigella* spp., *E.*

*coli, Rickettsia* spp., *Listenia* spp., *Legionella pneumoniae, Pseudomonas* spp., *Vibrio* spp., and *Borellia burgdorferi.*

Examples of protective antigens of bacterial pathogens include the somatic antigens of enterotoxigenic *E. coli*, such as the CFA/I fimbrial antigen (Yamamoto et al, *Infect. Immun.,* 50:925-928 (1985)) and the nontoxic B-subunit of the heat-labile toxin (Klipstein et al, *Infect. Immun.,* 40:888-893 (1983)); pertactin of *Bordetella pertussis* Roberts et al, *Vacc.,* 10:43-48 (1992)), adenylate cyclase-hemolysin of *B. pertussis* (Guiso et al, *Micro. Path.,* 11:423-431 (1991)), fragment C of tetanus toxin of *Clostridium tetani* (Fairweather et al, *Infect. Immun.,* 58:1323-1326 (1990)), OspA of *Borellia burgdorferi* (Sikand, et al. *Pediatrics,* 108:123-128 (2001); Wallich, et al. *Infect Immun.* 69:2130-2136 (2001)), protective paracrystalline-surface layer proteins of *Rickettsia prowazekii* and *Rickettsia typhi* (Carl, et al. *Proc Natl Acad Sci U S A,* 87:8237-8241 (1990)), the listeriolysin (also known as "Llo" and "Hly") and/or the superoxide dismutase (also know as "SOD" and "p60") of *Listeria monocytogenes* (Hess, J., et al. *Infect. Immun.* 65:1286-92 (1997); Hess, J., et al. *Proc. Natl. Acad. Sci.* 93:1458-1463 (1996); Bouwer, et al. *J. Exp. Med.* 175:1467-71(1992)), the urease of *Helicobacter pylori* (Gomez-Duarte, et al. *Vaccine* 16, 460-71 (1998); Corthesy-Theulaz, et al. *Infection* & *Immunity* 66, 581-6 (1998)), and the receptor-binding domain of lethal toxin and/ or the protective antigen of *Bacillus anthrax* (Price, et al. *Infect. Immun.* 69, 4509-4515 (2001)).

The parasitic pathogens, from which the parasitic antigens are derived, include but are not limited to, *Plasmzodium* spp., such as *Plasmodium falciparum* (ATCC#: 30145); *Trypanosome* spp., such as *Trypanosoma cruzi* (ATCC#: 50797); *Giardia* spp., such as *Giardia* intestinalis (ATCC#: 30888D); *Boophilus* spp., *Babesia* spp., such as *Babesia microti* (ATCC#: 30221); *Entamoeba* spp., such as *Entamoeba histolytica* (ATCC#: 30015); *Eimeria* spp., such as Eimeria maxima (ATCC# 40357); *Leishmania* spp. (Taxonomy ID: 38568); *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite antigens of *Plasmodium* spp. (Sadoff et al, *Science,* 240:336-337 (1988)), such as the circumsporozoite antigen of *P. bergerii* or the circumsporozoite antigen of *P. falciparum*; the merozoite surface antigen of *Plasmodium* spp. (Spetzler et al, *Int. J. Pept. Prot. Res.,* 43:351-358 (1994)); the galactose specific lectin of *Entamoeba histolytica* (Mann et al, *Proc. Natl. Acad. Sci., USA,* 88:3248-3252 (1991)), gp63 of *Leishmania* spp. (Russell et al, *J. Immunol.,* 140:1274-1278 (1988); Xu and Liew, Immunol., 84: 173-176 (1995)), gp46 of Leishmania major (Handman et al, Vaccine, 18: 3011-3017 (2000)paramyosin of *Brugia malayi* (Li et al, *Mol. Biochem. Parasitol.,* 49:315-323 (1991)), the triose-phosphate isomerase of *Schistosoma mansoni* (Shoemaker et al., *Proc. Natl. Acad. Sci.*, USA, 89:1842-1846 (1992)); the secreted globin-like protein of *Trichostrongylus colubriformis* (Frenkel et al, *Mol. Biochem. Parasitol.,* 50:27-36 (1992)); the glutathione-S-transferase's of Frasciola hepatica (Hillyer et al, *Exp. Parasitol.,* 75:176-186 (1992)), *Schistosoma bovis* and *S. japonicum* (Bashir et al, *Trop. Geog. Med.,* 46:255-258 (1994)); and KLH of *Schistosoma bovis* and *S. japonicum* (Bashir et al, supra).

As mentioned earlier, the dsRP vaccine may encode an endogenous immunogen, which may be any cellular protein, immunoregulatory agent, or therapeutic agent, or parts thereof, that may be expressed in the recipient cell, including but not limited to tumor, transplantation, and autoimmune immunogens, or fragments and derivatives of tumor, transplantation, and autoimmune immunogens thereof. Thus, in the present invention, dsRP may encode tumor, transplant, or autoimmune immunogens, or parts or derivatives thereof. Alternatively, the dsRP may encode synthetic genes (made as described above), which encode tumor-specific, transplant, or autoimmune antigens or parts thereof.

Examples of tumor specific antigens include prostate specific antigen (Gattuso et al, *Human Pathol.,* 26:123-126 (1995)), TAG-72 and CEA (Guadagni et al., *Int. J. Biol. Markers,* 9:53-60 (1994)), MAGE-1 and tyrosinase (Coulie et al, *J. Immunothera.,* 14:104-109 (1993)). Recently it has been shown in mice that immunization with non-malignant cells expressing a tumor antigen provides a vaccine effect, and also helps the animal mount an immune response to clear malignant tumor cells displaying the same antigen Koeppen et al, *Anal N.Y. Acad. Sci.,* 690:244-255 (1993)).

Examples of transplant antigens include the CD3 molecule on T cells (Alegre et al, *Digest. Dis. Sci.,* 40:58-64 (1995)). Treatment with an antibody to CD3 receptor has been shown to rapidly clear circulating T cells and reverse cell-mediated transplant rejection (Alegre et al, supra).

Examples of autoimmune antigens include IAS β chain (Topham et al, *Proc. Natl. Acad. Sci., USA,* 91:8005-8009 (1994)). Vaccination of mice with an 18 amino acid peptide from IAS chain has been demonstrated to provide protection and treatment to mice with experimental autoimmune encephalomyelitis (Topham et al, supra).

Introduction of Sequences into dsRP

Figure 2:
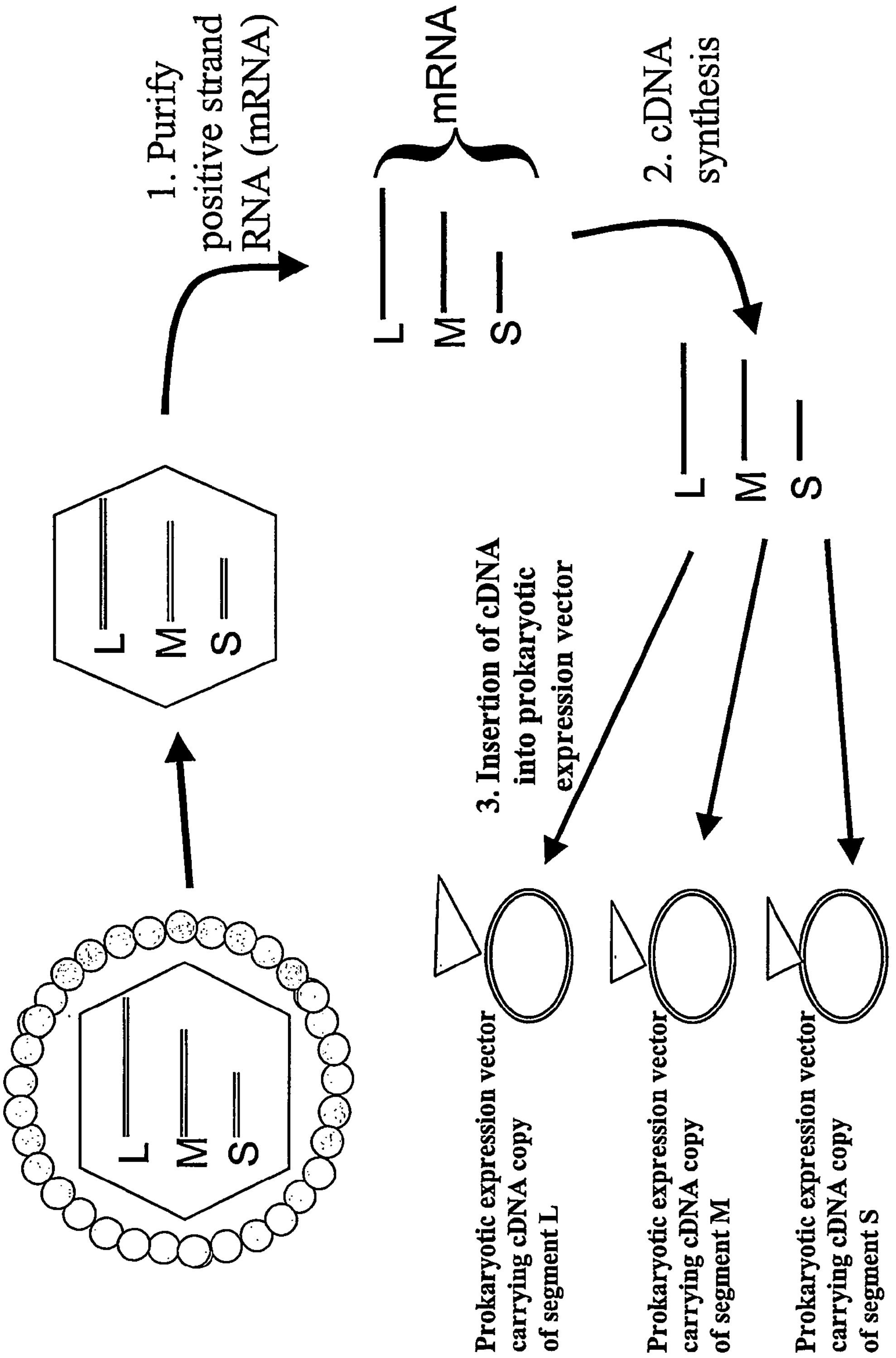
FIG. 2 illustrates the scheme for cloning cDNA copies of the mRNA produced by dsRP.
Figure 3:
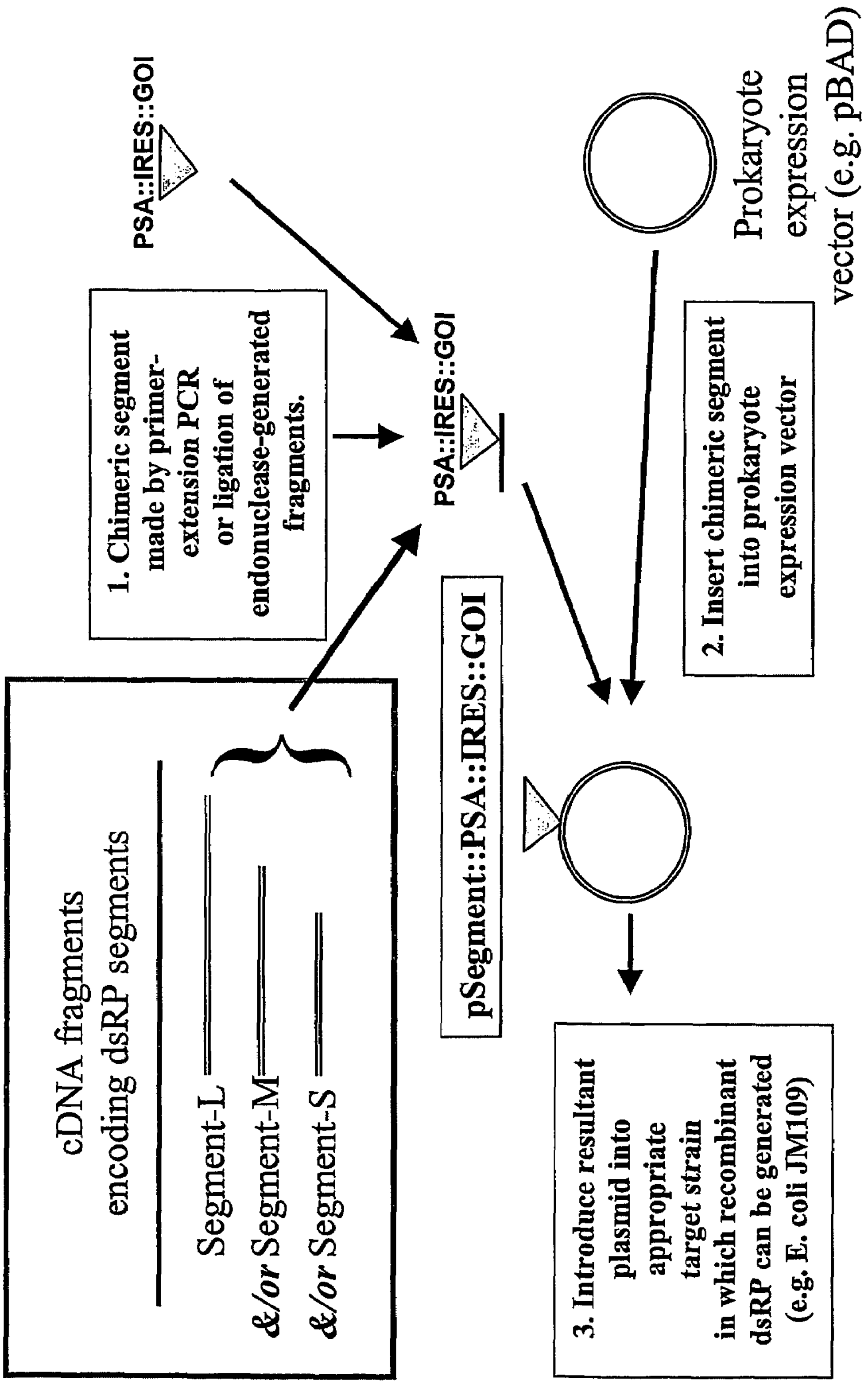
FIG. 3 illustrates the construction of recombinant dsRP segments using cDNA clones.
Figure 4:
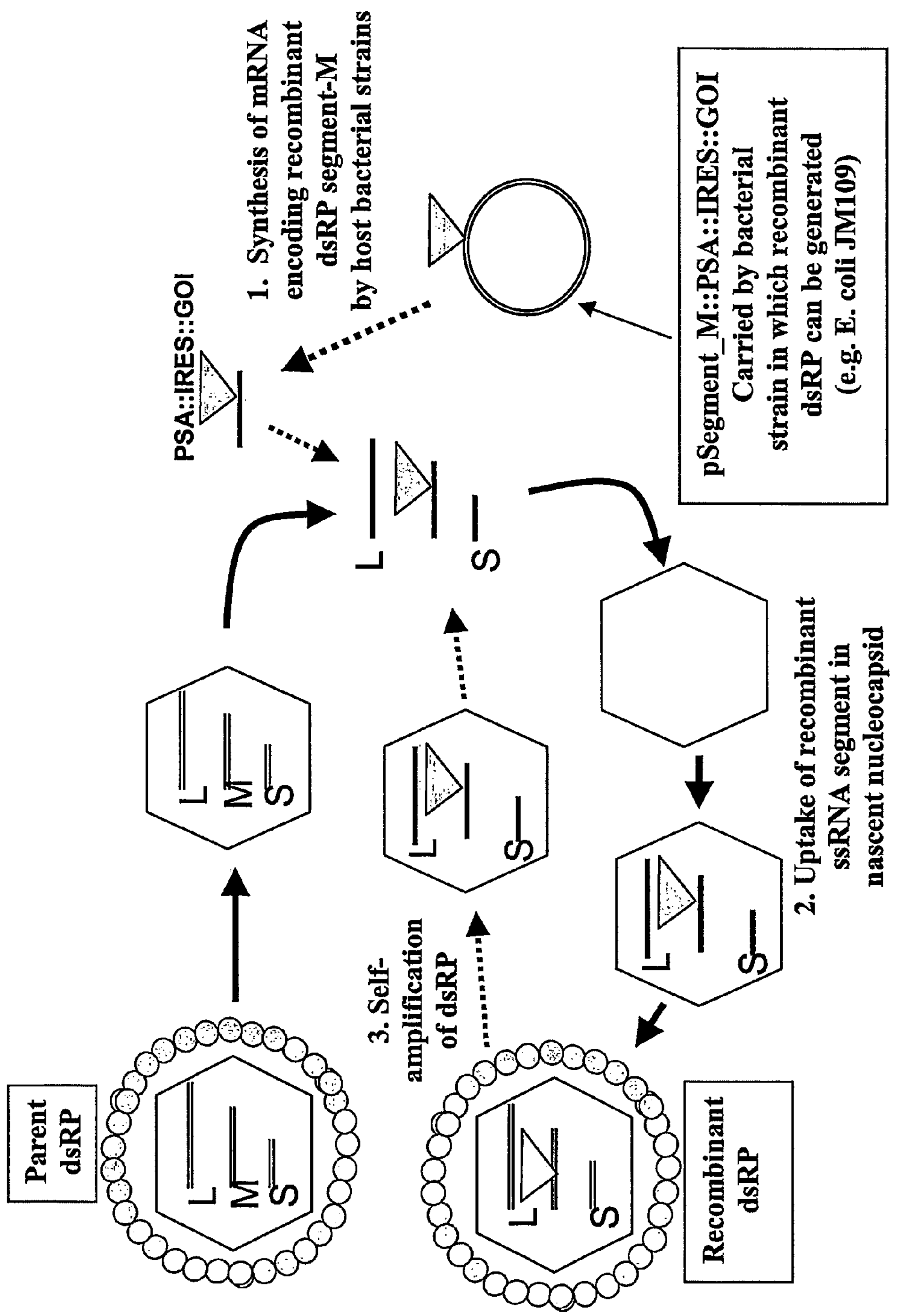
FIG. 4 illustrates the generation of recombinant dsRP nucleocapsids.

To manipulate dsRP, cDNA copies of the mRNA segments L, M and S are generated and inserted into a prokaryotic expression vector using procedures well known in the art (Ausubel et al, supra; and Sambrook, supra) and illustrated in FIG. 2. These cloned cDNA copies of the mRNA are used as target sequences into which the sequence of interest that encodes the gene of interest GOI is inserted (FIGS. 3 and 4).

To generate rdsRP that retain the capacity to produce infectious phage, the sequence that is being incorporated into the dsRP can be inserted into an unessential region of a dsRP, such as but not limited to the Pst I restriction endonuclease site in the cDNA clone of M segment [17]. Alternatively, standard PCR techniques can be used to introduce restriction endonuclease digestion sites in a non-essential region, such as between the pac sequence in segment-M and gene-10 in Phi-6 [17].

Alternatively, the sequence that is being incorporated into the dsRP can replace genes of the dsRP that are not required for the production of stable nucleocapsids, such as but not limited to the replacement of gene-10 in segment-M, gene-3 in segment-M, gene-9 in segment-S, gene-12 in segment-S; alternatively the sequence being inserted into the dsRP. Thus, plasmid pLM656 (From Dr. L Mindich, Department of Microbiology, The Public Health Research Institute NY, N.Y.; [17]), carries the complete cDNA copy of segment-M, is digested with RE Pst I and the resultant linear plasmid DNA is treated with T4 DNA polymerase to remove the single stranded sequences created by Pst I thereby creating blunt-ends.

Sequences of interest can be inserted into Pst I-digested, T4 polymerase-treated pLM656 DNA by standard blunt-end ligation techniques using T4 DNA ligase (Ausubel et al, supra; and Sambrook supra). The resultant plasmid carries a cDNA copy of the recombinant segment M produce mRNA's that carry the sequence of interest.

Introduction of Functional Eukaryotic Translation Expression Cassettes into dsRP As indicated above, in one embodiment of the current invention, sequences of interest can encode a functional eukaryotic translation expression cassette. A simple approach to obtain a functional eukaryotic translation expression cassette is to introduce an IRES functionally linked to a gene of interest (herein referred to as GOI), which is normally placed downstream (i.e. 3') of the IRES.

Sequences encoding the IRES can be amplified by PCR using primers specific for the 5' and 3' ends of the IRES sequence; the GOI can be amplified using primers specific for the 5' and 3' ends of the transcribed region of the GOI or parts thereof. RE digestion sites (e.g. Not I, Eco RI, Sal I) can be introduced into the primers so that the resultant PCR-generated products can be digested with said REs and fused to a positive-selection allele (herein referred to as "PSA"), which can be amplified using PCR primers that place RE recognition sites (e.g. Not I) at the 5' and 3' ends of the PSA. The particular PSA used in the current invention is not critical thereto and can be the kan$^r$ allele in plasmid pUC18K1 [47]; the *Escherichia coli* asd allele in plasmid pYA292 (Galan, et al., *Gene* 94:29-35 (1990); Genbank accession no. V00262).

The resultant chimeric fragment encoding PSA::IRES::GOI is inserted into an restriction endonuclease (RE)-digested plasmid containing the target dsRP segment (e.g. insertion into the M-segment using Pst I-digested, T4 polymerase-treated pLM656 DNA and blunt-end ligation to the PSA::IRES::GOI sequence, as above (Ausubel et al, supra; and Sambrook, supra). The resultant plasmid, carries a cDNA copy of the recombinant segment and produces mRNA's that bear a PSA for maintenance of the recombinant segment in the rdsRP, a cap-independent translation recognition sequence (i.e. IRES) and an GOI reporter gene.

Generation of rdsRP

An application of the current invention entails the use of enriched or purified rdsRP for direct administration to eukaryotic cells or tissues. The particular dsRP is not critical to the present invention and includes but is not restricted to one of Phi-6 (Genbank accession no. M17461 (Segment-L), M17462 (Segment-M), M12921 (Segment-S)); Phi-8 (Genbank accession no. AF226851 (Segment-L), NC_003300 (Segment-M), AF226853 (Segment-S)); and Phi-13 (Genbank accession no. AF261668 (Segment-L), AF261668 (Segment-M), NC_003714 (Segment-S)) and are available from Dr. L. Mindich at Department of Microbiology, Public Health Research Institute, NY, N.Y.

DsRP phi-6 normally replicates in *Pseudomonas syringae [*5]; dsRP phi-8, phi-11, phi-12 and phi-13 replicate in *Escherichia coli* strain JM109 (American type tissue culture collection (herein "ATCC") # 53323) and O-antigen negative mutants of *Salmonella enterica serovar Typhimurium* (herein designated "*S. typhimurium*") [5,14-16].

Alternatively, the cDNA sequences encoding the dsRP can be generated synthetically using an Applied Biosystems ABI™ 3900 High-Throughput DNA Synthesizer (Foster City, Calif. 94404 U.S.A.) and procedures provided by the manufacturer. To synthesize the cDNA copies of segments L, M and S a series of segments of the full-length sequence are generated by PCR and ligated together to form the full-length segment using procedures well know in the art [41-43]. Briefly, synthetic oligonucleotides 100-200 nucleotides in length (i.e. preferably with sequences at the 5'- and 3' ends that match at the 5' and 3' ends of the oligonucleotides that encodes the adjacent sequence) are produced using an automated DNA synthesizer (E.g. Applied Biosystems ABI™ 3900 High-Throughput DNA Synthesizer (Foster City, Calif. 94404 U.S.A.)). Using the same approach, the complement oligonucleotides are synthesized and annealed with the complementary partners to form double stranded oligonucleotides. Pairs of double stranded oligonucleotides (i.e. those that encode adjacent sequences) and joined by ligation to form a larger fragment. These larger fragments are purified by agarose gel electrophoresis and isolated using a gel purification kit (E.g. The QIAEX® II Gel Extraction System, from Qiagen, Santa Cruz, Calif., Cat. No. 12385). This procedure is repeated until the full-length DNA molecule is created. After each round of ligation the fragments can be amplified by PCR to increase the yield. Procedures for de novo synthetic gene construction are well known in the art, and are described elsewhere (Andre et al., supra, (1998); et al., Haas supra, (1996)); alternatively synthetic genes can be purchased commercially, e.g. from the Midland Certified Reagent Co. (Midland, Tex.).

To genetically manipulate dsRP, phages are amplified in a bacterial host strain, including but not limited to *Pseudomonas syringae [*5], *Escherichia coli* strain JM109 (American type tissue culture collection (herein "ATCC") # 53323) and O-antigen negative mutants of *Salmonella enterica serovar Typhimurium* (herein designated "*S. typhimurium*") [5,14-16]. and purified to the level commensurate to the desired in vitro or in vivo application. RdsRP are produced from strains carrying the plasmids that encode the cDNA copies of the manipulated segments (i.e. the segments containing the inserted sequences of interest encoding the functional eukaryotic translation expression cassette, catalytic RNA or antisense RNA).

To produce rdsRP in *Escherichia coli* (e.g. strain JM109), the cDNA-containing plasmids (e.g. pLM656-PSA::IRES::EGFP) are introduced into target bacterial strains by standard bacterial transformation methods (Ausubel et. al, supra; and Sambrook supra) and antibiotic-resistant transformants are isolated in solid media (e.g. Luria-Bertani agar (herein referred to as LBA), Difco Detroit Mich.) containing the appropriate antibiotic (Antibiotics for inclusion in bacteriological media are available from Sigma, St. Louis Mo.) at a concentration that is equal to, or greater than, the minimal inhibitory concentration (also referred to as the "mic").

The bacterial isolates are cultured at temperatures that range from 25° C. to 44° C. for 16 to 48 hr; however, it is preferable to culture the transformants at 37° C. for 16 hr. Colonies that grow on the selective solid media are subsequently isolated and purified by standard methods (Ausubel et al, supra; and Sambrook supra). To verify that the antibiotic-resistant isolates carrying the plasmid of interest, individual isolates are cultured in liquid media (e.g. Luria-Bertani broth (herein referred to as "LB"), Difco Mo.). The transformants are harvested after cultures reach an optical density at 600 nm ($OD_{600}$) of 0.001 to 4.0, preferably 0.9, relative to the $OD_{600}$ a sterile LB control. Plasmid DNA is isolated from these cultures and analysed by RE digestion using enzymes that generate a defined digestion pattern based on the predicted sequence of the recombinant plasmid, including but not limited to Eco RI, Pst L Hind III, Hae I, Sau IIIa, Not I and Sal I.

Alternatively or in addition, the plasmids can be screened by PCR using primers that amplify defined fragments within the recombinant plasmid, including but not limited to PCR primers that amplify the dsRP segment, the PSA, the IRES and the GOI. The PCR primers for the amplifications are designed using Clone Manager® software version 4.1 (Scientific and Educational Software Inc., Durhan N.C.). This software enables the design PCR primers and identifies RE sites that are compatible with the specific DNA fragments being manipulated. PCRs are conducted in a Strategene Robocycler, model 400880 (Strategene) and primer annealing, elongation and denaturation times in the PCRs are set according to standard procedures (Ausubel et al, supra). The RE digestions and the PCRs are subsequently analyzed by agarose gel electrophoresis using standard procedures (Ausubel et al, supra; and Sambrook, supra). A positive clone is defined as one that displays the appropriate RE pattern and/or PCR pattern. Plasmids identified through this procedure can be further evaluated using standard DNA sequencing procedures, as described above.

Having identified the desired transformants, individual strains are stored in a storage media, which is LB containing 50% (v/v) glycerol; Bacterial isolates are harvested from solid media using a sterile cotton wool swab and suspended in storage media at a density of $10^9$ cfu/ml and the suspensions are stored at −80° C.

Isolation and Purification of rdsRP

Batches of rdsRP are generated by replicating a parent rdsRP in the bacterial transformant said expresses the recombinant segment as shown in FIG. 4. Methods for incorporation of recombinant segments into dsRP and for the subsequent replication, isolation and purification of the resultant rdsRP are well known in the art and have been published extensively in detail elsewhere (Mindich, et al. *J Virol* 66, 2605-10 (1992); Mindich, et al. *Virology* 212:213-217 (1995); Mindich, et al., *J Bacteriol* 181:4505-4508 (1999); Qiao, et al., *Virology* 275:218-224 (2000); Qiao, et al., *Virology* 227:103-110 (1997); Olkkonen, et al., *Proc Natl Acad Sci USA* 87:9173-9177 (1990); Onodera, et al., *J Virol* 66, 190-196 (1992)).

Development of rdsRP that Express an Adjuvant

Recombinant dsRP can be constructed that encode an immunogen and an adjuvant, and can be used to increase host responses to the dsRP. Alternatively, recombinant dsRP can be constructed that encode an adjuvant, in mixtures with other dsRP to increase host responses to immunogens encoded by the partner rdsRP.

The particular adjuvant encoded by the rdsRP is not critical to the present invention and may be the A subunit of cholera toxin (i.e. CtxA; GenBank accession no. X00171, AF175708, D30053, D30052,), or parts thereof (E.g. the A1 domain of the A subunit of Ctx (i.e. CtxA1; GenBank accession no. K02679)), from any classical *Vibrio cholerae* (E.g. *V. cholerae* strain 395, ATCC # 39541) or El Tor *V. cholerae* (E.g. *V. cholerae* strain 2125, ATCC # 39050) strain. Alternatively, any bacterial toxin that increases cellular cAMP levels, such as a member of the family of bacterial adenosine diphosphate-ribosylating exotoxins (Krueger and Barbier, Clin. Microbiol. Rev., 8:34 (1995)), may be used in place of CtxA, for example the A subunit of heat-labile toxin (referred to herein as EltA) of enterotoxigenic *Escherichia coli* (GenBank accession # M35581), pertussis toxin S1 subunit (E.g. ptxS1, GenBank accession # AJ007364, AJ007363, AJ006159, AJ006157, etc.); as a further alternative the adjuvant may be one of the adenylate cyclase-hemolysins of *Bordetella pertussis* (ATCC # 8467), *Bordetella bronchiseptica* (ATCC # 7773) or *Bordetella parapertussis* (ATCC # 15237), E.g. the cyaA genes of *B. pertussis* (GenBank accession no. X14199), *B. parapertussis* (GenBank accession no. AJ249835) or *B. bronchiseptica* (GenBank accession no. Z37112).

Alternatively, the particular the adjuvant may be devoid of ADP-ribosyltransferase activity and may be any derivative of the A subunit of cholera toxin (i.e. CtxA, GenBank accession no. X00171, AF175708, D30053, D30052), or parts thereof (i.e. the A1 domain of the A subunit of Ctx (i.e. CtxA1; GenBank accession no. K02679)), from any classical *Vibrio cholerae* (E.g. *V. cholerae* strain 395, ATCC # 39541) or El Tor *V. cholerae* (E.g. *V. cholerae* strain 2125, ATCC # 39050) that lack ADP-ribosyltransferase catalytic activity but retain the structural integrity, including but not restricted to replacement of arginine-7 with lysine (herein referred to as “R7K”), serine-61 with lysine (S61K), serine-63 with lysine (S63K), valine-53 with aspartic acid (V53D), valine-97 with lysine (V97K) or tyrosine-104 with lysine (Y104K), or combinations thereof. Alternatively, the particular ADP-ribosyltransferase toxin that is devoid of ADP-ribosyltransferase activity may be any derivative of cholera toxin that fully assemble, but are nontoxic proteins due to mutations in the catalytic-site, or adjacent to the catalytic site, respectively. Such mutants are made by conventional site-directed mutagenesis procedures, as described above.

As a further alternative, the adjuvant of ADP-ribosyltransferase activity may be any derivative of the A subunit of heat-labile toxin (referred to herein as “LTA” of enterotoxigenic *Escherichia coli* (GenBank accession # M35581) isolated from any enterotoxigenic *Escherichia coli*, including but not restricted to *E. coli* strain H10407 (ATCC # 35401) that lack ADP-ribosyltransferase catalytic activity but retain the structural integrity, including but not restricted to R7K, S61K, S63K, V53D, V97K or Y104K, or combinations thereof. Alternatively, the particular ADP-ribosyltransferase toxin that is devoid of ADP-ribosyltransferase activity may be any derivative of cholera toxin that fully assemble, but are nontoxic proteins due to mutations in the catalytic-site, or adjacent to the catalytic site, respectively. Such mutants are made by conventional site-directed mutagenesis procedures, as described above.

Development of dsRP that Express an Immunoregulatory Agent

Recombinant dsRP can be constructed that encode an immunogen and a cytokine, and can be used to increase host responses to the dsRP. Alternatively, recombinant dsRP can be constructed that encode said cytokine alone, in mixtures with other dsRP to increase host responses to immunogens encoded by the partner rdsRP.

The particular cytokine encoded by the rdsRP is not critical to the present invention includes, but not limited to, interleukin-4 (herein referred to as “IL-4”; Genbank accession no. AF352783 (Murine IL-4) or NM_000589 (Human IL-4)), IL-5 (Genbank accession no. NM_010558 (Murine IL-5) or NM_000879 (Human IL-5)), IL-6 (Genbank accession no. M20572 (Murine IL-6) or M29150 (Human IL-6)), IL-10 (Genbank accession no. NM_010548 Murine IL-10) or AF418271 (Human IL-10)), $Il\text{-}12_{p40}$ (Genbank accession no. NM_008352 (Murine $IL\text{-}12_{p40}$) or AY008847 (Human IL-12 p40)), $IL\text{-}12_{p70}$ (Genbank accession no. NM_008351/NM_008352 (Murine IL-12 p35/40) or AF093065/AY008847 (Human IL-12 p35/40)), TGFβ (Genbank accession no. NM_011577 (Murine TGFβ1) or M60316 (Human TGFβ1)), and TNFα Genbank accession no. X02611 (Murine TNFα) or M26331 (Human TNFα)).

Recombinant DNA and RNA procedures for the introduction of functional eukaryotic translation expression cassettes to generate rdsRP capable of expressing an immunoregulatory agent in eukaryotic cells or tissues are described above, wherein said immunoregulatory agent is the GOI.

Development of Self-Amplifying dsRP

RdsRP can be constructed that carry an alpha-virus self-amplifying expression system (Pushko, et al., Virology 239: 389-401 (1997); Caley, et al. J Virol 71:3031-3038 (1997); Mossman, et al., J Virol 70, 1953-1960 (1996); Zhou, et al., Vaccine 12:1510-1514 (1994)) and are used to significantly elevate the expression of the GOI. The particular alpha-virus self-amplifying expression system is not critical to the present invention and can be selected from semliki forest virus, such as but not limited to the semliki forest virus replicon in commercially available plasmid pSFV1 from Invitrogen Inc., or sequences encoding the nonstructural protein precursor and replicase recognition sequences of Venezuela equine encephalitis virus (i.e Genbank accession no. L04653).

Recombinant DNA, PCR, RE and sequence analysis procedures for the introduction of functional eukaryotic translation expression cassettes into rdsRP that incorporates an alpha-virus self-amplifying expression system capable functionally linked to an immunogen, immunoregulatory agent, or therapeutic agent, are described above, wherein said immunoregulatory agent constitutes part of the GOI and the immunogen, immunoregulatory agent or therapeutic agent are placed downstream of the replicase recognition sequence (Genbank accession no. L04653), as described (Pushko, et al., Virology 239:389-401 (1997); Caley, et al. J Virol 71:3031-3038 (1997); Mossman, et al., J Virol 70, 1953-1960 (1996); Zhou, et al., Vaccine 12:1510-1514 (1994)).

Administration of rdsRP to Dendritic Cells In Vitro

The present invention can be used in vaccination regimens, wherein human derived dendritic cells are pulsed with the rdsRP and subsequently injected into an animal, intravenously, subcutaneously or intramuscularly. Such in vitro vaccination protocols are useful for the induction of anti-tumor immune responses Methods for the production and culture of dendritic cells (DC) are well known in the art and described elsewhere (Sallusto et al. 1994)). In short, human PBMCs are separated from the blood of healthy donors by centrifugation in Histopaque 1077 (Sigma, St. Louis, Mo.). The cells are enriched for monocytes (90-95% pure) using the StemSep Monocyte Enrichment Cocktail and a magnetic negative-selection column protocol (StemSep, Vancouver, British Columbia). Following enrichment, the monocytes are plated in RPMI 1640 (Gibco BRL: Grand Island, N.Y.) and incubated for 2 hours at 37 C in a 5% $CO_2$ (37° C./5% $CO_2$). Non-adherent cells and media are removed and replaced with complete DC media, which comprises of RPMI 1640 supplemented with 10% fetal bovine serum (Gibco-BRL), 1% sodium pyruvate (Sigma), 1% non-essential amino acids (Gibco-BRL), Gentamycin (Gibco-BRL), 50 μM β-mecaptoethanal (Sigma), 10 μM Hepes (Sigma), 35 ng/ml interleukin-4 (L4, R+D Systems, Minnesota, Minn.), and 50 ng/ml granulocyte/monocyte-colony stimulating factor (GM-CSF, R+D Systems). Cells develop the appearance and cell surface phenotype of immature MDDCs after 4 days in culture at 37 C 5% $CO_2$ environment, as confirmed by microscopy.

The DCs are analysed by flow cytometry at various times during the procedure to ensure that the appropriate antigen presenting properties are activated. The DCs are harvested in phosphate buffered saline (Gibco-BRL) supplemented with 2% human AB serum (Sigma) and 0.1% azide (Sigma), stained with R-phycoerythrin (PE)-anti-CD80, FITC-anti-CD83, PE-anti-CD86, PE-anti-CD25, PE-anti-HLA-ABC, and PE-anti-HLA-DR, (Becton Dickerson Pharmingen: San Deigo, Calif.) and fixed in 2% paraformaldehyde (Sigma) in PBS. Single-label flow cytometry data are collected using a FACSCaliber® (Beckmon Dickerson); expression of maturation markers in large cells is analyzed using CellQuest® (Beckmon Dickerson) and FlowJo® software (TreeStar, Stanford, Calif.).

To assess the cytokines produced by the DCs, Semi-quantitative ELISA assays for IL-6, TNF-α, IL-10, IL-12 p40, and IL-12 p70 (R+D Systems) were performed according to manufacturers instructions. In those experiments where cell surface data was not acquired, the cells and supernatants were frozen at −20° C. in the wells in which they were plated. The cells and supernatants were thawed and spun at 2000 RPM for 15 minutes to remove particulate matter immediately before ELISA assays were performed. In other experiments, the cell supernatants were reserved and either incorporated immediately into the ELISA protocol or frozen at −20° C.

Formulation of rdsRP Vaccines for In Vivo Administration

The specific method used to formulate the novel rdsRP vaccines described herein is not critical to the present invention and can be selected from a physiological buffer (Felgner et al., U.S. Pat. No. 5,589,466 (1996)); aluminum phosphate or aluminum hydroxyphosphate (e.g. Ulmer et al., Vaccine, 18:18 (2000)), monophosphoryl-lipid A (also referred to as MPL or MPLA; Schneerson et al. J. Immunol., 147: 2136-2140 (1991); e.g. Sasaki et al. Inf. Immunol., 65: 3520-3528 (1997); Lodmell et al. Vaccine, 18: 1059-1066 (2000)), QS-21 saponin (e.g. Sasaki, et al., J. Virol., 72:4931 (1998); dexamethasone (e.g. Malone, et al., J. Biol. Chem. 269:29903 (1994); CpG DNA sequences (Davis et al., J. Immunol., 15:870 (1998); or lipopolysaccharide (LPS) antagonist (Hone et al., supra (1997)).

Administration of rdsRP

The rdsRP vaccine can be administered directly into animal tissues by intravenous, intramuscular, intradermal, intraperitoneally, intranasal and oral inoculation routes. The specific method used to introduce the rdsRP vaccines described herein into the target animal tissue is not critical to the present invention and can be selected from previously described vaccination procedures (Wolff, et al., *Biotechniques* 11:474-85 (1991); Johnston and Tang, Methods Cell Biol 43:353-365 (1994); Yang and Sun, *Nat Med* 1:481-483 (1995); Qiu, et al., Gene Ther. 3:262-8 (1996); Larsen, et al., *J. Virol.* 72:1704-8 (1998); Shata and Hone *J. Virol.* 75:9665-9670 (2001); Shata, et al., *Vaccine* 20:623-629 (2001); Ogra, et al., *J Virol* 71:3031-3038 (1997); Buge, et al., *J. Virol.* 71:8531-8541 (1997); Belyakov, et al., *Nat. Med.* 7, 1320-1326 (2001); Lambert, et al., *Vaccine* 19:3033-3042 (2001); Kaneko, et al. *Virology* 267: 8-16 (2000); Belyakov, et al., *Proc Natl Acad Sci USA* 96:4512-4517 (1999).

Oral Administration of rdsRP with Bacterial Vaccine Vectors

Oral vaccination of the target animal with the rdsRP of the present invention can also be achieved using a non-pathogenic or attenuated bacterial vaccine vector. The amount of the bacterial vaccine vector to be administered with the rdsRP of the present invention will vary depending on the species of the subject, as well as the disease or condition that is being treated. Generally, the dosage employed will be about $10^3$ to $10^{11}$ viable organisms, preferably about $10^5$ to $10^9$ viable organisms.

The bacterial DNA vaccine vector and the rdsRP are generally administered along with a pharmaceutically acceptable carrier or diluent. The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al, *J. Clin. Invest.*, 79:888-902 (1987); and Black et al *J. Infect. Dis.*, 155:1260-1265 (1987)), or bicarbonate buffer (pH 7.0) containing ascorbic acid, lactose, and optionally aspartame (Levine et al, *Lancet, II:*467-470 (1988)). Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10% (w/v).

The following examples are provided for illustrative purposes only, and are in no way intended to limit the scope of the present invention.

EXAMPLE 1

Recombinant DNA Procedures

Restriction endonucleases (herein "Res"); New England Biolabs Beverly, Mass.), T4 DNA ligase (New England Biolabs, Beverly, Mass.) and Taq polymerase (Life technologies, Gaithersburg, Md.) were used according to the manufacturers' protocols; Plasmid DNA was prepared using small-scale (Qiagen Miniprep$^R$ kit, Santa Clarita, Calif.) or large-scale (Qiagen Maxiprep$^R$ kit, Santa Clarita, Calif.) plasmids DNA purification kits according to the manufacturer's protocols (Qiagen, Santa Clarita, Calif.); Nuclease-free, molecular biology grade milli-Q water, Tris-HCl (pH 7.5), EDTA pH 8.0, 1M $MgCl_2$, 100% (v/v) ethanol, ultra-pure agarose, and agarose gel electrophoresis buffer were purchased from Life technologies, Gaithersburg, Md. Restriction endonuclease RE digestions, PCRs, DNA ligation reactions and agarose gel electrophoresis were conducted according to well-known procedures (Sambrook et al., supra (1989); (Ausubel, et al., supra (1990)).

Nucleotide sequencing to verify the DNA sequence of each recombinant plasmid described in the following examples was accomplished by conventional automated DNA sequencing techniques using an Applied Biosystems automated sequencer, model 373A.

PCR primers were purchased from the University of Maryland Biopolymer Facility (Baltimore, Md.) and were synthesized using an Applied Biosystems DNA synthesizer (model 373A). PCR primers were used at a concentration of 200 μM and annealing temperatures for the PCR reactions were determined using Clone manager software version 4.1 (Scientific and Educational Software Inc., Durhan N.C.). PCRs were conducted in a Strategene Robocycler, model 400880 (Strategene, La Jolla, Calif.). The PCR primers for the amplifications are designed using Clone Manager® software version 4.1 (Scientific and Educational Software Inc., Durhan N.C.). This software enabled the design PCR primers and identifies RE sites that were compatible with the specific DNA fragments being manipulated. PCRs were conducted in a Strategene Robocycler, model 400880 (Strategene) and primer annealing, elongation and denaturation times in the PCRs were set according to standard procedures (Ausubel et al, supra). The RE digestions and the PCRs were subsequently analyzed by agarose gel electrophoresis using standard procedures (Ausubel et al, supra; and Sambrook, supra). A positive clone is defined as one that displays the appropriate RE pattern and/or PCR pattern. Plasmids identified through this procedure can be further evaluated using standard DNA sequencing procedures, as described above.

*Escherichia coli* strain Sable2$^R$ was purchased from Life Technologies (Bethesda, Md.) and served as initial host of the recombinant plasmids described in the examples below. Recombinant plasmids were introduced into *E. coli* strain Stable2$^R$ by electroporation using a Gene Pulser (BioRad Laboratories, Hercules, Calif.) set at 200Ω, 25 μF and 2.5 kV, as described (Ausubel et al, supra).

Bacterial strains were grown on tryptic soy agar (Difco, Detroit Mich.) or in tryptic soy broth (Difco, Detroit Mich.), which were made according to the manufacturer's directions. Unless stated otherwise, all bacteria were grown at 37° C. When appropriate, the media were supplemented with 100-μg/ml ampicillin (Sigma, St. Louis, Mo.). Bacterial strains were stored at −80° C. suspended in tryptic soy broth (Difco) containing 30% (v/v) glycerol (v/v; Sigma, St Louis Mo.) at ca. $10^9$ colony-forming units (herein referred to as "cfu") per ml.

EXAMPLE 2

Construction of a Prototype HIV-1 gp120 rdsRP Nucleocapsid

Figure 5:
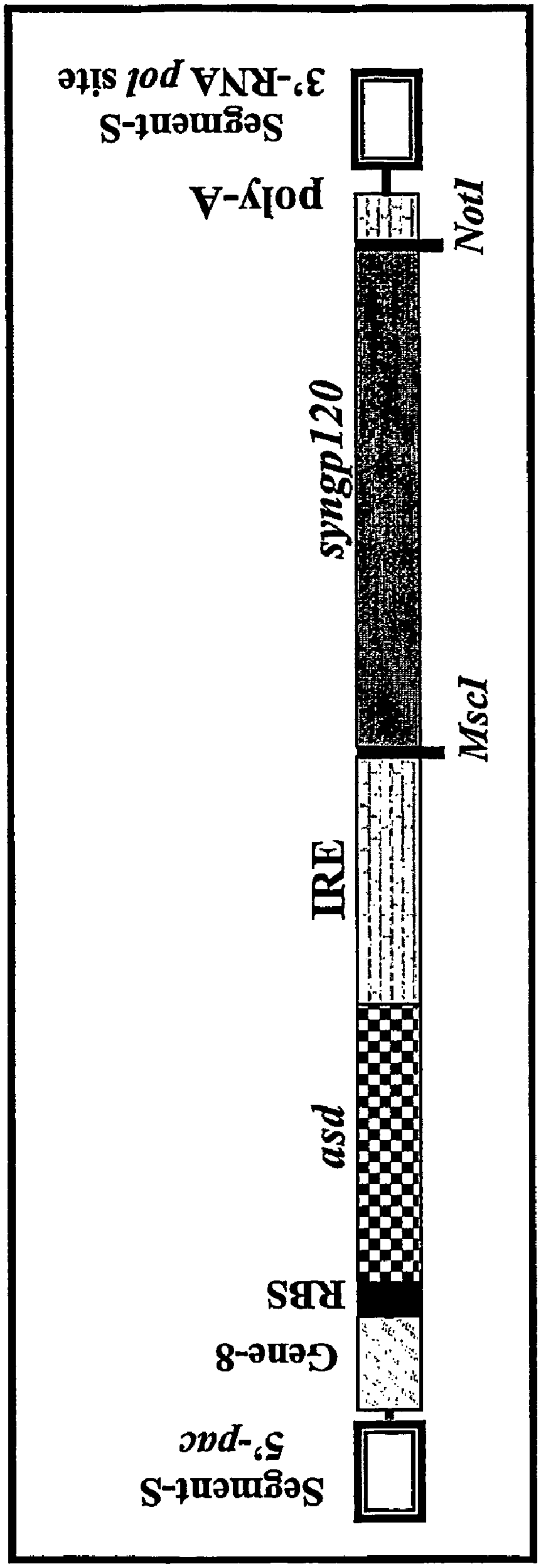
FIG. 5 illustrates a schematic representation of rdsRP-1 segment-S.

A functional eukaryotic translation expression cassette is obtained by incorporating an IRES that is functionally linked to the immunogen, the latter being placed immediately downstream of the IRES. Expression vector, designated "prϕ8Seg-S", carries the ϕ-8 segment-S pac sequence and gene-8, a positive selection allele, the encephalomyocarditis virus IRES [48], multiple cloning sites, a poly-adenylation sequence and ϕ-8 segment-S 3'-prime RNA-dependent RNA polymerase recognition sequence, as shown in FIG. 5. The blunt-end MscI site serves as an insertion point for any desired gene, such as those outlined in the detailed description of this invention above. Note that genes 5, 9 and 12 are omitted in the resultant rdsRP, as these genes are not required for nucleocapsid production [15,20]. In addition, ϕ-8 segment-M is not utilizes, as it is not required for nucleocapsid production and maintenance [15,20].

The components of plasmid prϕ8Seg-S are assembled by joining the sequences obtained from the following sources:

The ϕ-8 segment-S pac sequence and gene-8 ([15]; Genbank accession # AF226853) are obtained by PCR from plasmid pLM2755 (kindly provided by Dr. Leonard Mindich, Department of Microbiology, Public Health Research Institute, NY, N.Y.

A PSA encoding the *Escherichia coli* asd allele (Genbank accession no. V00262) for maintenance of the recombinant segment-S in the resultant rdsRP during propagation in *Escherichia coli [*15] is obtained by PCR from plasmid pYA292 [49].

The encephalomyocarditis virus IRES is obtained from pCITE4a by PCR, as described [50,51].

The 3-prime primer for this amplification encodes oning sites including MscI, EcoRI, SalI and NotI restriction endonuclease (RE) sites 3-prime to the IRES sequence (MscI is a blunt-end RE and provides an ATG start codon that is functionally linked to the IRES) and the bovine poly-adenylation sequence (obtained from pcDNA3.1 (Invitrogen)).

Similarly, the ϕ-8 segment-S RNA-dependent RNA polymerase recognition sequence is amplified from pLM2755 [15] by PCR.

The rdsRP is assembled using a sequential assembly procedure similar to the procedure used to assemble synthetic genes [52]. Thus, PCR-generated ϕ-8 segment-S pac sequence and gene-8 fragment is joined by T4 DNA ligase to the PCR-generated *E. coli* asd allele. This fusion fragment is amplified by PCR using primers specific for the 5-prime and 3-prime ends. Similarly, the PCR-generated encephalomyocarditis virus IRES::RE sites::poly-A fragment is joined by T4 DNA ligase to the PCR-generated ϕ-8 segment-S RNA-dependent RNA polymerase recognition sequence and the resultant fusion fragment is amplified by PCR using primers specific for the 5-prime and 3-prime ends of the fusion fragment. The two fusion fragments are then joined by ligation and amplified by PCR as above. This fragment is then inserted into the SmaI site in broad host range expression vector pBAD (Invitrogen, Carlsbad Calif.), which places the expression of the recombinant segment-S under the tight control of the L-arabinose-inducible *E. coli* araBAD promoter ($P_{BAD}$). The resultant plasmid, designated "prϕ8Seg-S" is isolated and purified as described in example 1.

An rdsRP capable of expressing HIV-1 gp120 in mammalian cells is constructed as follows. The sequence encoding syngp120 is obtained from pOGL1 by PCR so that MscI and NotI sites are created at the 5-prime and 3-prime ends of syngp120, respectively, as before [39]. The PCR-generated MscI::syngp120::NotI fragment is digested with MscI (New England Biolabs) and NotI (New England Biolabs) and inserted using T4 DNA ligase (New England Biolabs) into MscI-, NotI-digested prϕ8Seg-S, as shown in FIG. 5; this procedure functionally links syngp120 to the IRES. The resultant plasmid is designated prdsRP-1 and rdsRP that incorporate the recombinant segment-S expressed by prdsRP-1 (Example 7) bear the capacity to express gp120 in mammalians cells.

EXAMPLE 3

Construction of a rdsRP that Expresses A Conformationally Constrained HIV-1 Envelope Immunogen and Induces Broadly Neutralizing Antibodies to HIV-1

The advent of conformationally constrained HIV-1 envelope (Env) immunogens (i.e gp120-CD4 fusions herein referred to as "FLSC" [53] that induce antibodies capable of neutralizing a broad cross-section of primary HIV-1 isolates made it feasible to develop HIV-1 vaccination strategies that afford protection through humoral mechanisms. Therefore, a second-generation rdsRP vector is constructed by inserting sequences encoding FLSC [53] in place of syngp120 using procedures described in examples 1 and 2; the resultant rdsRP is designated "rdsRP-FLSC".

It is important to note that there is direct evidence linking humoral immune mechanisms to the prevention and control of HIV-1. In particular, data demonstrating that monoclonal and polyclonal neutralizing antibodies against IV-1 or SIV transfer protection against homologous challenge in animal models established direct evidence for protection through a humoral mechanism [54-65]. Nevertheless, reports describing the tertiary models of gp120 suggest that conserved epitopes exposed after binding to CD4, which are pivotal targets of broadly neutralizing antibodies, lie concealed within the core structure of unbound gp120. As a result, these key epitopes are poorly immunogenic in conventional Env, gp140 and gp120 subunit vaccines, which induce antibodies primarily to surface-exposed epitopes [66-72]. However, CD4-bound, conformationally constrained gp120 immunogens, such as FLSC [66-70] expose cryptic epitopes in gp120 that are normally only exposed following viral attachment to CD4 [66-70]. The availability of chemically and genetically stabilized conformationally constrained HIV-1 envelope (Env) immunogens (i.e FLSC), therefore, made it feasible to induce antibodies similar to those used in the above cited infusion studies that afford protection against HIV-1 [66-70]. Taken together, these observations indicate that immunization with rdsRP-FLSC has the potential to induce neutralizing antibodies against primary isolates of HIV-1 and provide protection against HIV-1 infection in humans.

EXAMPLE 4

Construction of an Anthrax rdsRP Vaccine

A functional eukaryotic translation expression cassette is obtained by incorporating an IRES that is functionally linked to the N-terminal region (i.e. amino acids 10 to 254) of *Bacillus anthrax* lethal factor (herein designated "tLF") by placing sequences encoding this immunogen downstream of the IRES in expression vector prϕ8Seg-S (Example 2). The sequence encoding tLF is obtained from pCLF4 ([73]; kindly provided by Dr. Darrell Galloway, Department of Micribiology, Ohio State University Ohio) by PCR so that MscI and NotI sites are created at the 5-prime and 3-prime ends, respectively (Example 1). The PCR-generated tLF fragment is digested with MscI (New England Biolabs) and NotI (New England Biolabs) and inserted, using T4 DNA ligase (New England Biolabs), into MscI-, NotI-digested prϕ8Seg-S, thereby functionally linking tLF to the IRES. The resultant plasmid is designated prdsRP-tLF and rdsRP that incorporate the recombinant segment-S expressed by prdsRP-tLF (Example 7) bear the capacity to express this non-toxic anthrax immunogen in mammalians cells. A second, functional eukaryotic translation expression cassette is obtained by incorporating an IRES that is functionally linked to the N-terminal region (i.e. amino acids 175 to 735) of *Bacillus* anthrax protective antigen (herein designated "tPA") by placing sequences encoding this immunogen [73] downstream of the IRES in expression vector prϕ8Seg-S (example 2). The sequence encoding tPA is obtained from pCPA ([73]; kindly provided by Dr. Darrell Galloway, Department of Micribiology, Ohio State University Ohio) by PCR so that MscI and NotI sites are created at the 5-prime and 3-prime ends, respectively (Example 1). The PCR-generated tPA fragment is digested with MscI (New England Biolabs) and NotI (New England Biolabs) and inserted, using T4 DNA ligase (New England Biolabs), into MscI-, NotI-digested prϕ8Seg-S, thereby functionally linking tPA to the IRES. The resultant plasmid is designated prdsRP-tPA and rdsRP that incorporate the recombinant segment-S expressed by prdsRP-tPA (Example 7) bear the capacity to express this anthrax immunogen in mammalians cells.

It is important to note that nucleic acid vaccines encoding tLF and tPA afforded protection in mice challenged intravenously with 5×50% lethal doses of *Bacillus* anthrax lethal toxin (PA plus LF) [73]. In this study, 100% of mice immunized with nucleic acid vaccine that expressed tLF alone, tPA alone, or the combination of both survived such a challenge, whereas all of the unvaccinated mice died [73]. Since neutralization of *Bacillus* anthrax toxin is a correlate of protection in humans, these results indicate that immunization with prdsRP-tLF and prdsRP-tPA alone or in combination has the potential to induce *Bacillus* anthrax neutralizing antibodies and provide protection against a lethal *Bacillus* anthrax toxin infection in humans.

EXAMPLE 5

Construction of a rdsRP that Expresses an Immunogen and an Adjuvant

As an additional parallel track, the immunogenicity of rdsRP-1 (Example 2) and rdsRP-2 (Example 6) can be enhanced significantly be including sequences that encode the catalytic domain of cholera toxin (herein referred to as "ctxA1"), which are incorporated into a recombinant segment-M in the rdsRP. To this end, a second PSA (i.e. the kanamycin-resistance gene herein designated "$kan^r$" from plasmid pUC18K1 [47] is inserted immediately downstream of the segment-M pac sequence, the latter being amplified from pLM2669, which encodes and expresses a full-length cDNA copy of ϕ-8 segment-M (kindly provided by Dr. Leonard Mindich). The CtxA1 gene functionally linked to the 53 bp hepatitis C virus IRES (Genebank accession no. 1KH6¯A; [45,46]) is then inserted downstream of $kan^R$ by blunt-end ligation. The 53 bp hepatitis C virus IRES is made synthetically (Example 1). Downstream of the ctxA1 gene, DNA sequences encoding a poly-adenylation site (from $pcDNA3.1_{ZEO}$; See Example 1) and the 3-prime RNA-dependent RNA polymerase recognition sequence are included (the latter is amplified from pLM2669).

EXAMPLE 6

Introduction of an Alphavirus Amplicon into the rdsRP System

Figure 6:
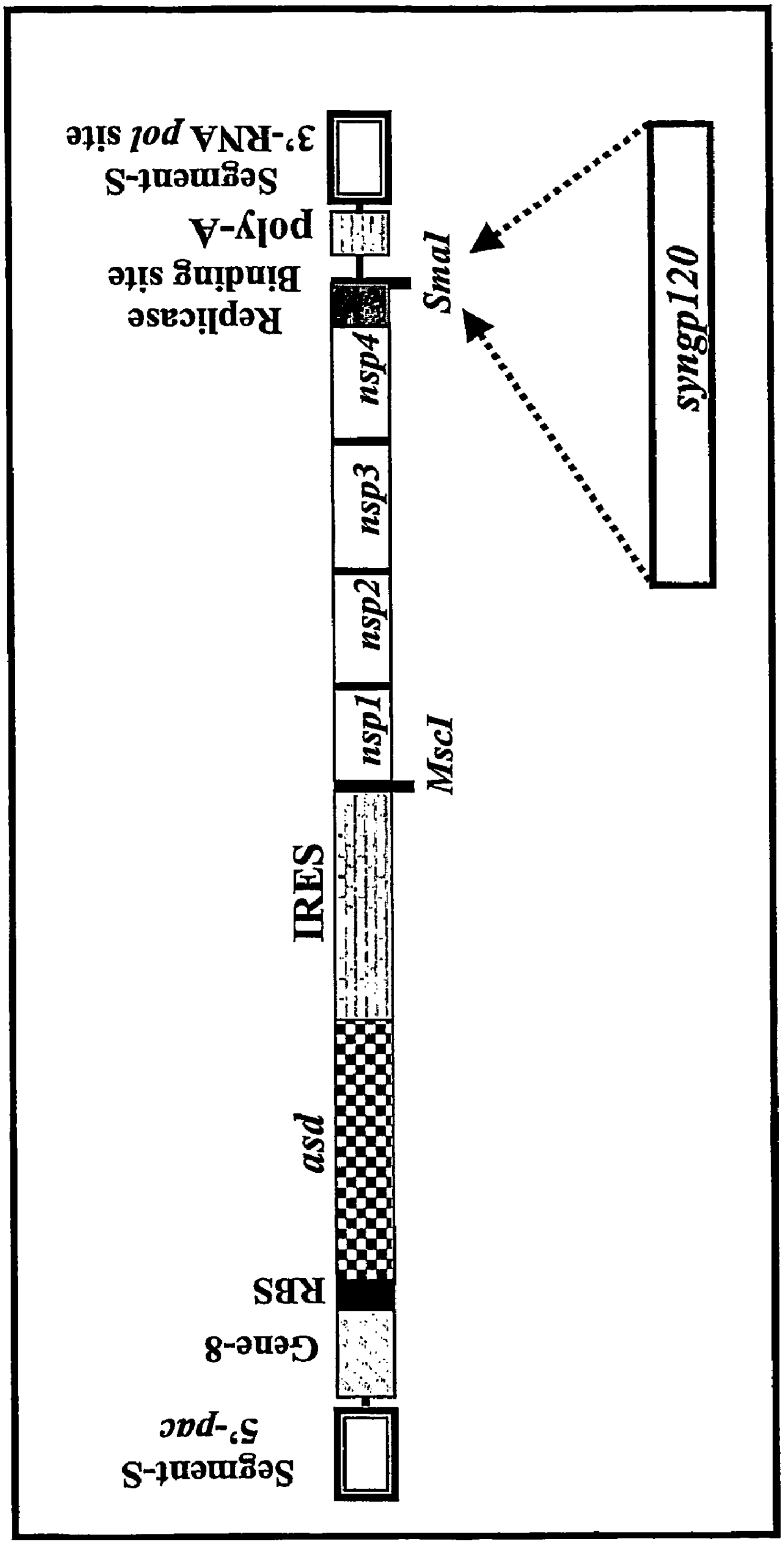
FIG. 6 illustrates an arrangement of a recombinant segment-S in a self-amplifying rdsRP.

As noted above, rdsRP can harbor a mammalian translation expression cassette comprised of Semliki Forest virus (herein referred to as "SFV") self-amplifying replicon from plasmid pSFV1 (Invitrogen Inc., Carlsbad Calif.) functionally linked to syngp120 or to FLSC (See Examples 1 and 2). Genes encoding SFV non-structural proteins (herein referred to as "NSPs" 14 and the replicase recognition site in pSFV1 are amplified by PCR and inserted by blunt-end ligation into the MscI site immediately downstream and functionally linked to the IRES in prϕ8Seg-S (Example 2), resulting in prϕ8Ampl-S as shown in FIG. 6. Incidentally, the SmaI RE site in plasmid prϕ8Ampl-S can serve as an insertion site for any desired gene, such as those outline above in the detailed description of the invention. In this instance, however, PCR-generated DNA encoding the syngp120 gene in pOGL1 (Example 1) is inserted into the SmaI site in prϕ8Ampl-S, which places it immediately downstream of, and functionally linked to, the SFV virus replicase recognition site (FIG. 6). RdsRP that harbor this recombinant segment-S are designated herein as rdsRP-2.

EXAMPLE 7

Generation, Isolation and Purification of rdsRP-1 and rdsRP-2

Batches of rdsRP-1 and rdsRP-2 are generated by replicating a parent dsRP on the bacterial transformant the carries the expression prdsRP-1 (i.e. expresses the 5'-pacS-gene-8::$P_{BAD}$-Ωasd::IRES:: syngp120::poly-A::3'-Seg-S recombinant segment-S; (wherein "::" indicates a novel nucleic acid junction; construction details are provided in Example 2) and prdsRP-2 (i.e. expresses the 5'-pacS-gene-8::$P_{BAD}$-Ωasd::IRES::$SFV_{nsp1-4}$::syngp120::poly-A::3'-Seg-S recombinant segment-S; Example 6), respectively (FIG. 4). Standard methods for incorporation of recombinant segments into dsRP and the subsequent replication, isolation and purification of the resultant rdsRP are used, as published in detail elsewhere [17,20,74,75] [14-16]. Briefly, rdsRP are generated in *Escherichia coli* strain JM109; recombinant plasmids prdsRP-1 and prdsRP-2 are introduced into *E. coli* Δasd mutant strain χ6212 by transformation [76] and ampicillin-resistant transformants are isolated on LBA containing 100 μg/ml ampicillin (Sigma).

The bacterial isolates are cultured at 37° C. for 24 hr; colonies that grow on the selective solid media are subsequently isolated and purified by standard methods [76]. To verify that the antibiotic-resistant isolates carrying the plasmid of interest, individual isolates are cultured in Luria-Bertani broth (LB; Difco, St Louis Mo.). The transformants are harvested after cultures reach an optical density at 600 nm ($OD_{600}$) of 0.9, relative to the $OD_{600}$ a sterile LB control. Plasmid DNA is isolated from these cultures and analyzed by RE digestion using those that generate a defined digestion pattern based on the predicted sequence of the recombinant plasmid, including EcoRI, PstI, HindIII, HaeI, SmaI, NotI, and SalI. In addition, the plasmids are screened by PCR using primers that amplify defined fragments within the recombinant segment-S including asd, IRES and syngp120. The PCR primers for the amplifications are designed as outlined in Example 1. The products of RE digestion and the PCR were analyzed by agarose gel electrophoresis [76]. A positive clone is defined as one that displays the appropriate RE pattern and PCR pattern. Plasmids identified through this procedure can be further evaluated using standard DNA sequencing procedures, as described (Example 1).

Finally, replication of parent dsRP ϕ-8 on χ6212 transformants that harbor the recombinant plasmids prdsRP-1 or pdsRP-3 generates the rdsRP designated rdsRP-1 and rdsRP-3, respectively. χ6212 carriers of rdsRP-1 and rdsRP-2 are isolated from within the resultant turbid plaques. These latter isolates are cultured on media lacking diaminopalmelic acid; under these circumstances only χ6212(rdsRP-1) and χ6212 (rdsRP-2) carriers are capable of growth due to complementation of the lethal Δasd mutation by the expression of the recombinant segments in the rdsRPs. Methods for isolation and purification of rdsRP nucleocapsids, entailing liquid culture of carrier strain χ6212(rdsRP-1) and χ6212(rdsRP-2), osmotic lysis of the χ6212(rdsRP-1) and χ6212(rdsRP-2) bacilli and sucrose density gradient purification of the rdsRP-1 and rdsRP-2 nucleocapsids, have been published extensively in detail by others [14-17,20,74,75]. Residual endotoxin is removed by adsorption to End-X® Endotoxin Affinity Resin (Cape Cod Associates Inc, Cape Cod Mass.). The purified rdsRP are placed into Spectrapore 50,000 Da cutoff dialysis tubing and dialyzed in phosphate buffered saline (PBS) pH 7.3. The number of plaque-forming units (pfu) in the nucleocapsid preparations is measured by infecting χ6212 protoplasts with 10-fold serial dilutions of each preparation and plating this suspension in soft-agar, as described [20]. The nucleocapsid concentration is adjusted to $5\times10^{10}$ pfu/ml.

EXAMPLE 8

Infection of Human Dendritic Cells in Vitro with rdsRP

DsRP nucleocapsids have the unusual property of being able to auto-transform bacterial protoplasts, a process that requires gene-8 [20,77]. Since the mechanism of protoplast transfection resembles that of mammalian cells, rdsRP have the capacity to enter and express passenger immunogens in vitro following treatment of human monocyte-derived dendritic cells (MDDCs) with the purified rdsRP. In short, human PBMCs are separated from the blood of healthy donors by centrifugation in Histopaque 1077 (Sigma, St. Louis, Mo.). The cells are enriched for monocytes (90-95% pure) using the StemSep® Monocyte Enrichment Cocktail and a magnetic negative-selection column (StemSep, Vancouver, British Columbia). Following enrichment, the monocytes are plated in RPMI 1640 (Gibco-BRL, Grand Island, N.Y.) and incubated for 2 hours at 37 C in a 5% $CO_2$ environment. Non-adherent cells and media are removed, and replaced with complete DC media, which comprises of RPMI 1640 supplemented with 10% fetal bovine serum (Gibco-BRL), 1% sodium pyruvate (Sigma), 1% non-essential amino acids (Gibco-BRL), Gentamycin (Gibco-BRL), 50 μM β-mecaptoethanal (Sigma), 10 μM Hepes (Sigma), 35 ng/ml interleukin-4 (IL-4, R&D Systems, Minnesota, Minn.), and 50 ng/ml granulocyte/monocyte-colony stimulating factor (GM-CSF, R&D Systems). The cells in such cultures develop the appearance and cell surface phenotype of immature MDDCs after 4 days in culture, as confirmed by microscopy and flow cytometry.

To evaluate the delivery and expression of gp120 encoded in rdsRP-1, MDDCs are treated with a range of doses (from $10^3$-$10^7$ pfu). Cells treated with the rdsRP vectors and the control cells are harvested after 24, 48 and 72 hr at 37° C. in 5% $CO_2$. The cells are washed twice with PBS and lysed in 1×SDS sample buffer and run on SDS-PAGE gels made with 5% to 15% gradients of polyacrylamide. The samples are run under non-reducing and reducing conditions to estimate the yields of oligomeric forms of gp160. The samples are transferred to PVDF membranes, which is probed with a mixture of monoclonal antibodies specific for defined epitopes of gp120 [66,78]. The extent of glycosylation of Env proteins is estimated by treatment with Endo-H prior to separation and evidence of glycosylation is taken as sine qua non that the gp120 RNA was expressed in the eukaryotic cell.

This experiment is designed to demonstrate that rdsRP-1 and rdsRP-2 bear an innate ability to enter mammalian cells and express gp120, wherein rdsRP-2 is capable of expressing significantly higher levels of gp120 that rdsRP-1 due to the incorporation of the SFV amplicon in rdsRP-2 (Example 6).

EXAMPLE 9

Immunogenicity of rdsRP Vaccine Vectors in Mice

Female BALB/c and C57B1/6 mice aged 6-8 weeks are obtained from Jackson Laboratories River (Bar Harbor, Me.). All mice are certified specific-pathogen free and upon arrival at the University of Maryland Biotechnology Institute Animal Facility are maintained in a microisolator environment and allowed to fee and drink ad lib.

The immunogenicity of rdsRP-1 (Example 2) and rdsRP-2 (Example 6) is assessed in groups of 10 mice, initially at dose of $10^9$ pfu. Both rdsRP-1 and rdsRP-2 are administered intragastrically three times spaced by 4-week intervals. In addition, a group of 10 mice is vaccinated intranasally with three $10^9$-pfu doses of rdsRP-1 and a second similar sized group of mice is vaccinated with rdsRP-2; in both instances the doses are spaced by 4-week intervals. In parallel, groups of 10 mice are vaccinated with a single $10^9$ pfu-dose of the rdsRP-1 or rdsRP-2, followed by two subcutaneous 50 μg-doses of soluble gp120 (or FLSC when appropriate). This enables the assessment of rdsRP-1 as a priming vaccine.

Fully glycosylated gp120 used in such boosts is purified from serum-free culture supernatants collected from 293 cells that are stably transfected with pOGL1 (Expresses HIV-$1_{MN}$ gp120) or pBaHu-120 (Expresses HIV-$1_{BaL1}$ gp120) and is supplied on a fee-for-service basis by the IHV μQuant core facility.

Additional groups of 10 mice are vaccinated intramuscularly with $10^3$ to $10^8$ rdsRP-1 or rdsRP-1 pfu (in 10-fold serial dilutions) suspended in endotoxin-free saline (0.85% (w/v) NaCl), by direct injection using a 30-gauge needle and a 1 ml tuberculin syringe. Booster vaccinations are given using the same formulation, route and dose as used to prime the mice, spaced by 4-week intervals.

The immune-priming properties of each construct is determined by sacrificing groups of 5 mice 28 days after vaccination and the numbers of gp120-specific antibody secreting and $CD4^+$ T cells are assessed as described in Example 10. The remaining 5 mice in each group are boosted as delineated above.

When rdsRP-1 and rdsRP-2 prove adept at delivering inducing humoral responses to the passenger immunogen, gp120, it will be possible to reduce the number of rdsRP-1 and rdsRP-2 dose. Thus, in the experimental protocol groups of 10 BALB/c mice that receive a single dose and two doses of each test rdsRP are included. These groups assess the effectiveness of both the prime and boosts in the extended three dose protocols.

When the boosts prove unnecessary, the immunogenicity of 3-fold serial dilutions of each rdsRP, from $1\times10^4$ to $1\times10^9$ pfu, are evaluated to determine whether the lower doses elicit immune responses to gp120 (See Example 10).

This series of vaccination experiments is designed to demonstrate that rdsRP-1 and rdsRP-2 bear an innate ability to induce immune responses to gp120 in mice vaccinated intragastrically, intranasally, and subcutaneously. Since rdsRP-2 is capable of expressing significantly higher levels of gp120 that rdsRP-1 due to the incorporation of the SFV amplicon in rdsRP-2 (Example 6), the immune responses in mice vaccinated with rdsRP-2 are generally stronger in magnitude.

EXAMPLE 10

Measurement of Immune Responses

To measure serum IgG and IgA responses to gp120, sera are collected before and at 10-day intervals after vaccination. About 400-500 μl of blood is collected into individual tubes from the tail vein of each mouse and allowed to clot by incubating for 4 hr on ice. After centrifugation in a microfuge for 5 min, the sera are transferred to fresh tubes and stored at −80° C. Mucosal IgG and IgA responses to gp120 are determined using fecal pellets and vaginal washes that are harvested before and 10-day intervals after vaccination [79,80].

Standard ELISAs are used to quantitate the IgG and IgA responses to gp120 in the sera and mucosal samples [78,81], and conducted as a fee-for-service by the IHV's Viral Immunology Core facility. Fully glycosylated gp120 for the ELISA assays is purified as described (example 9). The purified gp120 is suspended in PBS at a concentration of 3-10 μg/ml and will be used to coat 96-well ELISA plates. Ovalbumin is included in each ELISA as a negative control antigen and purified rdsRP nucleocapsids are included as a control antigen for vector immunogenicity. In addition, each ELISA also includes a positive control serum, fecal pellet or vaginal wash sample, when appropriate. The positive control samples are harvested from mice vaccinated intranasally with 10 μg gp120 mixed with 10 μg cholera toxin, as described [82]. The end-point titers are calculated by taking the inverse of the last serum dilution that produced an increase in the absorbance at 490 nm that is greater than the mean of the negative control row plus three standard error values.

When a vaccine construct induces high-titer serum IgG and IgA responses, the gp120-specific IgG and IgA responses are also measured in the mucosal compartment. Serum dimeric IgA is transported across mucosal surfaces in mice and it is difficult to distinguish between locally produced IgA and systemically produced serum IgA in the mucosal secretions. Therefore, a more direct measure of mucosal humoral immunity to gp120 is obtained by harvesting lamina propria lymphocytes from small intestinal, colonic and vaginal tissue 40 and 80 days after vaccination, using procedures that preserve lymphocyte function [38,83]. IgA-specific ELISPOT assays are conducted as described previously by our group previously [38,83] and the results are expressed as the number of gp120-specific IgA-producing cells per 10,000 IgA-producing cells [38].

When measuring the primary $CD4^+$ T cell immune responses after the first vaccination, groups of 5 mice are sacrificed 28 days after immunization, and Peyer's patch, lamina propria (mucosal sites) and spleen (systemic site) cells are harvested using standard procedures [38,83]. Single cell suspensions of enriched $CD4^+$ T cells from these tissues are used immediately to measure the magnitude of the gp120-specific $CD4^+$ T cell responses by cytokine-specific ELISPOT assay [38]. Each sample is stimulated with three doses (0.1, 1.0 and 10) μg/ml of gp120 and the numbers of gp120-specific $CD4^+$ T cells are determined by cytokine-specific ELISPOT assays for IL-2, IL-4, IL-5, IL-6, IL-10 and IFN-γ production. All ELISPOT assays are conducted using commercially-available capture and detection mAbs (R&D Systems and Pharmingen), as described [84,85]. Each assay includes mitogen (Con A) and ovalbumin controls.

EXAMPLE 11

Vaccination Protocol Discrimination Criteria

As indicated in example 10, the magnitude of humoral and $CD4^+$ T cell responses to the selected HIV-1 immunogens in mice vaccinated intragastrically and intranasally with the experimental rdsRP constructs are measured by conventional ELISA and ELISPOT assays. Individual immune response parameters are evaluated quantitatively with the idea of characterizing the magnitude and duration of the host responses that are generated by each construct. In addition, all experimental values are measured in triplicate and standard statistical analyses are used when measuring and comparing the individual responses (including ANOVA and Student T tests). To ensure reproducibility, each experiment is performed a minimum of two times. When appropriate, the number of mice can be increase in individual groups if trends are observed but there is insufficient statistical power to resolve the differences. The following set of criteria was formulated to enable one to discriminate between the rdsRP vaccination protocols in example 9:

"Go" Criteria:

The location of the response: Preference is assigned to vaccination protocols that elicit gp120-specific humoral responses in both mucosal and systemic sites.

The magnitude of the responses: Preference is assigned to vaccination protocol that elicits the strongest gp120-specific antibody and/or antibody secreting cell responses.

The duration of the response: Preference is assigned to vaccines that elicit responses that remain significantly elevated for the longest period after vaccination.

The minimum effective dose: Preference is assigned to vaccination protocols that achieve the immune responses above with the minimum dose of rdsRP and the fewest doses.

"No-Go" Criteria:

Vaccination protocols that fail to induce immune responses to the passenger immunogen.

When pertinent (i.e. when FLSC immunogens are inserted into the rdsRP instead of gp120), vaccination protocols that fail to induce broadly neutralizing antibodies to primary HIV-1 isolates.

While the invention has been described in detail, and with reference to specific embodiments thereof, it will be apparent to one of ordinary skill in the art that various changes and modifications can be made therein without departing from the spirit and scope thereof.

REFERENCES CITED IN TEXT

All cited references are hereby incorporated herein by reference for all purposes.

1 Sinclair, J. F., Tzagoloff, A., Levine, D. & Mindich, L. Proteins of bacteriophage phi6. *J Virol* 1975, 16(3), 685-695.

2 McGraw, T., Mindich, L. & Frangione, B. Nucleotide sequence of the small double-stranded RNA segment of bacteriophage phi 6: novel mechanism of natural translational control. *J Virol* 1986, 58(1), 142-151.

3 Gottlieb, P., Metzger, S., Romantschuk, M. et al. Nucleotide sequence of the middle dsRNA segment of bacteriophage phi 6: placement of the genes of membrane-associated proteins. *Virology* 1988, 163(1), 183-190.

4 Mindich, L., Nemhauser, I., Gottlieb, P. et al. Nucleotide sequence of the large double-stranded RNA segment of bacteriophage phi 6: genes specifying the viral replicase and transcriptase. *J Virol* 1988, 62(4), 1180-1185.

5 Mindich, L. Precise packaging of the three genomic segments of the double-RNA bacteriophage phi6. *Microbiol. Mol. Biol. Rev.* 1999, 63(1), 149-160.

6 Van Etten, J. L., Vidaver, A. K., Koski, R. K. & Burnett, J. P. Base composition and hybridization studies of the three double-stranded RNA segments of bacteriophage phi 6. *J Virol* 1974, 13(6), 1254-1262.

7 Sands, J. A. & Lowlicht, R. A. Temporal origin of viral phospholipids of the enveloped bacteriophage phi 6. *Can J Microbiol* 1976, 22(2), 154-158.

8 Bamford, D. H. & Palva, E. T. Structure of the lipid-containing bacteriophage phi 6. Disruption by Triton X-100 treatment. *Biochim Biophys Acta* 1980, 601(2), 245-259.

9 Berger, H. & Kennedy, K. Physical measurements on the lipid-containing bacteriophage phi 6. *Biochim Biophys Acta* 1980, 633(1), 68-76.

10 Olkkonen, V. M. & Bamford, D. H. The nucleocapsid of the lipid-containing double-stranded RNA bacteriophage phi 6 contains a protein skeleton consisting of a single polypeptide species. *J Virol* 1987, 61(8), 2362-2367.

11 Mindich, L. Bacteriophage phi 6: a unique virus having a lipid-containing membrane and a genome composed of three dsRNA segments. *Adv Virus Res* 1988, 35, 137-176.

12 Johnson, M. D., 3rd & Mindich, L. Plasmid-directed assembly of the lipid-containing membrane of bacteriophage phi 6. *J Bacteriol* 1994, 176(13), 4124-4132.

13 Van Etten, J. L., Vidaver, A. K., Koski, R. K. & Semancik, J. S. RNA polymerase activity associated with bacteriophage phi 6. *J Virol* 1973, 12(3), 464-471.

14 Mindich, L., Qiao, X., Qiao, J., Onodera, S., Romantschuk, M. & Hoogstraten, D. Isolation of additional bacteriophages with genomes of segmented double-stranded RNA. *J Bacteriol* 1999, 181(15), 4505-4508.

15 Hoogstraten, D., Qiao, X., Sun, Y., Hu, A., Onodera, S. & Mindich, L. Characterization of phi8, a bacteriophage containing three double-stranded RNA genomic segments and distantly related to Phi6. *Virology* 2000, 272(1), 218-224.

16 Qiao, X., Qiao, J., Onodera, S. & Mindich, L. Characterization of phi 13, a bacteriophage related to phi 6 and containing three dsRNA genomic segments. *Virology* 2000, 275(1), 218-224.

17 Onodera, S., Olkkonen, V. M., Gottlieb, P. et al. Construction of a transducing virus from double-stranded RNA bacteriophage phi6: establishment of carrier states in host cells. *J Virol* 1992, 66(1), 190-196.

18 Onodera, S., Qiao, X., Qiao, J. & Mindich, L. Directed changes in the number of double-stranded RNA genomic segments in bacteriophage phi6. *Proc Natl Acad Sci USA* 1998, 95(7), 3920-3924.

19 Qiao, X., Qiao, J. & Mindich, L. An in vitro system for the investigation of heterologous RNA recombination. *Virology* 1997, 227(1), 103-110.

20 Olkkonen, V. M., Gottlieb, P., Strassman, J., Qiao, X. Y., Bamford, D. H. & Mindich, L. In vitro assembly of infectious nucleocapsids of bacteriophage phi 6: formation of a recombinant double-stranded RNA virus. *Proc. Natl. Acad. Sci.* 1990, 87(23), 9173-9177.

21 Gottlieb, P., Strassman, J., Qiao, X. Y., Frucht, A. & Mindich, L. In vitro replication, packaging, and transcription of the segmented double-stranded RNA genome of bacteriophage phi 6: studies with procapsids assembled from plasmid-encoded proteins. *J Bacteriol* 1990, 172(10), 5774-5782.

22 Gottlieb, P., Strassman, J., Frucht, A., Qiao, X. Y. & Mindich, L. In vitro packaging of the bacteriophage phi 6 ssRNA genomic precursors. *Virology* 1991, 181(2), 589-594.

23 Gottlieb, P., Strassman, J., Qiao, X., Frilander, M., Frucht, A. & Mindich, L. In vitro packaging and replication of individual genomic segments of bacteriophage phi 6 RNA. *J Virol* 1992, 66(5), 2611-2616.

24 Qiao, X., Casini, G., Qiao, J. & Mindich, L. In vitro packaging of individual genomic segments of bacteriophage phi 6 RNA: serial dependence relationships. *J Virol* 1995, 69(5), 2926-2931.

25 Davis, N. L., Brown, K. W. & Johnston, R. E. A viral vaccine vector that expresses foreign genes in lymph nodes and protects against mucosal challenge. *J Virol* 1996, 70(6), 3781-3787.

26 Pushko, P., Parker, M., Ludwig, G. V., Davis, N. L., Johnston, R. E. & Smith, J. F. Replicon-helper systems from attenuated Venezuelan equine encephalitis virus: expression of heterologous genes in vitro and immunization against heterologous pathogens in vivo. Virology 1997, 239(2), 389-401.

27 Caley, I. J., Betts, M. R., Irlbeck, D. M. et al. Humoral, mucosal, and cellular immunity in response to a human immunodeficiency virus type 1 immunogen expressed by a Venezuelan equine encephalitis virus vaccine vector. *J Virol* 1997, 71(4), 3031-3038.

28 Balasuriya, U. B., Heidner, H. W., Davis, N. L. et al. Alphavirus replicon particles expressing the two major envelope proteins of equine arteritis virus induce high level protection against challenge with virulent virus in vaccinated horses. *Vaccine* 2002, 20(11-12), 1609-1617.

29 Zhou, X., Berglund, P., Rhodes, G., Parker, S. E., Jondal, M. & Liljestrom, P. Self-replicating Semliki Forest virus RNA as recombinant vaccine. *Vaccine* 1994, 12(16), 1510-1514.

30 Berglund, P., Fleeton, M. N., Smerdou, C. & Liljestrom, P. Immunization with recombinant Semliki Forest virus induces protection against influenza challenge in mice. *Vaccine* 1999, 17(5), 497-507.

31 Fleeton, M. N., Sheahan, B. J., Gould, E. A., Atkins, G. J. & Liljestrom, P. Recombinant Semliki Forest virus particles encoding the prME or NS1 proteins of louping ill virus protect mice from lethal challenge. *J Gen Virol* 1999, 80 (Pt 5), 1189-1198.

32 Phenix, K. V., Wark, K., Luke, C. J. et al. Recombinant Semliki Forest virus vector exhibits potential for avian virus vaccine development. *Vaccine* 2001, 19(23-24), 3116-3123.

33 Withoff, S., Glazenburg, K. L., van Veen, M. L. et al. Replication-defective recombinant Semliki Forest virus encoding GM-CSF as a vector system for rapid and facile generation of autologous human tumor cell vaccines. *Gene Ther* 2001, 8(20), 1515-1523.

34 Brinster, C., Chen, M., Boucreux, D. et al. Hepatitis C virus non-structural protein 3-specific cellular immune responses following single or combined immunization with DNA or recombinant Semliki Forest virus particles. *J Gen Virol* 2002, 83(Pt 2), 369-381.

35 Dalemans, W., Delers, A., Delmelle, C. et al. Protection against homologous influenza challenge by genetic immunization with SFV-RNA encoding Flu-HA. *Ann N Y Acad Sci* 1995, 772, 255-256.

36 Conry, R. M., LoBuglio, A. F., Wright, M. et al. Characterization of a messenger RNA polynucleotide vaccine vector. Cancer Res 1995, 55(7), 1397-1400.

37 Fouts, T. R., Lewis, G. K. & Hone, D. M. Construction and characterization of a *Salmonella typhi*-based human immunodeficiency virus type 1 vector vaccine. *Vaccine* 1995, 13(6), 561-569.

38 Wu, S., Pascual, D. W., Lewis, G. K. & Hone, D. M. Induction of mucosal and systemic responses against human immunodeficiency virus type 1 glycoprotein 120 in mice after oral immunization with a single dose of a *Salmonella*-HIV vector. *AIDS Res. Hum. Retrovir.* 1997, 13(14), 1187-1194.

39 Shata, M. T. & Hone, D. M. Vaccination of mice with a *Shigella*-gp120 DNA vaccine vector induces HIV-1 gp120-specific $CD8^+$ T cells and antiviral protective immunity. *J. Virol.* 2001, 75(20), 9665-9670.

40 Shata, M. T., Lewis, G. K. & Hone, D. M. Human Immunodeficiency Virus-1 envelope specific T cells elicited by oral vaccination with a *Salmonella*-gp160 DNA vaccine vector in mice. Vaccine 2001, 20, 623-629.

41 Haas, J., Park, E. C. & Seed, B. Codon usage limitation in the expression of HIV-1 envelope glycoprotein. *Curr Biol* 1996, 6(3), 315-324.

42 Andre, S., Seed, B., Eberle, J., Schraut, W., Bultmann, A. & Haas, J. Increased immune response elicited by DNA vaccination with a synthetic gp120 sequence with optimized codon usage. *J Virol* 1998, 72(2), 1497-1503.

43 Fouts, T. R., Tuskan, R, Godfrey, K. et al. Expression and characterization of a single-chain polypeptide analogue of the human immunodeficiency virus type 1 gp120-CD4 receptor complex. *J Virol* 2000, 74(24), 11427-11436.

44 Jang, S. K., Krausslich, H. G., Nicklin, M. J., Duke, G. M., Palmenberg, A. C. & Wimmer, E. A segment of the 5' nontranslated region of encephalomyocarditis virus RNA directs internal entry of ribosomes during in vitro translation. *J Virol* 1988, 62(8), 2636-2643.

45 Kieft, J. S., Zhou, K., Jubin, R., Murray, M. G., Lau, J. Y. & Doudna, J. A. The hepatitis C virus internal ribosome entry site adopts an ion-dependent tertiary fold. *J Mol Biol* 1999, 292(3), 513-529.

46 Kieft, J. S., Zhou, K., Grech, A., Jubin, R. & Doudna, J. A. Crystal structure of an RNA tertiary domain essential to HCV IRES-mediated translation initiation. *Nat Struct Biol* 2002, 9(5), 370-374.

47 Menard, R., Sansonetti, P. J. & Parsot, C. Nonpolar mutagenesis of the ipa genes defines IpaB, IpaC, and IpaD as effectors of *Shigella flexneri* entry into epithelial cells. *J Bacteriol* 1993, 175(18), 5899-5906.

48 Parks, G. D., Duke, G. M. & Palmenberg, A. C. Encephalomyocarditis virus 3C protease: efficient cell-free expression from clones which link viral 5' noncoding sequences to the P3 region. *J. Virol.* 1986, 60(2), 376-384.

49 Galan, J. E., Nakayama, K. & Curtiss, R. d. Cloning and characterization of the asd gene of *Salmonella typhimurium*: use in stable maintenance of recombinant plasmids in *Salmonella* vaccine strains. Gene 1990, 94(1), 29-35.

50 Bagley, K. C., Fouts, T. R., Carbonetti, N., DeVico, A. L., Lewis, G. K. & Hone, D. M. Immunogenicity of a dicistronic DNA vaccine that directs coincident expression of the 120 kDa glycoprotein of human immunodeficiency virus and the catalytic domain of cholera toxin. (Submitted). 2002.

51 Agwale, S. M., Shata, M. T., Reitz, M. S., Jr. et al. A Tat subunit vaccine confers protective immunity against the immune-modulating activity of the human immunodeficiency virus type-1 Tat protein in mice. *Proc Natl. Acad Sci USA* 2002, 99(15), 10037-10041.

52 Haas, J., Park, E. C. & Seed, B. Codon usage limitation in the expression of HIV-1 envelope glycoprotein. *Curr. Biol.* 1996, 6(3), 315-324.

53 Fouts, T. R., Tuskan, R., Godfrey, K. et al. Expression and characterization of a single-chain polypeptide analogue of the human immunodeficiency virus type 1 gp120-CD4 receptor complex. *J. Virol.* 2000, 74(24), 11427-11436.

54 Emini, E. A., Nara, P. L., Schleif, W. A. et al. Antibody-mediated in vitro neutralization of human immunodeficiency virus type 1 abolishes infectivity for chimpanzees. *J. Virol.* 1990, 64(8), 3674-3678.

55 Putkonen, P., Thorstensson, R., Ghavamzadeh, L. et al. Prevention of HIV-2 and SIVsm infection by passive immunization in cynomolgus monkeys. *Nature* 1991, 352 (6334), 436-438.

56 Emini, E. A., Schleif, W. A., Nunberg, J. H. et al. Prevention of HIV-1 infection in chimpanzees by gp120 V3 domain-specific monoclonal antibody. *Nature* 1992, 355 (6362), 728-730.

57 Conley, A. J., Kessler, J. A., II, Boots, L. J. et al. The consequence of passive administration of an anti-human immunodeficiency virus type 1 neutralizing monoclonal antibody before challenge of chimpanzees with a primary virus isolate. *J. Virol.* 1996, 70(10), 6751-6758.

58 Haigwood, N. L., Watson, A., Sutton, W. F. et al. Passive immune globulin therapy in the SIV/macaque model: early intervention can alter disease profile. *Immunol. Lett.* 1996, 51(1-2), 107-114.

59 Prince, A. M., Reesink, H., Pascual, D. et al. Prevention of HIV infection by passive immunization with HIV immunoglobulin. *AIDS Res. Hum. Retrovir.* 1991, 7(12), 971-973.

60 Parren, P. W., Ditzel, H. J., Gulizia, R. J. et al. Protection against HIV-1 infection in hu-PBL-SCID mice by passive immunization with a neutralizing human monoclonal antibody against the gp120 CD4-binding site. *Aids* 1995, 9(6), F1-6.

61 Murthy, K. K., Cobb, E. K., Rouse, S. R., Lunceford, S. M., Johnson, D. E. & Galvan, A. R. Correlates of protective immunity against HIV-1 infection in immunized chimpanzees. *Immunol. Lett.* 1996, 51(1-2), 121-124.

62 Mascola, J. R., Lewis, M. G., Stiegler, G. et al. Protection of Macaques against pathogenic simian/human immunodeficiency virus 89.6PD by passive transfer of neutralizing antibodies. *J. Virol.* 1999, 73(5), 4009-4018.

63 Mascola, J. R., Stiegler, G., VanCott, T. C. et al. Protection of macaques against vaginal transmission of a pathogenic HIV-1/SIV chimeric virus by passive infusion of neutralizing antibodies. *Nat. Med.* 2000, 6(2), 207-210.

64 Baba, T. W., Liska, V., Hofmann-Lehmann, R. et al. Human neutralizing monoclonal antibodies of the IgG1 subtype protect against mucosal simian-human immunodeficiency virus infection. *Nat. Med.* 2000, 6(2), 200-206.

65 Hofmann-Lehmann, R., Vlasak, J., Rasmussen, R. A. et al. Postnatal passive immunization of neonatal macaques with a triple combination of human monoclonal antibodies against oral simian-human immunodeficiency virus challenge. *J. Virol.* 2001, 75(16), 7470-7480.

66 Moore, J. P., Willey, R. L., Lewis, G. K., Robinson, J. & Sodroski, J. Immunological evidence for interactions between the first, second, and fifth conserved domains of the gp120 surface glycoprotein of human immunodeficiency virus type 1. *J. Virol.* 1994, 68(11), 6836-6847.

67 Moore, J. P., Thali, M., Jameson, B. A. et al. Immunochemical analysis of the gp120 surface glycoprotein of human immunodeficiency virus type 1: probing the structure of the C4 and V4 domains and the interaction of the C4 domain with the V3 loop. *J. Virol.* 1993, 67(8), 4785-4796.

68 Kang, C. Y., Hariharan, K., Nara, P. L., Sodroski, J. & Moore, J. P. Immunization with a soluble CD4-gp120 complex preferentially induces neutralizing anti-human immunodeficiency virus type 1 antibodies directed to conformation-dependent epitopes of gp120. *J. Virol.* 1994, 68(9), 5854-5862.

69 DeVico, A. L., Rahman, R., Welch, J. et al. Monoclonal antibodies raised against covalently crosslinked complexes of human immunodeficiency virus type 1 gp120 and CD4 receptor identify a novel complex-dependent epitope on gp120. *Virol.* 1995, 211(2), 583-588.

70 Pal, R., DeVico, A., Rittenhouse, S. & Sarngadharan, M. G. Conformational perturbation of the envelope glycoprotein gp120 of human immunodeficiency virus type 1 by soluble CD4 and the lectin succinyl Con A. *Virology* 1993, 194(2), 833-837.

71 Sullivan, N., Sun, Y., Sattentau, Q. et al. CD4-Induced conformational changes in the human immunodeficiency virus type 1 gp120 glycoprotein: consequences for virus entry and neutralization. *J. Virol.* 1998, 72(6), 4694-4703.

72 LaCasse, R. A., Follis, K. E., Trahey, M., Scarborough, J. D., Littman, D. R. & Nunberg, J. H. Fusion-competent vaccines: broad neutralization of primary isolates of HIV. *Science* 1999, 283(5400), 357-362.

73 Price, B. M., Liner, A. L., Park, S., Leppla, S. H., Mateczun, A. & Galloway, D. R. Protection against anthrax lethal toxin challenge by genetic immunization with a plasmid encoding the lethal factor protein. *Infect. Immun.* 2001, 69(7), 4509-4515.

74 Mindich, L., Qiao, X., Onodera, S., Gottlieb, P. & Strassman, J. Heterologous recombination in the double-stranded RNA bacteriophage phi 6. *J Virol* 1992, 66(5), 2605-2610.

75 Mindich, L., Qiao, X. & Qiao, J. Packaging of multiple copies of reduced-size genomic segments by bacteriophage phi 6. *Virology* 1995, 212(1), 213-217.

76 Ausubel, F. M., Brent, R., Kingston, R. E. et al. *Current protocols in Immunology*. , Greene Publishing Associates and Wiley-Intersciences, John Wiley and Sons., New York, N.Y., 1992. Chapter 11, Pp11.12.11-11.12.13.

77 Kakitani, H., Iba, H. & Okada, Y. Penetration and partial uncoating of bacteriophage phi 6 particle. *Virol.* 1980, 101 (2), 475-483.

78 Abacioglu, Y. H., Fouts, T. R., Laman, J. D. et al. Epitope mapping and topology of baculovirus-expressed HIV-1 gp160 determined with a panel of murine monoclonal antibodies. *AIDS Res. Hum. Retrovir.* 1994, 10(4), 371-381.

79 Srinivasan, J., Tinge, S., Wright, R., Herr, J. C. & Curtiss, R., 3rd. Oral immunization with attenuated *Salmonella* expressing human sperm antigen induces antibodies in serum and the reproductive tract. *Biol. Reprod.* 1995, 53(2), 462-471.

80 Staats, H. F., Nichols, W. G. & Palker, T. J. Mucosal immunity to HIV-1: systemic and vaginal antibody responses after intranasal immunization with the HIV-1 C4/V3 peptide T1SP10 MN(A). *J. Immunol.* 1996, 157(1), 462-472.

81 Pincus, S. H., Wehrly, K., Cole, R. et al. In vitro effects of anti-HIV immunotoxins directed against multiple epitopes on HIV type 1 envelope glycoprotein 160. *AIDS Res. Hum. Retrovir.* 1996, 12(11), 1041-1051.

82 Yamamoto, S., Kiyono, H., Yamamoto, M. et al. A non-toxic mutant of cholera toxin elicits Th2-type responses for enhanced mucosal immunity. *Proc. Natl. Acad. Sci.* 1997, 94(10), 5267-5272.

83 Wu, S., Pascual, D. W., VanCott, J. L. et al. Immune responses to novel *Escherichia coli* and *Salmonella typhimurium* vectors that express colonization factor antigen I (CFA/I) of enterotoxigenic *E. coli* in the absence of the CFA/I positive regulator cfaR. *Infect. Immun.* 1995, 63(12), 4933-4938.

84 Xu-Amano, J., Kiyono, H., Jackson, R. J. et al. Helper T cell subsets for immunoglobulin A responses: oral immunization with tetanus toxoid and cholera toxin as adjuvant selectively induces Th2 cells in mucosa associated tissues. *J. Exp. Med.* 1993, 178(4), 1309-1320.

85 Okahashi, N., Yamamoto, M., Vancott, J. L. et al. Oral immunization of interleukin-4 (IL-4) knockout mice with a recombinant *Salmonella* strain or cholera toxin reveals that CD4+ Th2 cells producing IL-6 and IL-10 are associated with mucosal immunoglobulin A responses. *Infect. Immun.* 1996, 64(5), 1516-1525.

That which is claimed is:

1. A recombinant double stranded RNA phage (rdsRP) comprising a double stranded RNA eukaryotic expression cassette for expression in eukaryotic cells, the rdsRP comprising:

at least one genomic segment of a double stranded RNA phage (dsgP) and an internal ribosome entry site (IRES) nucleotide sequence incorporated into the at least one genomic segment of the dsRP.

2. The rdsRP according to claim 1, further comprising at least one passenger gene sequence incorporated into the at least one genomic segment of the dsRP.

3. The rdsRP according to claim 1, wherein the IRES is inserted into at least one of three dsRNA genomic segments of the dsRP selected from the group consisting of segment L, segment M and segment S.

4. The rdsRP according to claim 2, wherein the passenger gene and the IRES are functionally linked.

5. The rdsRP according to claim 1, wherein said eukaryotic expression cassette is an alpha virus expression cassette.

6. The rdsRP according to claim 2, wherein the passenger gene encodes for an immunogen.

7. The rdsRP according to claim 1, wherein the dsRP is Phi-6, Phi-8, or Phi-i 3.

8. The rdsRP according to claim 2 , wherein the rdsRP genomic segment is expressed and amplified in a bacterial host strain.

9. The rdsRP according to claim 6, wherein the rdsRP genomic segment further comprises an adjuvant as an additional passenger gene.

10. The rdsRP according to claim 6, wherein the rdsRP genomic segment further comprises a cytokine.

11. The rdsRP according to claim 7, wherein the immunogen is foreign or endogenous.

12. The rdsRP according to claim 11, wherein the immunogen is foreign and is a member selected from the group consisting of viral proteins, bacterial proteins, parasite proteins, cytokines, chemokines, immunoregulatory agents, and therapeutic agents.

13. The rdsRP according to claim 12, wherein the immunogen originates from a viral pathogen, bacterial pathogen, or parasitic pathogen.

14. The rdsRP according to claim 13, wherein the immunogen originates from a viral pathogen comprising a member selected from the group consisting of Orthomyxoviruses, Retroviruses, Herpesviruses, Lentiviruses, Rhabdoviruses, Picornoviruses, Poxviruses, Rotavirus and Parvoviruses.

15. The rdsRP according to claim 12, wherein the viral protein is a member selected from the group consisting of: human immunodeficiency virus antigens, Nef, Rev, mutant derivatives of Tat, Tat-A31-45, Pol, T cell epitopes of gp 120, and B cell epitopes of gp 120, chimeric derivatives of HIV-1-CD4, chimeric Env-CD4, chimeric gp120-CD4, hepatitis B surface antigen, rotavirus antigens, influenza virus antigens, and herpes simplex virus antigens.

16. The rdsRP according to claim 12, wherein the immunogen is endogenous and is a member selected from the group consisting of cellular proteins, immunoregulatory agents, therapeutic agents, tumor immunogens, autoimmune immunogens and parts thereof.

17. The rdsRP according to claim 16, wherein the tumor immunogen comprises a member selected from the group consisting of PSA, CEA, MAGE-1 and tyrosinase.

18. The rdsRP according to claim 9, where the adjuvant comprises a member selected from the group consisting of: A subunit of cholera toxin, bacterial adenosine diphosphate-ribosylating exotoxins, pertussis toxin Si subunit, adenylate cyclase-hemolysins of Bordetella pertussis, and parts thereof.

19. The rdsRP according to claim 10, wherein the cytokine is a member selected from the group consisting of; interleukin-4, IL-5, IL-6, IL-10, IL-$12_{p40}$, IL-$12_{p70}$, TGFfβ and TNFα.

20. The rdsRP according to claim 2, wherein the IRES comprises a member selected from the group consisting of: the IRES located at nucleotides 665-1251 in pIRES2-EGFP (SEQ ID NO: 6), IRES from plasmid pCITE4a (SEQ ID NO: 7), IRES from plasmid pSVIRES-N (SEQ ID NO: 4), IRES of the 3'-untranslated region of the mRNA for the beta subunit of mitochondrial H+-ATP synthase (SEQ ID NO: 8), SEQ ID NO: 1, SEQ ID NO: 2, SEQ ID NO: 3, SEQ ID NO: 4 and SEQ ID NO: 5.

21. A composition comprising the rdsRP according to claim 4.

22. The composition according to claim 21, wherein the rdsRP comprises an alpha virus expression cassette.

23. The composition according to claim 21, wherein the passenger gene encodes for an immunogen.

24. The composition according to claim 21, wherein the dsRP is Phi-6, Phi-8, or Phi-i 3.

25. The composition according to claim 21, wherein the rdsRP genomic segment is amplified in a bacterial host strain.

26. The composition according to claim 21, wherein the rdsRP genomic segment further encodes for an adjuvant as a second passenger gene.

27. The composition according to claim 21, wherein the rdsRP genomic segment further encodes for a cytokine.

28. The composition according to claim 21, wherein the immunogen is foreign or endogenous.

29. The composition according to claim 28, wherein the immunogen is foreign and is a member selected from the group consisting of viral proteins, bacterial proteins, parasite proteins, cytokines, chemokines, immunoregulatory agents, and therapeutic agents.

30. A method of inducing an immune response or biological activity comprising administering to a subject the rdsRP according to claim 4 via bacterial vector delivery thereof to cells or tissues of said subject, in a sufficient amount to express an effective amount of encoded passenger gene.

31. The method according to claim 30, wherein rdsRP is delivered with a pharmaceutically acceptable carrier or diluent.

32. A live bacterium comprising at least one dsRP according to claim 4.

* * * * *

UNITED STATES PATENT AND TRADEMARK OFFICE
CERTIFICATE OF CORRECTION

PATENT NO. : 7,407,790 B2
APPLICATION NO. : 10/525702
DATED : August 5, 2008
INVENTOR(S) : David Hone It is certified that error appears in the above-identified patent and that said Letters Patent is hereby corrected as shown below:

Column 1, line 16: “Nos, A1 41914” should be -- Nos. A1 41914 --.
Column 3, line 24: “Chatteiji” should be -- Chatterji --.
Column 6, line 62: “[44]SEQ ID NO: 6” should be -- [44]: SEQ ID NO: 6 --.
Column 6, lines 65-67: “(http://www” should be -- at hypertext transfer protocol world wide web address --.
Column 7, lines 5-10: “pCITE4a is available at http://www.novagen.com/docs/NDIS/69913-000.HTM). on plasmids pCLIE4a-c (Novagen, URL:–http://www.novagen.com; U.S. Pat. No. 4,937,190); pSLIRES11 (Accession: AF171227; pPV (Accession # Y07702); pSVIRES-N (Accession #: AJ000156)” should be -- pCITE4a (SEQ ID NO: 7) is available at hypertext transfer protocol world wide web address novagen.com/docs/NDIS/69913-000.HTML); on plasmids pCITE4a-c (Novagen, hypertext transfer protocol world wide web address novagen.com; US patent # 4,937,190); pSLIRES11 (GenBank Accession: AF171227.1; SEQ ID NO: 2); pPV (GenBank Accession # Y07702.1; SEQ ID NO: 3); pSVIRES-N (GenBank Accession #: AJ000156.1; SEQ ID NO: 4) --.
Column 7, line 17: “(GenBank Accession #: D88622)” should be -- (GenBank Accession #: D88622.1; SEQ ID NO: 5) --.
Column 7, line 23: “(2000)’ should be -- (2000) (SEQ ID NO: 8) --.
Column 7, line 30: “(Genebank accession no. Y11034)” should be -- (GenBank accession no. Y11034.1; SEQ ID NO: 1) --.
Column 7, lines 31-32: “(http://www” should be -- (at hypertext transfer protocol world wide web address --.
Column 7, line 39: “pCITE4a” should be -- pCITE4a (SEQ ID NO: 7) --.
Column 7, line 41: “Genebank” should be -- GenBank --.
Column 7, line 47, add: -- The references cited hereinabove in connection with SEQ ID NOS: 1-8 are hereby incorporated by reference in their respective entireties. --.
Column 8, line 46: “outs” should be -- Fouts --.
Column 8, line 67: “Salnlonella” should be -- Salmonella --.
Column 9, line 29: “Plasmzodium” should be -- Plasmodium --.
Column 10, line 14: “antigen Koeppen” should be -- antigen, Koeppen --.
Column 12, line 54: “Pst L Hind III” should be -- Pst L, Hind III --.
Column 21, line 2: “1KH6¯A” should be -- 1KH6_A --.
Column 63, line 55 (claim 1): “(dsgP)” should be -- (dsRP) --.
Column 64, line 54 (claim 7): “Phi-i 3” should be -- Phi-13 --.
Column 65, line 31 (claim 18): “Si subunit” should be -- S1 subunit --.

UNITED STATES PATENT AND TRADEMARK OFFICE

CERTIFICATE OF CORRECTION

PATENT NO. : 7,407,790 B2 
APPLICATION NO. : 10/525702
DATED : August 5, 2008
INVENTOR(S) : David Hone It is certified that error appears in the above-identified patent and that said Letters Patent is hereby corrected as shown below:

Column 65, line 35 (claim 19): "TGFfβ" should be -- TGFβ --.
Column 66, line 14 (claim 24): "Phi-i 3" should be -- Phi-13 --.

Signed and Sealed this

Thirtieth Day of June, 2009

JOHN DOLL
*Acting Director of the United States Patent and Trademark Office*

UNITED STATES PATENT AND TRADEMARK OFFICE

CERTIFICATE OF CORRECTION

PATENT NO. : 7,407,790 B2
APPLICATION NO. : 10/525702
DATED : August 5, 2008
INVENTOR(S) : David Hone It is certified that error appears in the above-identified patent and that said Letters Patent is hereby corrected as shown below:

Column 1, lines 15-16: The United States Government has rights in this invention under NIATD Grant Nos, A1 41914, A1 47490 and A1 43756." should be -- This invention was made with government support under Grant Numbers AI041914, AI043756, and AI047490 awarded by the National Institutes of Health. The government has certain rights in the invention. --.

Signed and Sealed this
Twentieth Day of March, 2012

David J. Kappos
*Director of the United States Patent and Trademark Office*

SEQUENCE LISTING

```
<160> NUMBER OF SEQ ID NOS: 8

<210> SEQ ID NO 1
<211> LENGTH: 6067
<212> TYPE: DNA
<213> ORGANISM: Artificial Sequence
<220> FEATURE:
<223> OTHER INFORMATION: Synthetic construct

<400> SEQUENCE: 1

tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaataaccc    660

cgccccgttg acgcaaatgg gcggtaggcg tgtacggtgg gaggtctata taagcagagc    720

tcgtttagtg aaccgtcaga tcactagaag ctttattgcg gtagtttatc acagttaaat    780

tgctaacgca gtcagtgctt ctgacacaac agtctcgaac ttaagctgca gaagttggtc    840

gtgaggcact gggcaggtaa gtatcaaggt tacaagacag gtttaaggag accaatagaa    900

actgggcttg tcgagacaga gaagactctt gcgtttctga taggcaccta ttggtcttac    960

tgacatccac tttgcctttc tctccacagg tgtccactcc cagttcaatt acagctctta   1020

aggctagagt acttaatacg actcactata ggctagcctc gagaattcac gcgtggtacc   1080

tctagagtcg acccgggcgg ccgctctagc ccaattccgc ccctctccct cccccccccc   1140

taacgttact ggccgaagcc gcttggaata aggccggtgt gcgtttgtct atatgttatt   1200

ttccaccata ttgccgtctt ttggcaatgt gagggcccgg aaacctggcc ctgtcttctt   1260

gacgagcatt cctaggggtc tttcccctct cgccaaagga atgcaaggtc tgttgaatgt   1320
```

-continued

```
cgtgaaggaa gcagttcctc tggaagcttc ttgaagacaa acaacgtctg tagcgaccct   1380
ttgcaggcag cggaaccccc cacctggcga caggtgcctc tgcggccaaa agccacgtgt   1440
ataagataca cctgcaaagg cggcacaacc ccagtgccac gttgtgagtt ggatagttgt   1500
ggaaagagtc aaatggctct cctcaagcgt attcaacaag gggctgaagg atgcccagaa   1560
ggtaccccat tgtatgggat ctgatctggg gcctcggtgc acatgcttta catgtgttta   1620
gtcgaggtta aaaaacgtct aggccccccg aaccacgggg acgtggtttt cctttgaaaa   1680
acacgatgat aatatgggca gcgaaaaata catcgtcacc tgggacatgt tgcagatcca   1740
tgcacgtaaa ctcgcaagcc gactgatgcc ttctgaacaa tggaaaggca ttattgccgt   1800
aagccgtggc ggtctggtac cgggtgcgtt actggcgcgt gaactgggta ttcgtcatgt   1860
cgataccgtt tgtatttcca gctacgatca cgacaaccag cgcgagctta aagtgctgaa   1920
acgcgcagaa ggcgatggcg aaggcttcat cgttattgat gacctggtgg ataccggtgg   1980
tactgcggtt gcgattcgtg aaatgtatcc aaaagcgcac tttgtcacca tcttcgcaaa   2040
accggctggt cgtccgctgg ttgatgacta tgttgttgat atcccgcaag atacctggat   2100
tgaacagccg tgggatatgg gcgtcgtatt cgtcccgcca atctccggtc gctaatcttt   2160
tcaacgcctg gcactgccgg gcgttgttct ttttaacttc aggcgggtta caatagtttc   2220
cagtaagtat tctggaggct gcatccatga cacaggcaaa cctgagcgaa accctgttca   2280
aaccccgctt taaacatcct gaaacctcga cgctagtccg ccgctttaat cacggcgcac   2340
aaccgcctgt gcagtcggcc cttgatggta aaaccatccc tcactggtat cgcatgatta   2400
accgtctgat gtggatctgg cgcggcattg acccacgcga aatcctcgac gtccaggcac   2460
gtattgtgat gagcgatgcc gaacgtaccg acgatgattt atacgatacg gtgattggct   2520
accgtggcgg caactggatt tatgagtggg ccccggatct ttgtgaagga accttacttc   2580
tgtggtgtga cataattgga caaactacct acagagattt aaagctctaa ggtaaatata   2640
aaatttttaa gtgtataatg tgttaaacta ctgattctaa ttgtttgtgt attttagatt   2700
ccaacctatg gaactgatga atgggagcag tggtggaatg cctttaatga ggaaaacctg   2760
ttttgctcag aagaaatgcc atctagtgat gatgaggcta ctgctgactc tcaacattct   2820
actcctccaa aaaagaagag aaaggtagaa gaccccaagg actttccttc agaattgcta   2880
agtttttga gtcatgctgt gtttagtaat agaactcttg cttgctttgc tatttacacc   2940
acaaaggaaa aagctgcact gctatacaag aaaattatgg aaaaatattc tgtaaccttt   3000
ataagtaggc ataacagtta taatcataac atactgtttt ttcttactcc acacaggcat   3060
agagtgtctg ctattaataa ctatgctcaa aaattgtgta cctttagctt tttaatttgt   3120
aaaggggtta ataaggaata tttgatgtat agtgccttga ctagagatca taatcagcca   3180
taccacattt gtagaggttt tacttgcttt aaaaaacctc ccacacctcc ccctgaacct   3240
gaaacataaa atgaatgcaa ttgttgttgt taacttgttt attgcagctt ataatggtta   3300
caaataaagc aatagcatca caaatttcac aaataaagca tttttttcac tgcattctag   3360
ttgtggtttg tccaaactca tcaatgtatc ttatcatgtc tggatccggg ctggcgtaat   3420
agcgaagagg cccgcaccga tcgcccttcc caacagttgc gcagcctgaa tggcgaatgg   3480
acgcgccctg tagcggcgca ttaagcgcgg cgggtgtggt ggttacgcgc agcgtgaccg   3540
ctacacttgc cagcgcccta gcgcccgctc ctttcgcttt cttcccttcc tttctcgcca   3600
cgttcgccgg ctttccccgt caagctctaa atcgggggct ccctttaggg ttccgattta   3660
```

-continued

```
gagctttacg gcacctcgac cgcaaaaaac ttgatttggg tgatggttca cgtagtgggc   3720
catcgccctg atagacggtt tttcgccctt tgacgttgga gtccacgttc tttaatagtg   3780
gactcttgtt ccaaactgga acaacactca accctatctc ggtctattct tttgatttat   3840
aagggatttt gccgatttcg gcctattggt taaaaaatga gctgatttaa caaatattta   3900
acgcgaattt taacaaaata ttaacgttta caatttcgcc tgatgcggta ttttctcctt   3960
acgcatctgt gcggtatttc acaccgcata tggtgcactc tcagtacaat ctgctctgat   4020
gccgcatagt taagccagcc ccgacacccg ccaacacccg ctgacgcgcc ctgacgggct   4080
tgtctgctcc cggcatccgc ttacagacaa gctgtgaccg tctccgggag ctgcatgtgt   4140
cagaggtttt caccgtcatc accgaaacgc gcgagacgaa agggcctcgt gatacgccta   4200
tttttatagg ttaatgtcat gataataatg gtttcttaga cgtcaggtgg cacttttcgg   4260
ggaaatgtgc gcggaacccc tatttgttta tttttctaaa tacattcaaa tatgtatccg   4320
ctcatgagac aataaccctg ataaatgctt caataatatt gaaaaaggaa gagtatgagt   4380
attcaacatt tccgtgtcgc ccttattccc ttttttgcgg cattttgcct tcctgttttt   4440
gctcacccag aaacgctggt gaaagtaaaa gatgctgaag atcagttggg tgcacgagtg   4500
ggttacatcg aactggatct caacagcggt aagatccttg agagttttcg ccccgaagaa   4560
cgttttccaa tgatgagcac ttttaaagtt ctgctatgtg gcgcggtatt atcccgtatt   4620
gacgccgggc aagagcaact cggtcgccgc atacactatt ctcagaatga cttggttgag   4680
tactcaccag tcacagaaaa gcatcttacg gatggcatga cagtaagaga attatgcagt   4740
gctgccataa ccatgagtga taacactgcg gccaacttac ttctgacaac gatcggagga   4800
ccgaaggagc taaccgcttt tttgcacaac atgggggatc atgtaactcg ccttgatcgt   4860
tgggaaccgg agctgaatga agccatacca aacgacgagc gtgacaccac gatgcctgta   4920
gcaatggcaa caacgttgcg caaactatta actggcgaac tacttactct agcttcccgg   4980
caacaattaa tagactggat ggaggcggat aaagttgcag gaccacttct gcgctcggcc   5040
cttccggctg gctggtttat tgctgataaa tctggagccg gtgagcgtgg gtctcgcggt   5100
atcattgcag cactggggcc agatggtaag ccctcccgta tcgtagttat ctacacgacg   5160
gggagtcagg caactatgga tgaacgaaat agacagatcg ctgagatagg tgcctcactg   5220
attaagcatt ggtaactgtc agaccaagtt tactcatata tactttagat tgatttaaaa   5280
cttcattttt aatttaaaag gatctaggtg aagatccttt ttgataatct catgaccaaa   5340
atcccttaac gtgagttttc gttccactga gcgtcagacc ccgtagaaaa gatcaaagga   5400
tcttcttgag atcctttttt tctgcgcgta atctgctgct tgcaaacaaa aaaaccaccg   5460
ctaccagcgg tggtttgttt gccggatcaa gagctaccaa ctctttttcc gaaggtaact   5520
ggcttcagca gagcgcagat accaaatact gtccttctag tgtagccgta gttaggccac   5580
cacttcaaga actctgtagc accgcctaca tacctcgctc tgctaatcct gttaccagtg   5640
gctgctgcca gtggcgataa gtcgtgtctt accgggttgg actcaagacg atagttaccg   5700
gataaggcgc agcggtcggg ctgaacgggg ggttcgtgca cacagcccag cttggagcga   5760
acgacctaca ccgaactgag atacctacag cgtgagctat gagaaagcgc cacgcttccc   5820
gaagggagaa aggcggacag gtatccggta agcggcaggg tcggaacagg agagcgcacg   5880
agggagcttc cagggggaaa cgcctggtat ctttatagtc ctgtcgggtt tcgccacctc   5940
tgacttgagc gtcgattttt gtgatgctcg tcaggggggc ggagcctatg gaaaaacgcc   6000
agcaacgcgg cctttttacg gttcctggcc ttttgctggc cttttgctca catggctcga   6060
```

-continued

```
cagatct                                                              6067

<210> SEQ ID NO 2
<211> LENGTH: 3552
<212> TYPE: DNA
<213> ORGANISM: Artificial Sequence
<220> FEATURE:
<223> OTHER INFORMATION: Synthetic construct

<400> SEQUENCE: 2

gtggcacttt tcggggaaat gtgcgcggaa cccctatttg tttatttttc taaatacatt      60

caaatatgta tccgctcatg agacaataac cctgataaat gcttcaataa tattgaaaaa     120

ggaagagtat gagtattcaa catttccgtg tcgcccttat tccctttttt gcggcatttt     180

gccttcctgt ttttgctcac ccagaaacgc tggtgaaagt aaaagatgct gaagatcagt     240

tgggtgcacg agtgggttac atcgaactgg atctcaacag cggtaagatc cttgagagtt     300

ttcgccccga agaacgtttt ccaatgatga gcacttttaa agttctgcta tgtggcgcgg     360

tattatcccg tattgacgcc gggcaagagc aactcggtcg ccgcatacac tattctcaga     420

atgacttggt tgagtactca ccagtcacag aaaagcatct tacggatggc atgacagtaa     480

gagaattatg cagtgctgcc ataaccatga gtgataacac tgcggccaac ttacttctga     540

caacgatcgg aggaccgaag gagctaaccg cttttttgca caacatgggg gatcatgtaa     600

ctcgccttga tcgttgggaa ccggagctga atgaagccat accaaacgac gagcgtgaca     660

ccacgatgcc tgtagcaatg gcaacaacgt tgcgcaaact attaactggc gaactactta     720

ctctagcttc ccggcaacaa ttaatagact ggatggaggc ggataaagtt gcaggaccac     780

ttctgcgctc ggcccttccg gctggctggt ttattgctga taaatctgga gccggtgagc     840

gtgggtctcg cggtatcatt gcagcactgg ggccagatgg taagccctcc cgtatcgtag     900

ttatctacac gacggggagt caggcaacta tggatgaacg aaatagacag atcgctgaga     960

taggtgcctc actgattaag cattggtaac tgtcagacca agtttactca tatatacttt    1020

agattgattt aaaacttcat ttttaattta aaaggatcta ggtgaagatc ctttttgata    1080

atctcatgac caaaatccct taacgtgagt tttcgttcca ctgagcgtca gaccccgtag    1140

aaaagatcaa aggatcttct tgagatcctt tttttctgcg cgtaatctgc tgcttgcaaa    1200

caaaaaaacc accgctacca gcggtggttt gtttgccgga tcaagagcta ccaactcttt    1260

ttccgaaggt aactggcttc agcagagcgc agataccaaa tactgtcctt ctagtgtagc    1320

cgtagttagg ccaccacttc aagaactctg tagcaccgcc tacatacctc gctctgctaa    1380

tcctgttacc agtggctgct gccagtggcg ataagtcgtg tcttaccggg ttggactcaa    1440

gacgatagtt accggataag gcgcagcggt cgggctgaac ggggggttcg tgcacacagc    1500

ccagcttgga gcgaacgacc tacaccgaac tgagatacct acagcgtgag ctatgagaaa    1560

gcgccacgct tcccgaaggg agaaaggcgg acaggtatcc ggtaagcggc agggtcggaa    1620

caggagagcg cacgagggag cttccagggg gaaacgcctg gtatctttat agtcctgtcg    1680

ggtttcgcca cctctgactt gagcgtcgat ttttgtgatg ctcgtcaggg gggcggagcc    1740

tatggaaaaa cgccagcaac gcggcctttt tacggttcct ggccttttgc tggccttttg    1800

ctcacatgtt ctttcctgcg ttatcccctg attctgtgga taaccgtatt accgcctttg    1860

agtgagctga taccgctcgc cgcagccgaa cgaccgagcg cagcgagtca gtgagcgagg    1920

aagcggaaga gcgcccaata cgcaaaccgc ctctccccgc gcgttggccg attcattaat    1980
```

-continued

```
gcagctggca cgacaggttt cccgactgga aagcgggcag tgagcgcaac gcaattaatg   2040

tgagttagct cactcattag gcaccccagg ctttacactt tatgcttccg gctcgtatgt   2100

tgtgtggaat tgtgagcgga taacaatttc acacaggaaa cagctatgac catgattacg   2160

ccaagctcga aattaaccct cactaaaggg aacaaaagct ggagctcatc gattctagac   2220

tccctccccc cccctaacg ttactggccg aagccgcttg gaataaggcc ggtgtgcgtt   2280

tgtctatatg ttattttcca ccatattgcc gtcttttggc aatgtgaggg cccggaaacc   2340

tggccctgtc ttcttgacga gcattcctag gggtctttcc cctctcgcca aaggaatgca   2400

aggtctgttg aatgtcgtga aggaagcagt tcctctggaa gcttcttgaa gacaaacaac   2460

gtctgtagcg accctttgca ggcagcggaa ccccccacct ggcgacaggt gcctctgcgg   2520

ccaaaagcca cgtgtataag atacacctgc aaaggcggca caaccccagt gccacgttgt   2580

gagttggata gttgtggaaa gagtcaaatg gctctcctca agcgtattca acaaggggct   2640

gaaggatgcc cagaaggtac cccattgtat gggatctgat ctggggcctc ggtgcacatg   2700

ctttacgtgt gtttagtcga ggttaaaaaa cgtctaggcc ccccgaacca cggggacgtg   2760

gttttccttt gaaaaacacg atgataatac catggccatg attacgaatt cgagctcgcc   2820

cggggatccg atatcactag tgcggccgct gcagcccaag cttatcgata ccgtcgacct   2880

cgatcgaggg ggggcccggt acccaattcg ccctatagtg agtcgtatta caattcactg   2940

gccgtcgttt tacaacgtcg tgactgggaa aaccctggcg ttacccaact taatcgcctt   3000

gcagcacatc ccccttcgc cagctggcgt aatagcgaag aggcccgcac cgatcgccct   3060

tcccaacagt tgcgcagcct gaatggcgaa tgggacgcgc cctgtagcgg cgcattaagc   3120

gcggcgggtg tggtggttac gcgcagcgtg accgctacac ttgccagcgc cctagcgccc   3180

gctcctttcg ctttcttccc ttcctttctc gccacgttcg ccggctttcc ccgtcaagct   3240

ctaaatcggg ggctcccttt agggttccga tttagtgctt tacggcacct cgaccccaaa   3300

aaacttgatt agggtgatgg ttcacgtagt gggccatcgc cctgatagac ggtttttcgc   3360

cctttgacgt tggagtccac gttctttaat agtggactct tgttccaaac tggaacaaca   3420

ctcaacccta tctcggtcta ttcttttgat ttataaggga ttttgccgat ttcggcctat   3480

tggttaaaaa atgagctgat ttaacaaaaa tttaacgcga attttaacaa aatattaacg   3540

cttacaattt ag                                                       3552
```

<210> SEQ ID NO 3
<211> LENGTH: 4946
<212> TYPE: DNA
<213> ORGANISM: Artificial Sequence
<220> FEATURE:
<223> OTHER INFORMATION: Synthetic construct

<400> SEQUENCE: 3

```
ggatccggct gtggaatgtg tgtcagttag ggtgtggaaa gtccccaggc tccccagcag     60

gcagaagtat gcaaagcatg catcacaatt agtcagcaac caggtgtgga aagtccccag    120

gctccccagc aggcagaagt atgcaaagca tgcatctcaa ttagtcagca accatagtcc    180

cgcccctaac tccgcccatc ccgcccctaa ctccgcccag ttccgcccat tctccgcccc    240

atggctgact aatttttttt atttatgcag aggccgaggc cgcctcggcc tctgagctat    300

tccagaagta gtgaggaggc ttttttggag gcctaggctt ttgcaaaaag cttgaattcg    360

ctgtctgcga gggccggctg ttggggtgag tactccctct caaaagcggg catgacttct    420

gcgctaagat tgtcagtttc caaaaacgag gaggatttga tattcacctg gcccgcggtg    480
```

-continued atgcctttga gggtggccgc gtccatctgg tcagaaaaga caatcttttt gttgtcaagc 540
ttgaggtgtg gcaggcttga gatctggcca tacacttgag tgacaatgac atccactttg 600
cctttctctc cacaggtgtc cactcccagg tccaactgca ggtcgacgtc atgaggatgc 660
ttctgcattt gagtttgcta gctcttggtg ctgcctacgt gtatgccatc cccacagaaa 720
tccccactag tgcactggtg aaagagacct tggcactgct gtcaactcat cgtactctgc 780
tgatagccaa tgagactctg cgtatccctg ttcctgtaca taaaaatcac cagctgtgca 840
ctgaagaaat ctttcagggt atcggtaccc tggagagtca aactgtgcaa ggtggtactg 900
tggaacgtct attcaaaaac ttgtccttaa tcaagaaata catcgacggt cagaagaaga 960
agtgtggtga agaacgtcgt cgtgtaaacc aattcctaga ctacctgcag gagtttcttg 1020
gtgtaatgaa caccgagtgg atcatcgaaa gttgacgtcg actctagagg atccccctgg 1080
cgaaaggggg atgtgctgca aggcgattaa gttgggtaac gccagggttt tcccagtcac 1140
gacgttgtaa aacgacggcc agtgaattgt aatacgactc actatagggc gaattaattc 1200
cggttatttt ccaccatatt gccgtctttt ggcaatgtga gggcccggaa acctggccct 1260
gtcttcttga cgagcattcc taggggtctt tcccctctcg ccaaaggaat gcaaggtctg 1320
ttgaatgtcg tgaaggaagc agttcctctg gaagcttctt gaagacaaac aacgtctgta 1380
gcgacccttt gcaggcagcg gaacccccca cctggcgaca ggtgcctctg cggccaaaag 1440
ccacgtgtat aagatacacc tgcaaaggcg gcacaacccc agtgccacgt tgtgagttgg 1500
atagttgtgg aaagagtcaa atggctctcc tcaagcgtat tcaacaaggg gctgaaggat 1560
gcccagaagg taccccattg tatgggatct gatctggggc ctcggtgcac atgctttaca 1620
tgtgtttagt cgaggttaaa aaacgtctag gccccccgaa ccacggggac gtggttttcc 1680
tttgaaaaac acgatgataa tatggccacc acccatatga aagaaaccgc tgctgctaaa 1740
ttcgaacgcc agcacatgga cagcccagat cagggtaccc tggtgccacg cggttccatg 1800
ggatatcctc gcgagttgcc cggcattga ctaagtagct cgagcaccac caccaccacc 1860
actgagatca gcctcgactg tgccttctag ttgccagcca tctgttgttt gcccctcccc 1920
cgtgccttcc ttgaccctgg aaggtgccac tcccactgtc ctttcctaat aaaatgagga 1980
aattgcatcg cattgtctga gtaggtgtca ttctattctg gggggtgggg tggggcagga 2040
cagcaagggg gaggattggg aagacaatag caggcatgct ggggatgcgg tgggctctat 2100
ggcttctgag gcggaaagaa ccagctgggg ctcgagatcc actagttcta gcctcgaggc 2160
tagagcggcc gcgaattctt gaagacgaaa gggcctcgtg atacgcctat ttttataggt 2220
taatgtcatg ataataatgg tttcttagac gtcaggtggc acttttcggg gaaatgtgcg 2280
cggaacccct atttgtttat ttttctaaat acattcaaat atgtatccgc tcatgagaca 2340
ataaccctga taaatgcttc aataatattg aaaaaggaag agtatgagta ttcaacattt 2400
ccgtgtcgcc cttattccct tttttgcggc attttgcctt cctgtttttg ctcacccaga 2460
aacgctggtg aaagtaaaag atgctgaaga tcagttgggt gcacgagtgg gttacatcga 2520
actggatctc aacagcggta agatccttga gagttttcgc cccgaagaac gttttccaat 2580
gatgagcact tttaaagttc tgctatgtgg cgcggtatta tcccgtgttg acgccgggca 2640
agagcaactc ggtcgccgca tacactattc tcagaatgac ttggttgagt actcaccagt 2700
cacagaaaag catcttacgg atggcatgac agtaagagaa ttatgcagtg ctgccataac 2760
catgagtgat aacactgcgg ccaacttact tctgacaacg atcggaggac cgaaggagct 2820

-continued aaccgctttt ttgcacaaca tgggggatca tgtaactcgc cttgatcgtt gggaaccgga 2880
gctgaatgaa gccataccaa acgacgagcg tgacaccacg atgcctgcag caatggcaac 2940
aacgttgcgc aaactattaa ctggcgaact acttactcta gcttcccggc aacaattaat 3000
agactggatg gaggcggata aagttgcagg accacttctg cgctcggccc ttccggctgg 3060
ctggtttatt gctgataaat ctggagccgg tgagcgtggg tctcgcggta tcattgcagc 3120
actggggcca gatggtaagc cctcccgtat cgtagttatc tacacgacgg ggagtcaggc 3180
aactatggat gaacgaaata gacagatcgc tgagataggt gcctcactga ttaagcattg 3240
gtaactgtca gaccaagttt actcatatat actttagatt gatttaaaac ttcattttta 3300
atttaaaagg atctaggtga agatcctttt tgataatctc atgaccaaaa tcccttaacg 3360
tgagttttcg ttccactgag cgtcagaccc cgtagaaaag atcaaaggat cttcttgaga 3420
tccttttttt ctgcgcgtaa tctgctgctt gcaaacaaaa aaaccaccgc taccagcggt 3480
ggtttgtttg ccggatcaag agctaccaac tctttttccg aaggtaactg gcttcagcag 3540
agcgcagata ccaaatactg tccttctagt gtagccgtag ttaggccacc acttcaagaa 3600
ctctgtagca ccgcctacat acctcgctct gctaatcctg ttaccagtgg ctgctgccag 3660
tggcgataag tcgtgtctta ccgggttgga ctcaagacga tagttaccgg ataaggcgca 3720
gcggtcgggc tgaacggggg gttcgtgcac acagcccagc ttggagcgaa cgacctacac 3780
cgaactgaga tacctacagc gtgagcattg agaaagcgcc acgcttcccg aagggagaaa 3840
ggcggacagg tatccggtaa gcggcagggt cggaacagga gagcgcacga gggagcttcc 3900
agggggaaac gcctggtatc tttatagtcc tgtcgggttt cgccacctct gacttgagcg 3960
tcgatttttg tgatgctcgt caggggggcg gagcctatgg aaaaacgcca gcaacgcggc 4020
ctttttacgg ttcctggcct tttgctggcc ttttgctcac atgttctttc ctgcgttatc 4080
ccctgattct gtggataacc gtattaccgc ctttgagtga gctgataccg ctcgccgcag 4140
ccgaacgacc gagcgcagcg agtcagtgag cgaggaagcg gaagagcgcc tgatgcggta 4200
ttttctcctt acgcatctgt gcggtatttc acaccgcata tggtgcactc tcagtacaat 4260
ctgctctgat gccgcatagt taagccagta tacactccgc tatcgctacg tgactgggtc 4320
atggctgcgc cccgacaccc gccaacaccc gctgacgcgc cctgacgggc ttgtctgctc 4380
ccggcatccg cttacagaca agctgtgacc gtctccggga gctgcatgtg tcagaggttt 4440
tcaccgtcat caccgaaacg cgcgaggcag ccggatcata atcagccata ccacatttgt 4500
agaggtttta cttgctttaa aaaacctccc acacctcccc ctgaacctga aacataaaat 4560
gaatgcaatt gttgttgtta acttgtttat tgcagcttat aatggttaca aataaagcaa 4620
tagcatcaca aatttcacaa ataaagcatt tttttcactg cattctagtt gtggtttgtc 4680
caaactcatc aatgtatctt atcatgtctg gatcataatc agccatacca catttgtaga 4740
ggttttactt gctttaaaaa acctcccaca cctccccctg aacctgaaac ataaaatgaa 4800
tgcaattgtt gttgttaact tgtttattgc agcttataat ggttacaaat aaagcaatag 4860
catcacaaat ttcacaaata aagcattttt ttcactgcat tctagttgtg gtttgtccaa 4920
actcatcaat gtatcttatc atgtct 4946

<210> SEQ ID NO 4
<211> LENGTH: 4910
<212> TYPE: DNA
<213> ORGANISM: Artificial Sequence
<220> FEATURE:
<223> OTHER INFORMATION: synthetic construct -continued

<400> SEQUENCE: 4

```
gcgcagcacc atggcctgaa ataacctctg aaagaggaac ttggttaggt accttctgag      60
gcggaaagaa ccagctgtgg aatgtgtgtc agttagggtg tggaaagtcc ccaggctccc     120
cagcaggcag aagtatgcaa agcatgcatc tcaattagtc agcaaccagg tgtggaaagt     180
ccccaggctc cccagcaggc agaagtatgc aaagcatgca tctcaattag tcagcaacca     240
tagtcccgcc cctaactccg cccatcccgc ccctaactcc gcccagttcc gcccattctc     300
cgccccatgg ctgactaatt ttttttattt atgcagaggc cgaggccgcc tcggcctctg     360
agctattcca gaagtagtga ggaggctttt ttggaggcct aggcttttgc aaaaagcttg     420
attcttctga cacaacagtc tcgaacttaa gctgcagaag ttggtcgtga ggcactgggc     480
aggtaagtat caaggttaca agacaggttt aaggagacca atagaaactg ggcttgtcga     540
gacagagaag actcttgcgt ttctgatagg cacctattgg tcttactgac atccactttg     600
cctttctctc cacaggtgtc cactcccagt tcaattacag ctcttaaggc tagagtactt     660
aatacgactc actataggct agcctcgaga attcacgcgt ggtacctcta gagtcgaccc     720
gggcggccgc tctagcccaa ttccgcccct ctccctcccc cccccctaac gttactggcc     780
gaagccgctt ggaataaggc cggtgtgcgt ttgtctatat gttattttcc accatattgc     840
cgtcttttgg caatgtgagg gcccggaaac ctggccctgt cttcttgacg agcattccta     900
ggggtctttc ccctctcgcc aaaggaatgc aaggtctgtt gaatgtcgtg aaggaagcag     960
ttcctctgga agcttcttga agacaaacaa cgtctgtagc gaccctttgc aggcagcgga    1020
acccccacc tggcgacagg tgcctctgcg gccaaaagcc acgtgtataa gatacacctg     1080
caaaggcggc acaaccccag tgccacgttg tgagttggat agttgtggaa agagtcaaat    1140
ggctctcctc aagcgtattc aacaaggggc tgaaggatgc ccagaaggta ccccattgta    1200
tgggatctga tctggggcct cggtgcacat gctttacatg tgtttagtcg aggttaaaaa    1260
acgtctaggc cccccgaacc acggggacgt ggttttcctt tgaaaaacac gatgataata    1320
tgggcattga acaagatgga ttgcacgcag gttctccggc cgcttgggtg gagaggctat    1380
tcggctatga ctgggcacaa cagacaatcg gctgctctga tgccgccgtg ttccggctgt    1440
cagcgcaggg gcgcccggtt ctttttgtca agaccgacct gtccggtgcc ctgaatgaac    1500
tgcaggacga ggcagcgcgg ctatcgtggc tggccacgac gggcgttcct tgcgcagctg    1560
tgctcgacgt tgtcactgaa gcgggaaggg actggctgct attgggcgaa gtgccggggc    1620
aggatctcct gtcatctcac cttgctcctg ccgagaaagt atccatcatg gctgatgcaa    1680
tgcggcggct gcatacgctt gatccggcta cctgcccatt cgaccaccaa gcgaaacatc    1740
gcatcgagcg agcacgtact cggatggaag ccggtcttgt cgatcaggat gatctggacg    1800
aagagcatca ggggctcgcg ccagccgaac tgttcgccag gctcaaggcg cgcatgcccg    1860
acggcgagga tctcgtcgtg acccatggcg atgcctgctt gccgaatatc atggtggaaa    1920
atggccgctt ttctggattc atcgactgtg gccggctggg tgtggcggac cgctatcagg    1980
acatagcgtt ggctacccgt gatattgctg aagagcttgg cggcgaatgg gctgaccgct    2040
tcctcgtgct ttacggtatc gccgctcccg attcgcagcg catcgccttc tatcgccttc    2100
ttgacgagtt cttctgagcg ggactctggg gttcgaaatg accgaccaag cgacgcccaa    2160
cctgccatca cgatggccgc aataaaatat ctttattttc attacatctg tgtgttggtt    2220
ttttgtgtga atcgatagcg ataaggatcc gggctggcgt aatagcgaag aggcccgcac    2280
```

-continued

```
cgatcgccct tcccaacagt tgcgcagcct gaatggcgaa tggacgcgcc ctgtagcggc   2340

gcattaagcg cggcgggtgt ggtggttacg cgcagcgtga ccgctacact tgccagcgcc   2400

ctagcgcccg ctcctttcgc tttcttccct tcctttctcg ccacgttcgc cggctttccc   2460

cgtcaagctc taaatcgggg gctcccttta gggttccgat ttagagcttt acggcacctc   2520

gaccgcaaaa aacttgattt gggtgatggt tcacgtagtg ggccatcgcc ctgatagacg   2580

gtttttcgcc ctttgacgtt ggagtccacg ttctttaata gtggactctt gttccaaact   2640

ggaacaacac tcaaccctat ctcggtctat tcttttgatt tataagggat tttgccgatt   2700

tcggcctatt ggttaaaaaa tgagctgatt taacaaatat ttaacgcgaa ttttaacaaa   2760

atattaacgt ttacaatttc gcctgatgcg gtattttctc cttacgcatc tgtgcggtat   2820

ttcacaccgc atatggtgca ctctcagtac aatctgctct gatgccgcat agttaagcca   2880

gccccgacac ccgccaacac ccgctgacgc gccctgacgg gcttgtctgc tcccggcatc   2940

cgcttacaga caagctgtga ccgtctccgg gagctgcatg tgtcagaggt tttcaccgtc   3000

atcaccgaaa cgcgcgagac gaaagggcct cgtgatacgc ctatttttat aggttaatgt   3060

catgataata atggtttctt agacgtcagg tggcactttt cggggaaatg tgcgcggaac   3120

ccctatttgt ttatttttct aaatacattc aaatatgtat ccgctcatga gacaataacc   3180

ctgataaatg cttcaataat attgaaaaag gaagagtatg agtattcaac atttccgtgt   3240

cgcccttatt cccttttttg cggcattttg ccttcctgtt tttgctcacc cagaaacgct   3300

ggtgaaagta aaagatgctg aagatcagtt gggtgcacga gtgggttaca tcgaactgga   3360

tctcaacagc ggtaagatcc ttgagagttt tcgccccgaa gaacgttttc caatgatgag   3420

cacttttaaa gttctgctat gtggcgcggt attatcccgt attgacgccg ggcaagagca   3480

actcggtcgc cgcatacact attctcagaa tgacttggtt gagtactcac cagtcacaga   3540

aaagcatctt acggatggca tgacagtaag agaattatgc agtgctgcca taaccatgag   3600

tgataacact gcggccaact tacttctgac aacgatcgga ggaccgaagg agctaaccgc   3660

ttttttgcac aacatggggg atcatgtaac tcgccttgat cgttgggaac cggagctgaa   3720

tgaagccata ccaaacgacg agcgtgacac cacgatgcct gtagcaatgg caacaacgtt   3780

gcgcaaacta ttaactggcg aactacttac tctagcttcc cggcaacaat taatagactg   3840

gatggaggcg gataaagttg caggaccact tctgcgctcg gcccttccgg ctggctggtt   3900

tattgctgat aaatctggag ccggtgagcg tgggtctcgc ggtatcattg cagcactggg   3960

gccagatggt aagccctccc gtatcgtagt tatctacacg acggggagtc aggcaactat   4020

ggatgaacga aatagacaga tcgctgagat aggtgcctca ctgattaagc attggtaact   4080

gtcagaccaa gtttactcat atatacttta gattgattta aaacttcatt tttaatttaa   4140

aaggatctag gtgaagatcc tttttgataa tctcatgacc aaaatccctt aacgtgagtt   4200

ttcgttccac tgagcgtcag accccgtaga aaagatcaaa ggatcttctt gagatccttt   4260

ttttctgcgc gtaatctgct gcttgcaaac aaaaaaacca ccgctaccag cggtggtttg   4320

tttgccggat caagagctac caactctttt tccgaaggta actggcttca gcagagcgca   4380

gataccaaat actgtccttc tagtgtagcc gtagttaggc caccacttca agaactctgt   4440

agcaccgcct acatacctcg ctctgctaat cctgttacca gtggctgctg ccagtggcga   4500

taagtcgtgt cttaccgggt tggactcaag acgatagtta ccggataagg cgcagcggtc   4560

gggctgaacg gggggttcgt gcacacagcc cagcttggag cgaacgacct acaccgaact   4620

gagataccta cagcgtgagc tatgagaaag cgccacgctt cccgaaggga gaaaggcgga   4680
```

-continued caggtatccg gtaagcggca gggtcggaac aggagagcgc acgagggagc ttccaggggg 4740
aaacgcctgg tatctttata gtcctgtcgg gtttcgccac ctctgacttg agcgtcgatt 4800
tttgtgatgc tcgtcagggg ggcggagcct atggaaaaac gccagcaacg cggccttttt 4860
acggttcctg gccttttgct ggccttttgc tcacatggct cgacagatct 4910

<210> SEQ ID NO 5
<211> LENGTH: 6072
<212> TYPE: DNA
<213> ORGANISM: Artificial Sequence
<220> FEATURE:
<223> OTHER INFORMATION: Synthetic construct

<400> SEQUENCE: 5
gaattgctag caattgctag caattgctag caattcatac cagatcaccg aaaactgtcc 60
tccaaatgtg tcccccctcac actcccaaat tcgcgggctt ctgcctctta gaccactcta 120
ccctattccc cacactcacc ggagccaaag ccgcggccct tccgtttctt tgcttttgaa 180
agaccccacc cgtaggtggc aagctagctt aagtaacgcc actttgcaag gcatggaaaa 240
atacataact gagaatagaa aagttcagat caaggtcagg aacaaagaaa cagctgaata 300
ccaaacagga tatctgtggt aagcggttcc tgccccggct cagggccaag aacagatgag 360
acagctgagt gatgggccaa acaggatatc tgtggtaagc agttcctgcc ccggctcggg 420
gccaagaaca gatggtcccc agatgcggtc cagccctcag cagtttctag tgaatcatca 480
gatgtttcca gggtgcccca aggacctgaa aatgaccctg taccttattt gaactaacca 540
atcagttcgc ttctcgcttc tgttcgcgcg cttccgctct ccgagctcaa taaaagagcc 600
cacaacccct cactcggcgc gccagtcttc cgatagactg cgtcgcccgg gtacccgtat 660
tcccaataaa gcctcttgct gtttgcatcc gaatcgtggt ctcgctgttc cttgggaggg 720
tctcctctga gtgattgact acccacgacg ggggtctttc atttgggggc tcgtccggga 780
tttggagacc cctgcccagg gaccaccgac ccaccaccgg gaggtaagct ggccagcaac 840
ttatctgtgt ctgtccgatt gtctagtgtc tatgtttgat gttatgcgcc tgcgtctgta 900
ctagttagct aactagctct gtatctggcg gacccgtggt ggaactgacg agttctgaac 960
acccggccgc aaccctggga gacgtcccag ggactttggg ggccgttttt gtggcccgac 1020
ctgaggaagg gagtcgatgt ggaatccgac cccgtcagga tatgtggttc tggtaggaga 1080
cgagaaccta aaacagttcc cgcctccgtc tgaatttttg ctttcggttt ggaaccgaag 1140
ccgcgcgtct tgtctgctgc agcgctgcag catcgttctg tgttgtctct gtctgactgt 1200
gtttctgtat ttgtctgaaa attagggcca gactgttacc actcccttaa gtttgacctt 1260
aggtcactgg aaagatgtcg agcggatcgc tcacaaccag tcggtagatg tcaagaagag 1320
acgttgggtt accttctgct ctgcagaatg gccaaccttt aacgtcggat ggccgcgaga 1380
cggcaccttt aaccgagacc tcatcaccca ggttaagatc aaggtctttt cacctggccc 1440
gcatggacac ccagaccagg tcccctacat cgtgacctgg gaagccttgg cttttgaccc 1500
ccctccctgg gtcaagccct ttgtacaccc taagcctccg cctcctcttc ctccatccgc 1560
cccgtctctc ccccttgaac ctcctcgttc gaccccgcct cgatcctccc tttatccagc 1620
cctcactcct tctctaggcg ccggaattcg ttaactaact taagctagca acggtttccc 1680
tctagcggga tcaattccgc cccccccccc taacgttact ggccgaagcc gcttggaata 1740
aggccggtgt gcgtttgtct atatgttatt ttccaccata ttgccgtctt ttggcaatgt 1800

-continued

```
gagggcccgg aaacctggcc ctgtcttctt gacgagcatt cctaggggtc tttcccctct   1860
cgccaaagga atgcaaggtc tgttgaatgt cgtgaaggaa gcagttcctc tggaagcttc   1920
ttgaagacaa acaacgtctg tagcgaccct ttgcaggcag cggaaccccc cacctggcga   1980
caggtgcctc tgcggccaaa agccacgtgt ataagataca cctgcaaagg cggcacaacc   2040
ccagtgccac gttgtgagtt ggatagttgt ggaaagagtc aaatggctct cctcaagcgt   2100
attcaacaag gggctgaagg atgcccagaa ggtaccccat tgtatgggat ctgatctggg   2160
gcctcggtgc acatgcttta cgtgtgttta gtcgaggtta aaaaacgtct aggccccccg   2220
aaccacgggg acgtggtttt cctttgaaaa acacgataat accatgattg aacaagatgg   2280
attgcacgca ggttctccgg ccgcttgggt ggagaggcta ttcggctatg actgggcaca   2340
acagacaatc ggctgctctg atgccgccgt gttccggctg tcagcgcagg ggcgcccggt   2400
tctttttgtc aagaccgacc tgtccggtgc cctgaatgaa ctgcaggacg aggcagcgcg   2460
gctatcgtgg ctggccacga cgggcgttcc ttgcgcagct gtgctcgacg ttgtcactga   2520
agcgggaagg gactggctgc tattgggcga agtgccgggg caggatctcc tgtcatctca   2580
ccttgctcct gccgagaaag tatccatcat ggctgatgca atgcggcggc tgcatacgct   2640
tgatccggct acctgcccat tcgaccacca agcgaaacat cgcatcgagc gagcacgtac   2700
tcggatggaa gccggtcttg tcgatcagga tgatctggac gaagagcatc aggggctcgc   2760
gccagccgaa ctgttcgcca ggctcaaggc gcgcatgccc gacggcgagg atctcgtcgt   2820
gacccatggc gatgcctgct tgccgaatat catggtggaa aatggccgct tttctggatt   2880
catcgactgt ggccggctgg gtgtggcgga ccgctatcag gacatagcgt tggctacccg   2940
tgatattgct gaagagcttg gcggcgaatg ggctgaccgc ttcctcgtgc tttacggtat   3000
cgccgctccc gattcgcagc gcatcgcctt ctatcgcctt cttgacgagt tcttctgagc   3060
gggactctgg ggttcgataa aataaaagat tttatttagt ctccagaaaa aggggggaat   3120
gaaagacccc acctgtaggt ttggcaagct agcttaagta acgccatttt gcaaggcatg   3180
gaaaaataca taactgagaa tagagaagtt cagatcaagg tcaggaacag atggaacagc   3240
tgaatatggg ccaaacagga tatctgtggt aagcagttcc tgccccggct cagggccaag   3300
aacagatgga acagctgaat atgggccaaa caggatatct gtggtaagca gttcctgccc   3360
cggctcaggg ccaagaacag atggtcccca gatgcggtcc agccctcagc agtttctaga   3420
gaaccatcag atgtttccag ggtgccccaa ggacctgaaa tgaccctgtg ccttatttga   3480
actaaccaat cagttcgctt ctcgcttctg ttcgcgcgct tctgctcccc gagctcaata   3540
aaagagccca caacccctca ctcggggcgc cagtcctccg attgactgag tcgcccgggt   3600
acccgtgtat ccaataaacc ctcttgcagt tgcatccgac ttgtggtctc gctgttcctt   3660
gggagggtct cctctgagtg attgactacc cgtcagcggg ggtctttcat ttgggggctc   3720
gtccgggatc gggagacccc tgcccaggga ccaccgaccc accaccggga ggtaagctgg   3780
ctgcctcgcg cgtttcggtg atgacggtga aaacctctga cacatgcagc tcccggagac   3840
ggtcacagct tgtctgtaag cggatgccgg gagcagacaa gcccgtcagg gcgcgtcagc   3900
gggtgttggc gggtgtcggg gcgcagccat gacccagtca cgtagcgata gcggagtgta   3960
tactggctta actatgcggc atcagagcag attgtactga gagtgcacca tatgcggtgt   4020
gaaataccgc acagatgcgt aaggagaaaa taccgcatca ggcgctcttc cgcttcctcg   4080
ctcactgact cgctgcgctc ggtcgttcgg ctgcggcgag cggtatcagc tcactcaaag   4140
gcggtaatac ggttatccac agaatcaggg gataacgcag gaaagaacat gtgagcaaaa   4200
```

-continued

```
ggccagcaaa aggccaggaa ccgtaaaaag gccgcgttgc tggcgttttt ccataggctc   4260
cgcccccctg acgagcatca caaaaatcga cgctcaagtc agaggtggcg aaacccgaca   4320
ggactataaa gataccaggc gtttccccct ggaagctccc tcgtgcgctc tcctgttccg   4380
accctgccgc ttaccggata cctgtccgcc tttctccctt cgggaagcgt ggcgctttct   4440
catagctcac gctgtaggta tctcagttcg gtgtaggtcg ttcgctccaa gctgggctgt   4500
gtgcacgaac cccccgttca gcccgaccgc tgcgccttat ccggtaacta tcgtcttgag   4560
tccaacccgg taagacacga cttatcgcca ctggcagcag ccactggtaa caggattagc   4620
agagcgaggt atgtaggcgg tgctacagag ttcttgaagt ggtggcctaa ctacggctac   4680
actagaagga cagtatttgg tatctgcgct ctgctgaagc cagttacctt cggaaaaaga   4740
gttggtagct cttgatccgg caaacaaacc accgctggta gcggtggttt ttttgtttgc   4800
aagcagcaga ttacgcgcag aaaaaaagga tctcaagaag atcctttgat cttttctacg   4860
gggtctgacg ctcagtggaa cgaaaactca cgttaaggga ttttggtcat gagattatca   4920
aaaaggatct tcacctagat ccttttaaat taaaaatgaa gttttaaatc aatctaaagt   4980
atatatgagt aaacttggtc tgacagttac caatgcttaa tcagtgaggc acctatctca   5040
gcgatctgtc tatttcgttc atccatagtt gcctgactcc ccgtcgtgta gataactacg   5100
atacgggagg gcttaccatc tggccccagt gctgcaatga taccgcgaga cccacgctca   5160
ccggctccag atttatcagc aataaaccag ccagccggaa gggccgagcg cagaagtggt   5220
cctgcaactt tatccgcctc catccagtct attaattgtt gccgggaagc tagagtaagt   5280
agttcgccag ttaatagttt gcgcaacgtt gttgccattg ctgcaggcat cgtggtgtca   5340
cgctcgtcgt ttggtatggc ttcattcagc tccggttccc aacgatcaag gcgagttaca   5400
tgatccccca tgttgtgcaa aaaagcggtt agctccttcg gtcctccgat cgttgtcaga   5460
agtaagttgg ccgcagtgtt atcactcatg gttatggcag cactgcataa ttctcttact   5520
gtcatgccat ccgtaagatg cttttctgtg actggtgagt actcaaccaa gtcattctga   5580
gaatagtgta tgcggcgacc gagttgctct tgcccggcgt caacacggga taataccgcg   5640
ccacatagca gaactttaaa agtgctcatc attggaaaac gttcttcggg gcgaaaactc   5700
tcaaggatct taccgctgtt gagatccagt tcgatgtaac ccactcgtgc acccaactga   5760
tcttcagcat cttttacttt caccagcgtt tctgggtgag caaaaacagg aaggcaaaat   5820
gccgcaaaaa agggaataag ggcgacacgg aaatgttgaa tactcatact cttccttttt   5880
caatattatt gaagcattta tcagggttat tgtctcatga gcggatacat atttgaatgt   5940
atttagaaaa ataaacaaat aggggttccg cgcacatttc cccgaaaagt gccacctgac   6000
gtctaagaaa ccattattat catgacatta acctataaaa ataggcgtat cacgaggccc   6060
tttcgtcttc aa                                                       6072
```

```
<210> SEQ ID NO 6
<211> LENGTH: 5308
<212> TYPE: DNA
<213> ORGANISM: Artificial Sequence
<220> FEATURE:
<223> OTHER INFORMATION: Synthetic construct

<400> SEQUENCE: 6

tagttattaa tagtaatcaa ttacggggtc attagttcat agcccatata tggagttccg     60
cgttacataa cttacggtaa atggcccgcc tggctgaccg cccaacgacc cccgcccatt    120
```

-continued

```
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccgcccc tctccctccc ccccccctaa cgttactggc cgaagccgct tggaataagg    720
ccggtgtgcg tttgtctata tgttattttc caccatattg ccgtcttttg gcaatgtgag    780
ggcccggaaa cctggccctg tcttcttgac gagcattcct aggggtcttt cccctctcgc    840
caaaggaatg caaggtctgt tgaatgtcgt gaaggaagca gttcctctgg aagcttcttg    900
aagacaaaca acgtctgtag cgaccctttg caggcagcgg aaccccccac ctggcgacag    960
gtgcctctgc ggccaaaagc cacgtgtata agatacacct gcaaaggcgg cacaacccca   1020
gtgccacgtt gtgagttgga tagttgtgga aagagtcaaa tggctctcct caagcgtatt   1080
caacaagggg ctgaaggatg cccagaaggt accccattgt atgggatctg atctggggcc   1140
tcggtgcaca tgctttacat gtgtttagtc gaggttaaaa aaacgtctag gccccccgaa   1200
ccacggggac gtggttttcc tttgaaaaac acgatgataa tatggccaca accatggtga   1260
gcaagggcga ggagctgttc accggggtgg tgcccatcct ggtcgagctg gacggcgacg   1320
taaacggcca caagttcagc gtgtccggcg agggcgaggg cgatgccacc tacggcaagc   1380
tgaccctgaa gttcatctgc accaccggca agctgcccgt gccctggccc accctcgtga   1440
ccaccctgac ctacggcgtg cagtgcttca gccgctaccc cgaccacatg aagcagcacg   1500
acttcttcaa gtccgccatg cccgaaggct acgtccagga gcgcaccatc ttcttcaagg   1560
acgacggcaa ctacaagacc cgcgccgagg tgaagttcga gggcgacacc ctggtgaacc   1620
gcatcgagct gaagggcatc gacttcaagg aggacggcaa catcctgggg cacaagctgg   1680
agtacaacta caacagccac aacgtctata tcatggccga caagcagaag aacggcatca   1740
aggtgaactt caagatccgc cacaacatcg aggacggcag cgtgcagctc gccgaccact   1800
accagcagaa cacccccatc ggcgacggcc ccgtgctgct gcccgacaac cactacctga   1860
gcacccagtc cgccctgagc aaagacccca acgagaagcg cgatcacatg gtcctgctgg   1920
agttcgtgac cgccgccggg atcactctcg gcatggacga gctgtacaag taaagcggcc   1980
gcgactctag atcataatca gccataccac atttgtagag gttttacttg ctttaaaaaa   2040
cctcccacac ctccccctga acctgaaaca taaaatgaat gcaattgttg ttgttaactt   2100
gtttattgca gcttataatg gttacaaata aagcaatagc atcacaaatt tcacaaataa   2160
agcatttttt tcactgcatt ctagttgtgg tttgtccaaa ctcatcaatg tatcttaagg   2220
cgtaaattgt aagcgttaat attttgttaa aattcgcgtt aaatttttgt taaatcagct   2280
cattttttaa ccaataggcc gaaatcggca aaatccctta taaatcaaaa gaatagaccg   2340
agatagggtt gagtgttgtt ccagtttgga acaagagtcc actattaaag aacgtggact   2400
ccaacgtcaa agggcgaaaa accgtctatc agggcgatgg cccactacgt gaaccatcac   2460
cctaatcaag ttttttgggg tcgaggtgcc gtaaagcact aaatcggaac cctaaaggga   2520
```

-continued

```
gcccccgatt tagagcttga cggggaaagc cggcgaacgt ggcgagaaag gaagggaaga   2580
aagcgaaagg agcgggcgct agggcgctgg caagtgtagc ggtcacgctg cgcgtaacca   2640
ccacacccgc cgcgcttaat gcgccgctac agggcgcgtc aggtggcact tttcggggaa   2700
atgtgcgcgg aacccctatt tgtttatttt tctaaataca ttcaaatatg tatccgctca   2760
tgagacaata accctgataa atgcttcaat aatattgaaa aaggaagagt cctgaggcgg   2820
aaagaaccag ctgtggaatg tgtgtcagtt agggtgtgga aagtccccag gctccccagc   2880
aggcagaagt atgcaaagca tgcatctcaa ttagtcagca accaggtgtg gaaagtcccc   2940
aggctcccca gcaggcagaa gtatgcaaag catgcatctc aattagtcag caaccatagt   3000
cccgccccta actccgccca tcccgcccct aactccgccc agttccgccc attctccgcc   3060
ccatggctga ctaatttttt ttatttatgc agaggccgag gccgcctcgg cctctgagct   3120
attccagaag tagtgaggag gcttttttgg aggcctaggc ttttgcaaag atcgatcaag   3180
agacaggatg aggatcgttt cgcatgattg aacaagatgg attgcacgca ggttctccgg   3240
ccgcttgggt ggagaggcta ttcggctatg actgggcaca acagacaatc ggctgctctg   3300
atgccgccgt gttccggctg tcagcgcagg ggcgcccggt tctttttgtc aagaccgacc   3360
tgtccggtgc cctgaatgaa ctgcaagacg aggcagcgcg gctatcgtgg ctggccacga   3420
cgggcgttcc ttgcgcagct gtgctcgacg ttgtcactga agcgggaagg gactggctgc   3480
tattgggcga agtgccgggg caggatctcc tgtcatctca ccttgctcct gccgagaaag   3540
tatccatcat ggctgatgca atgcggcggc tgcatacgct tgatccggct acctgcccat   3600
tcgaccacca agcgaaacat cgcatcgagc gagcacgtac tcggatggaa gccggtcttg   3660
tcgatcagga tgatctggac gaagagcatc aggggctcgc gccagccgaa ctgttcgcca   3720
ggctcaaggc gagcatgccc gacggcgagg atctcgtcgt gacccatggc gatgcctgct   3780
tgccgaatat catggtggaa aatggccgct tttctggatt catcgactgt ggccggctgg   3840
gtgtggcgga ccgctatcag gacatagcgt tggctacccg tgatattgct gaagagcttg   3900
gcggcgaatg ggctgaccgc ttcctcgtgc tttacggtat cgccgctccc gattcgcagc   3960
gcatcgcctt ctatcgcctt cttgacgagt tcttctgagc gggactctgg ggttcgaaat   4020
gaccgaccaa gcgacgccca acctgccatc acgagatttc gattccaccg ccgccttcta   4080
tgaaaggttg ggcttcggaa tcgttttccg ggacgccggc tggatgatcc tccagcgcgg   4140
ggatctcatg ctggagttct tcgcccaccc tagggggagg ctaactgaaa cacggaagga   4200
gacaataccg gaaggaaccc gcgctatgac ggcaataaaa agacagaata aaacgcacgg   4260
tgttgggtcg tttgttcata aacgcggggt tcggtcccag ggctggcact ctgtcgatac   4320
cccaccgaga ccccattggg gccaatacgc ccgcgtttct tccttttccc caccccaccc   4380
cccaagttcg ggtgaaggcc cagggctcgc agccaacgtc ggggcggcag gccctgccat   4440
agcctcaggt tactcatata tactttagat tgatttaaaa cttcattttt aatttaaaag   4500
gatctaggtg aagatccttt ttgataatct catgaccaaa atcccttaac gtgagttttc   4560
gttccactga gcgtcagacc ccgtagaaaa gatcaaagga tcttcttgag atcctttttt   4620
tctgcgcgta atctgctgct tgcaaacaaa aaaaccaccg ctaccagcgg tggtttgttt   4680
gccggatcaa gagctaccaa ctctttttcc gaaggtaact ggcttcagca gagcgcagat   4740
accaaatact gtccttctag tgtagccgta gttaggccac cacttcaaga actctgtagc   4800
accgcctaca tacctcgctc tgctaatcct gttaccagtg gctgctgcca gtggcgataa   4860
```

-continued

```
gtcgtgtctt accgggttgg actcaagacg atagttaccg gataaggcgc agcggtcggg   4920

ctgaacgggg ggttcgtgca cacagcccag cttggagcga acgacctaca ccgaactgag   4980

atacctacag cgtgagctat gagaaagcgc cacgcttccc gaagggagaa aggcggacag   5040

gtatccggta agcggcaggg tcggaacagg agagcgcacg agggagcttc caggggggaaa  5100

cgcctggtat ctttatagtc ctgtcgggtt tcgccacctc tgacttgagc gtcgattttt   5160

gtgatgctcg tcaggggggc ggagcctatg gaaaaacgcc agcaacgcgg cctttttacg   5220

gttcctggcc ttttgctggc cttttgctca catgttcttt cctgcgttat cccctgattc   5280

tgtggataac cgtattaccg ccatgcat                                      5308
```

<210> SEQ ID NO 7
<211> LENGTH: 3703
<212> TYPE: DNA
<213> ORGANISM: Artificial Sequence
<220> FEATURE:
<223> OTHER INFORMATION: Synthetic construct

<400> SEQUENCE: 7

```
gggcgaatta attccggtta ttttccacca tattgccgtc ttttggcaat gtgagggccc     60

ggaaacctgg ccctgtcttc ttgacgagca ttcctagggg tctttcccct ctcgccaaag    120

gaatgcaagg tctgttgaat gtcgtgaagg aagcagttcc tctggaagct tcttgaagac    180

aaacaacgtc tgtagcgacc ctttgcaggc agcggaaccc cccacctggc gacaggtgcc    240

tctgcggcca aaagccacgt gtataagata cacctgcaaa ggcggcacaa ccccagtgcc    300

acgttgtgag ttggatagtt gtggaaagag tcaaatggct cacctcaagc gtattcaaca    360

aggggctgaa ggatgcccag aaggtacccc attgtatggg atctgatctg gggcctcggt    420

gcacatgctt tacatgtgtt tagtcgaggt taaaaaacgt ctaggccccc cgaaccacgg    480

ggacgtggtt ttcctttgaa aaacacgatg ataatatggc caccacccat atgaaagaaa    540

ccgctgctgc taaattcgaa cgccagcaca tggacagccc agatcagggt accctggtgc    600

cacgcggttc catggctgat atcggatccg aattcgagct ccgtcgacaa gcttgcggcc    660

gcactcgagc accaccacca ccaccactga gatctgactg aaaaaaaaaa aaaaaaaaaa    720

aaaaaaaaaa gtttaaacac tagtccgctg agcaataact agcataaccc cttggggcct    780

ctaaacgggt cttgaggggt tttttgctga aaggaggaac tatatccggg cttcctcgct    840

cactgactcg ctgcgctcgg tcgttcggct gcggcgagcg gtatcagctc actcaaaggc    900

ggtaatacgg ttatccacag aatcagggga taacgcagga aagaacatgt gagcaaaagg    960

ccagcaaaag gccaggaacc gtaaaaaggc cgcgttgctg gcgtttttcc ataggctccg   1020

cccccctgac gagcatcaca aaaatcgacg ctcaagtcag aggtggcgaa acccgacagg   1080

actataaaga taccaggcgt ttccccctgg aagctccctc gtgcgctctc ctgttccgac   1140

cctgccgctt accggatacc tgtccgcctt tctcccttcg ggaagcgtgg cgctttctca   1200

tagctcacgc tgtaggtatc tcagttcggt gtaggtcgtt cgctccaagc tgggctgtgt   1260

gcacgaaccc cccgttcagc ccgaccgctg cgccttatcc ggtaactatc gtcttgagtc   1320

caacccggta agacacgact tatcgccact ggcagcagcc actggtaaca ggattagcag   1380

agcgaggtat gtaggcggtg ctacagagtt cttgaagtgg tggcctaact acggctacac   1440

tagaaggaca gtatttggta tctgcgctct gctgaagcca gttaccttcg gaaaaagagt   1500

tggtagctct tgatccggca aacaaaccac cgctggtagc ggtggttttt ttgtttgcaa   1560

gcagcagatt acgcgcagaa aaaaggatc  tcaagaagat cctttgatct tttctacggg   1620
```

-continued

```
gtctgacgct cagtggaacg aaaactcacg ttaagggatt ttggtcatga gattatcaaa   1680
aaggatcttc acctagatcc ttttaaatta aaaatgaagt tttaaatcaa tctaaagtat   1740
atatgagtaa acttggtctg acagttacca atgcttaatc agtgaggcac ctatctcagc   1800
gatctgtcta tttcgttcat ccatagttgc ctgactcccc gtcgtgtaga taactacgat   1860
acgggagggc ttaccatctg gccccagtgc tgcaatgata ccgcgagacc cacgctcacc   1920
ggctccagat ttatcagcaa taaaccagcc agccggaagg gccgagcgca gaagtggtcc   1980
tgcaacttta tccgcctcca tccagtctat taattgttgc cgggaagcta gagtaagtag   2040
ttcgccagtt aatagtttgc gcaacgttgt tgccattgct acaggcatcg tggtgtcacg   2100
ctcgtcgttt ggtatggctt cattcagctc cggttcccaa cgatcaaggc gagttacatg   2160
atcccccatg ttgtgcaaaa aagcggttag ctccttcggt cctccgatcg ttgtcagaag   2220
taagttggcc gcagtgttat cactcatggt tatggcagca ctgcataatt ctcttactgt   2280
catgccatcc gtaagatgct tttctgtgac tggtgagtac tcaaccaagt cattctgaga   2340
atagtgtatg cggcgaccga gttgctcttg cccggcgtca atacgggata ataccgcgcc   2400
acatagcaga actttaaaag tgctcatcat tggaaaacgt tcttcggggc gaaaactctc   2460
aaggatctta ccgctgttga gatccagttc gatgtaaccc actcgtgcac ccaactgatc   2520
ttcagcatct tttactttca ccagcgtttc tgggtgagca aaaacaggaa ggcaaaatgc   2580
cgcaaaaaag ggaataaggg cgacacggaa atgttgaata ctcatactct tcctttttca   2640
atattattga agcatttatc agggttattg tctcatgagc ggatacatat ttgaatgtat   2700
ttagaaaaat aaacaaatag gggttccgcg cacatttccc cgaaaagtgc cacctgacgt   2760
ctaagaaacc attattatca tgacattaac ctataaaaat aggcgtatca cgaggccctt   2820
tcgtctcgcg cgtttcggtg atgacggtga aaacctctga cacatgcagc tcccggagac   2880
ggtcacagct tgtctgtaag cggatgccgg gagcagacaa gcccgtcagg gcgcgtcagc   2940
gggtgttggc gggtgtcggg gctggcttaa ctatgcggca tcagagcaga ttgtactgag   3000
agtgcaccat atatgcggtg tgaaataccg cacagatgcg taaggagaaa ataccgcatc   3060
aggaaattgt aaacgttaat attttgttaa aattcgcgtt aaatttttgt taaatcagct   3120
cattttttaa ccaataggcc gaaatcggca aaatccctta taaatcaaaa gaatagaccg   3180
agatagggtt gagtgttgtt ccagtttgga acaagagtcc actattaaag aacgtggact   3240
ccaacgtcaa agggcgaaaa accgtctatc agggcgatgg cccactacgt gaaccatcac   3300
cctaatcaag ttttttgggg tcgaggtgcc gtaaagcact aaatcggaac cctaaaggga   3360
gcccccgatt tagagcttga cggggaaagc cggcgaacgt ggcgagaaag gaagggaaga   3420
aagcgaaagg agcgggcgct agggcgctgg caagtgtagc ggtcacgctg cgcgtaacca   3480
ccacacccgc cgcgcttaat gcgccgctac agggcgcgtc gcgccattcg ccattcaggc   3540
tgcgcaactg ttgggaaggg cgatcggtgc gggcctcttc gctattacgc cagctggcga   3600
aagggggatg tgctgcaagg cgattaagtt gggtaacgcc agggttttcc cagtcacgac   3660
gttgtaaaac gacggccagt gaattgtaat acgactcact ata                     3703
```

<210> SEQ ID NO 8
<211> LENGTH: 1575
<212> TYPE: DNA
<213> ORGANISM: Rattus norvegicus

<400> SEQUENCE: 8

-continued

| | |
|---|---|
| gaattccgca ccgccaccgg gcaaattgtg gcagtcatcg gcgccgttgt ggatgtccag | 60 |
| ttcgatgagg gattaccacc tatcctaaat gccttggaag tgcaaggcag ggagagcaga | 120 |
| ctggttttgg aggtagccca gcatttaggg gagagcaccg tcagaactat tgctatggat | 180 |
| ggcactgaag gcttggttag aggccagaaa gtactggatt cgggggcacc aatcaaaatt | 240 |
| cctgttggtc ctgagacctt gggcagaatc atgaatgtca ttggagaacc tattgatgag | 300 |
| agaggtccta tcaaaaccaa acaattcgct cctattcatg ctgaggctcc tgaattcata | 360 |
| gagatgagtg ttgaacagga aattctggtg actggtataa aggttgtgga tctgctggcc | 420 |
| ccatacgcca agggtgggaa aatcggactc ttcggaggtg ctggtgttgg aaagacagta | 480 |
| ctgatcatgg agctaatcaa caatgttgct aaagcccatg gtggttattc tgtatttgct | 540 |
| ggtgttggtg agaggacccg tgagggcaat gatttatacc atgaaatgat tgagtctggt | 600 |
| gttatcaacc taaaagatgc cacttccaag gtagcgttgg tatatgggca gatgaatgaa | 660 |
| ccgcctggtg ctcgtgcccg ggtagctctg actggtctga ctgttgctga atacttcaga | 720 |
| gaccaggaag gccaagatgt cctgctgttt attgacaaca tcttccgctt cacccaggct | 780 |
| ggctcagagg tatctgcctt attgggcagg atcccgtctg ctgtaggcta ccagcctacc | 840 |
| ctagccactg acatgggtac aatgcaggaa agaatcacca ccaccaagaa gggctcgatc | 900 |
| acctcagtgc aggctatcta tgtgccagct gatgacctga ctgaccctgc ccctgcaact | 960 |
| acctttgccc atttggatgc tactactgtg ctgtcccgtg ctattgctga gttgggcatc | 1020 |
| tatccagctg tggatccgct ggactccacc tctcgaatta tggatcccaa catcgttggc | 1080 |
| agtgagcatt atgatgttgc tcgtggggtg caaaagatcc tgcaggacta caaatctctc | 1140 |
| caggacatca ttgccatctt gggtatggat gaactttctg aggaagataa attgactgtg | 1200 |
| tccagggcaa ggaagataca gcgcttcttg tcacagccat tccaggttgc tgaggtcttc | 1260 |
| acaggtcaca tgggaaagct ggtgcccctg aaggagacca ttaaaggatt ccagcagatc | 1320 |
| ttagcaggtg actatgacca tctcccggaa caagccttct acatggtggg acccattgaa | 1380 |
| gaagctgtgg caaaggctga caagctggca gaggagcatg ggtcgtgagg ggcccttcag | 1440 |
| ccaaacacaa cagcactctg cactgacctc catgctgaga gctcagtttg ccatgtaggc | 1500 |
| cacacaagag ccttgattga agatgtgatg ttctctctga agagtattta aagttttcaa | 1560 |
| taaagtatat accct | 1575 |